(12) United States Patent
Eggers et al.

(10) Patent No.: US 11,278,261 B1
(45) Date of Patent: Mar. 22, 2022

(54) APPARATUS, SYSTEM AND METHOD FOR THE DETECTION AND QUANTIFICATION OF CONDUCTANCE OF RIGHT-TO-LEFT CARDIAC SHUNTS

(71) Applicant: PFOmetrix, LLC, Dublin, OH (US)

(72) Inventors: Philip E. Eggers, Dublin, OH (US); Andrew R. Eggers, Ostrander, OH (US); David Thomas Dobson, Tacoma, WA (US)

(73) Assignee: PFOmetrix, LLC, Dublin, OH (US)

( * ) Notice: Subject to any disclaimer, the term of this patent is extended or adjusted under 35 U.S.C. 154(b) by 364 days.

(21) Appl. No.: 15/992,298

(22) Filed: May 30, 2018

Related U.S. Application Data

(60) Provisional application No. 62/513,460, filed on Jun. 1, 2017.

(51) Int. Cl.
*A61B 8/08* (2006.01)
*A61B 5/02* (2006.01)
(Continued)

(52) U.S. Cl.
CPC .............. *A61B 8/481* (2013.01); *A61B 5/026* (2013.01); *A61B 5/02028* (2013.01); *A61B 8/44* (2013.01);
(Continued)

(58) Field of Classification Search
CPC ........... A61B 8/481; A61B 8/52; A61B 8/467; A61B 8/461; A61B 8/46; A61B 8/44;
(Continued)

(56) References Cited

U.S. PATENT DOCUMENTS 6,196,972 B1    3/2001   Moehring
6,299,583 B1 * 10/2001   Eggers ................. A61B 5/0215
                                                                             600/341
(Continued)

FOREIGN PATENT DOCUMENTS

WO    WO 2011/127184     * 10/2011          A61B 5/02

OTHER PUBLICATIONS

Draganski et al. "Detection of Cardiac Right-to-Left Shunts by Contrast-Enhanced Harmonic Carotid Duplex Sonography." J Ultrasound Med 2005; 24:1071-1076.*
(Continued)

*Primary Examiner* — Amanda Lauritzen Moher
(74) *Attorney, Agent, or Firm* — Mueller Law, LLC; Jerry K. Mueller, Jr.

(57) ABSTRACT

A system for detecting/quantifying the conductance of a right-to-left cardiac shunt includes a mouthpiece assembly, a solenoid-driven vacuum/pressurization assembly; a controller for operating the solenoid-driven vacuum/pressurization assembly; and a monitor for displaying the instructions from the controller. A microbubble counting cell and digital image sensor are combined with software-based image analysis to determine a number of microbubbles contained in a microbubble counting zone. A monitor enables operator specification of total volume of contrast agent to be injected into the patient. One or more first Doppler ultrasound transducer arrays are positioned adjacent to targeted intracranial arteries at one side of the skull or a pair of first Doppler ultrasound transducer arrays positioned adjacent to targeted intracranial arteries at both sides of the skull. A second Doppler ultrasound transducer is positioned on the precordium of the patient to detect the arrival of microbubble-containing contrast agent in the right atrium of the patient.

6 Claims, 20 Drawing Sheets

(51) Int. Cl.

| | |
|---|---|
| *G06T 7/00* | (2017.01) |
| *A61B 5/026* | (2006.01) |
| *A61B 8/00* | (2006.01) |
| *A61B 5/087* | (2006.01) |
| *A61B 8/06* | (2006.01) |
| *A61B 5/00* | (2006.01) |
| *A61M 25/10* | (2013.01) |

(52) U.S. Cl.
CPC .......... *A61B 8/4416* (2013.01); *A61B 8/4477* (2013.01); *A61B 8/4494* (2013.01); *A61B 8/46* (2013.01); *A61B 8/461* (2013.01); *A61B 8/467* (2013.01); *A61B 8/488* (2013.01); *A61B 8/52* (2013.01); *G06T 7/0012* (2013.01); *A61B 5/087* (2013.01); *A61B 5/742* (2013.01); *A61B 8/06* (2013.01); *A61M 2025/102* (2013.01)

(58) Field of Classification Search
CPC ... A61B 8/4494; A61B 8/4477; A61B 8/4416; A61B 5/026; A61B 5/02028; A61B 8/488; A61B 5/742; A61B 8/06; A61B 5/087; G06T 7/0012; A61M 2025/102
See application file for complete search history.

(56) References Cited

U.S. PATENT DOCUMENTS

| | | | |
|---|---|---|---|
| 7,771,358 B2 | 8/2010 | Moehring | |
| 2010/0016731 A1* | 1/2010 | Eggers | A61B 5/02416 600/476 |
| 2010/0234758 A1 | 9/2010 | de Menezes | |
| 2011/0082373 A1* | 4/2011 | Gurley | A61B 8/481 600/454 |
| 2014/0171795 A1* | 6/2014 | Eggers | A61B 5/742 600/432 |
| 2014/0276034 A1* | 9/2014 | Eggers | A61B 5/0071 600/431 |
| 2015/0273134 A1* | 10/2015 | Spears | A61M 5/007 600/431 |

OTHER PUBLICATIONS

Lao et al. "Detection of right-to-left shunts: comparison between the International Consensus and Spencer Logarithmic Scale criteria." J Neuroimaging. 2008;18(4):402-406.*
Androulakis, Ischemic Stroke Subtypes and Migraine with Visual Aura in the ARIC Study. Neurology 2016; EPub Nov. 9, 2016.
Bang, Patent Foramen Ovale and Stroke—Current Status. Journal of Stroke 2015; 17(3): 229-237.
Cheli, Recurrent and Residual Shunts After Patent Foramen Ovale Closure: Results from a Long-Term Transcranial Doppler Study. Journal of Interventional Cardiology 2015; 28: 600-608.
Da Costa, Digital Image Analysis of Blood Cells. Clinical Laboratory Medicine 2015; 35: 105-122.
Droste, Contrast Transcranial Doppler ultrasound in the detection of right-to-left shunts: comparison of different procedures and different contrast agents. Stroke 1999; 30:1827-1832.
Dubourg, Contrast echocardiographic visualization of cough-induced right-to-left atrial shunt through a patent foramen ovale. Journal of American College of Cardiology 1984; 4: 587-594.
Fanning, Emerging Spectra of Silent Brain Infarction. Stroke 2014; 45: 3461-3471.
Hassell, Silent Cerebral Infarcts Associated with Cardiac Disease and Procedures. Nature Reviews Cardiology 2013; 10: 696-706.
Jeon, The Usefulness of a 10% Air-10% Blood-80% Saline Mixture for Contrast Echocardiography: Doppler Measurement of Pulmonary Artery Systolic Pressure. Journal of American College of Cardiology 2002; 39 [1]: 124-129.
Karttunen, Dye Dilution and Oximetry for Detection of Patent Foramen Ovale. Acta Neurol Scand 1998;97:231-236.
Khessali, The Effect of Patent Foramen Ovale Closure on Visual Aura without Headache or Typical Aura with Headache. Journal of American College of Cardiology: Cardiovascular Interventions 2012; 5: 682-687.
Kim, Paradoxical Embolism as the Cause of Silent Brain Infarctions in Healthy Subjects:the ICONS Study. European Journal of Neurology 2013; 20 [2]: 353-360.
Pfleger, Haemodynamic Quantification of Different Provocation Manoeuvers by Simultaneous Measurement of Right and Left Atrial Pressure: Implications for the Echocardiographic Detection of Persistent Patent Foramen Ovale. European Journal of Echocardiography 2001; 2: 88-93.
Purandare, Paradoxical Embolization and Cerebral White Matter Lesions in Dementia. British Journal of Radiology 2008; 81: 30-34, Abstract Only.
Purandare, Association of Cerebral Emboli With Accelerated Cognitive Deterioration in Alzheimer's Disease and Vascular Dementia. American Journal of Psychiatry. 2012; 169: 300-308.
Rigatelli, Permanent Right-to-Left Shunt Is the Key Factor in Managing Patent Foramen Ovale. Journal of the American College of Cardiology 2011; 58 [21]: 2257-2261.
Sastry, Is Transcranial Doppler for the Detection of Venous-to-Arterial Circulation Shunts Reproducible? Cerebrovascular Disease 2007; 23: 424-429.
Schuchlenz, Transesophageal Echocardiography for Quantifying the Size of Patent Foramen Ovale in Patients with Cryptogenic Cerebrovascular Events. Stroke Jan. 2002; 33 [1]: 293-296.
Shariat, Comparison of Agitated Saline Mixed with Blood to Agitated Saline Alone in Detecting Right-to-Left Shunt during Contrast-Transcranial Doppler Sonography Examination. Acta Neurology Taiwan 2011,20:182-187.
Smith, Cerebral Microinfarcts: The Invisible Lesions. Lancet Neurology 2012; 11 [3]: 272-282.
Spencer, Power M-Mode Transcranial Doppler for Diagnosis of Patent Foramen Ovale and Assessing Transcatheter Closure. American Society of Neuroimaging 2004; 14: 342-349.
Stewart, Contrast Echocardiography. Heart 2003; 89:342-348.
Tariq, Patent Foramen Ovale and Migraine: Closing the Debate—A Review. Headache 2016; 56 [3]: 462-478.
Tarantini, Patent Foramen Ovale Closure and Migraine Time Course: Clues for Positive Interaction. Int. Journal of Cardiology 2015; 195: 235-236, Abstract Only.
Yoon, Intermediate and Long-Term Results of Transcatheter Closure of Patent Foramen Ovale Using Amplatzer Patent Foramen Ovale Occluder: One Case of Pulmonary Embolism Irrespective of Patent Foramen Ovale Closure. Korean Circulation Journal 2011; 41: 356-362.
Zdradzinski, Contributors to and Impact of Residual Shunting After Device Closure of Atrial Septal Defects. American Heart Journal 2016; 177: 112-119.
Zhao, A Comparison of Transthroracic Echocardiograpy and Transcranial Doppler With Contrast Agent for Detection of Patent Foramen Ovale With or Without the Valsalva Maneuver. Medicine Oct. 2015; 94(43):1-5.
Reisman, Migraine Reduction after Transcatheter Closure of Interatrial Septal Defects: Another Brick in the Wall? Journal of Structural Heart Disease 2016; 2 [5]: 231-233.

* cited by examiner

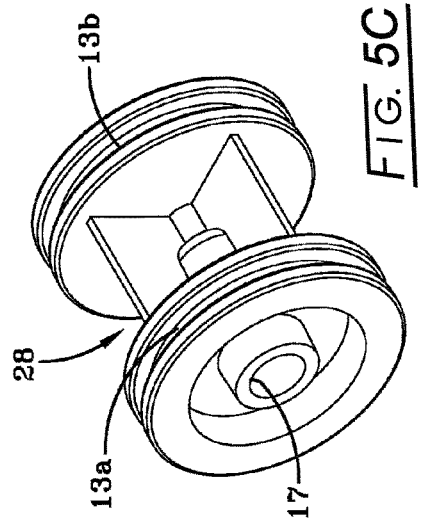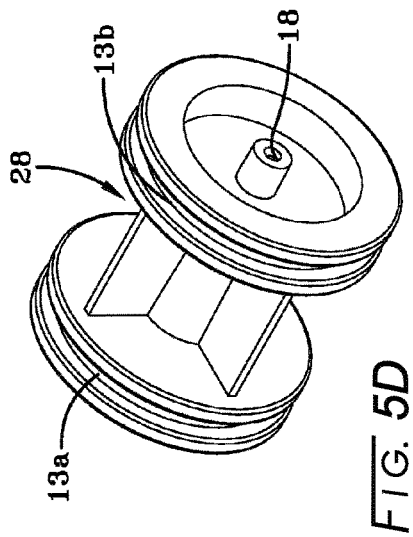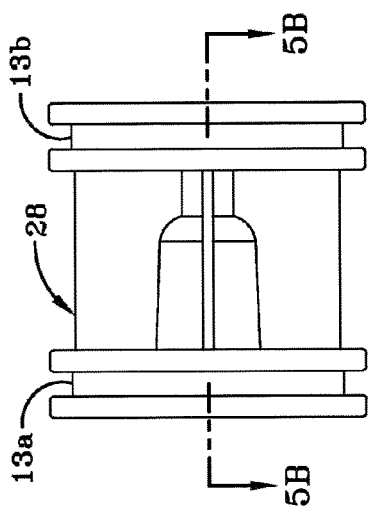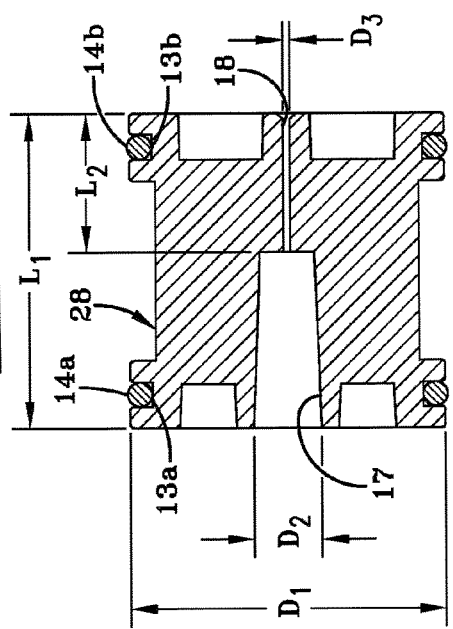

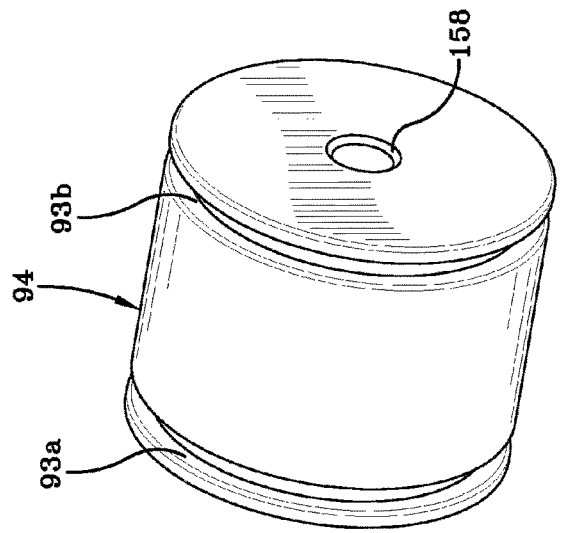
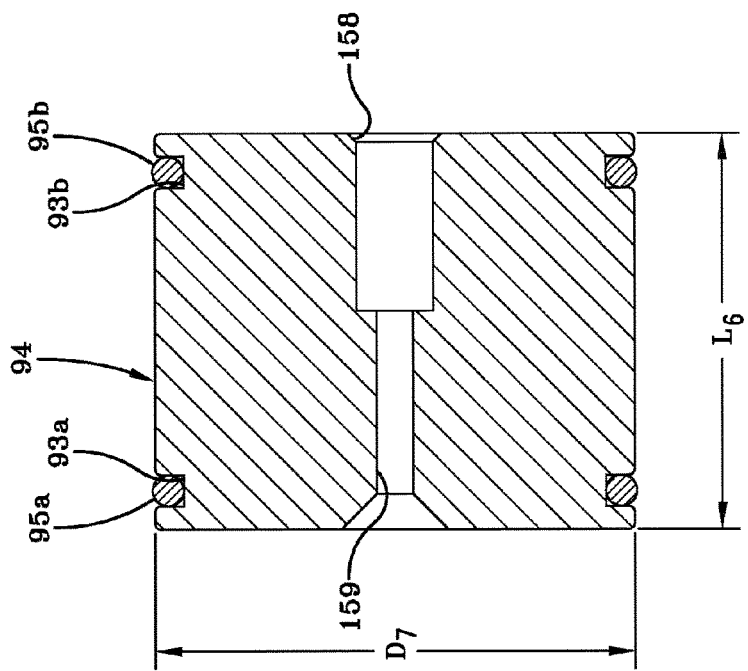

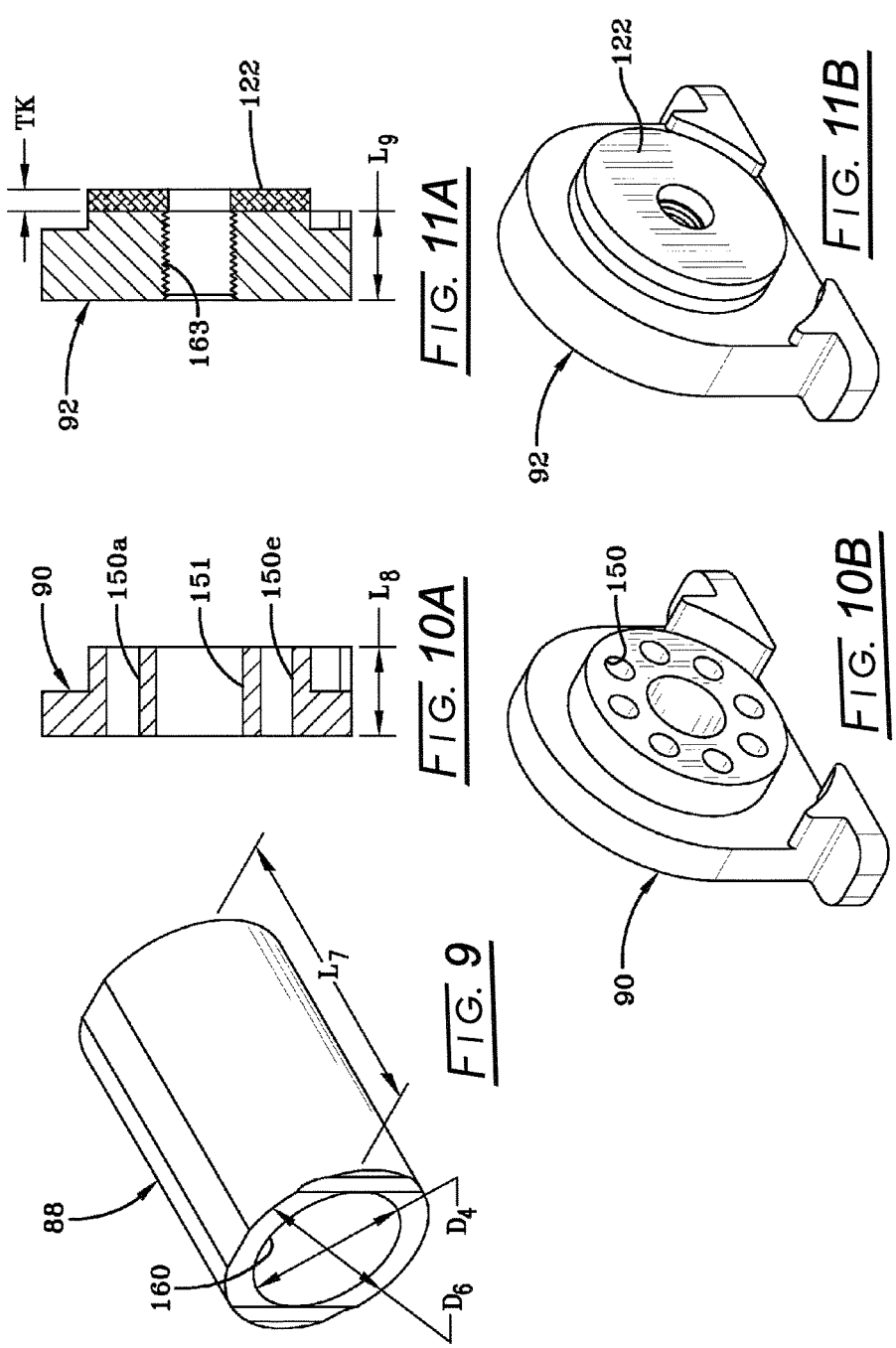

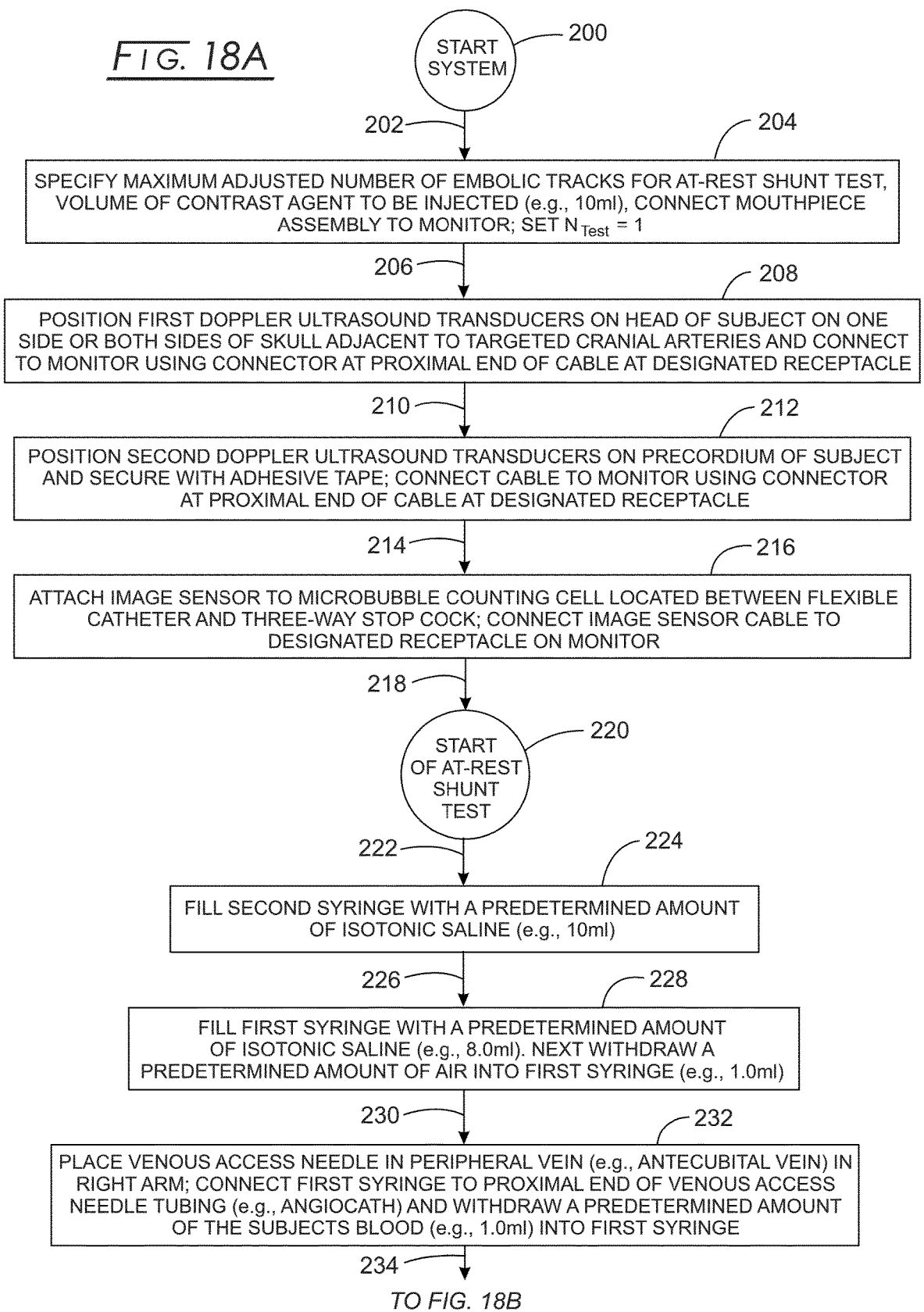

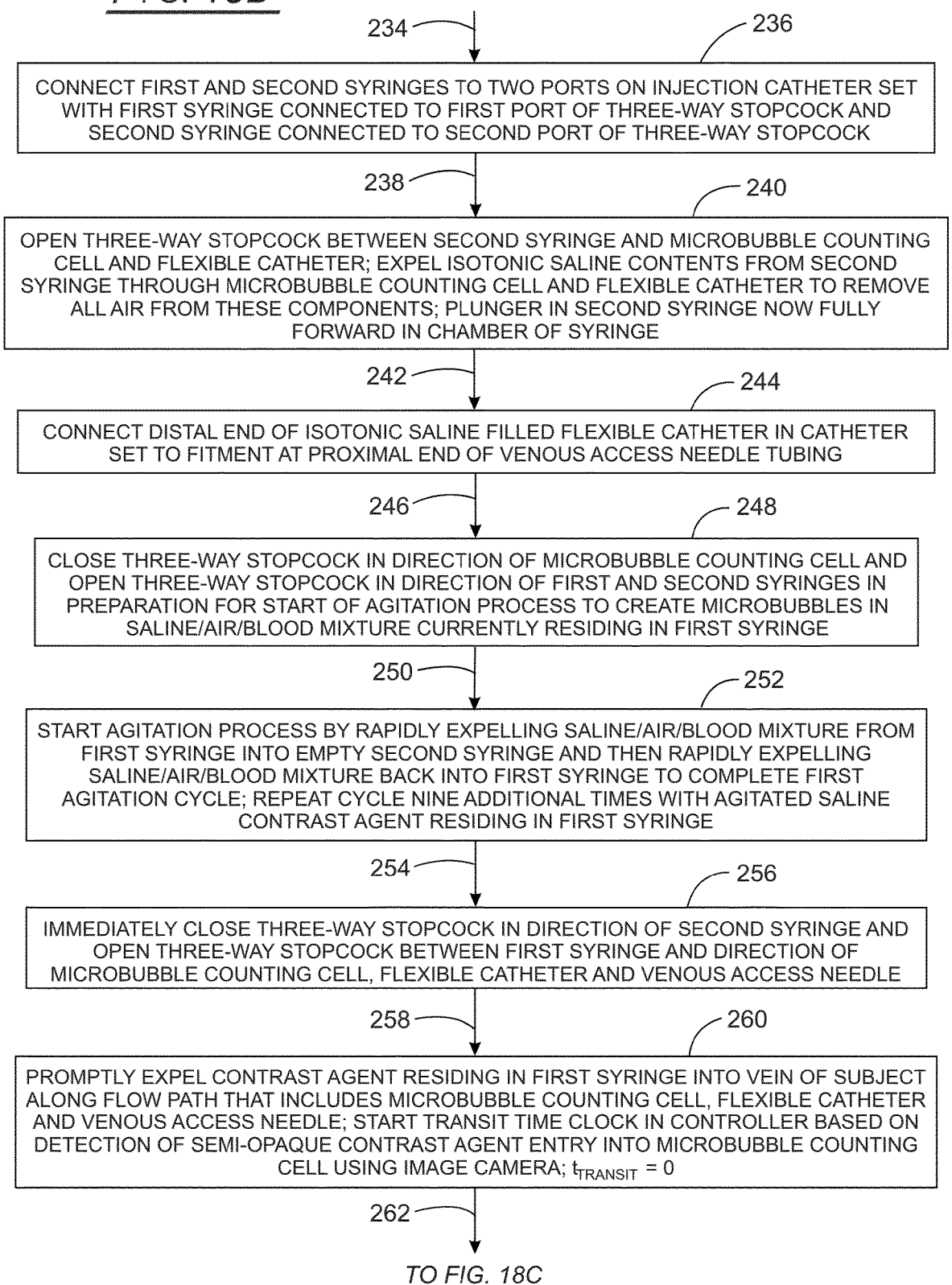

FIG. 18C    FROM FIG. 18B

264 — STOP TRANSIT TIME CLOCK WHEN SECOND DOPPLER ULTRASOUND TRANSDUCER POSITIONED AT PRECORDIAL LOCATION ON SUBJECT DETECTS ARRIVAL OF ECHOGENIC MICROBUBBLE IN RIGHT ATRIUM OF SUBJECT; MEASURED TRANSIT TIME FOR FLOW OF INJECTED CONTRAST AGENT FROM DETECTED ENTRY INTO MICROBUBBLE COUNTING CELL TO DETECTED ARRIVAL OF CONTRAST AGENT AT RIGHT ATRIUM SET TO $t_{TRANSIT}$ (e.g., 4.1 SECONDS)

268 — IMAGE SENSOR RECORDS IMAGE OF CONTRAST AGENT IN MICROBUBBLE COUNTING ZONE; RECORDED IMAGE OF CONTRAST AGENT ANALYZED IN CONTROLLER USING SOFTWARE-BASED IMAGE ANALYSIS TO COUNT NUMBER OF MICROBUBBLES IN MICROBUBBLE COUNTING ZONE OF MICROBUBBLE COUNTING CELL; DERIVE COUNT OF MICROBUBBLES IN MICROBUBBLE COUNTING ZONE USED TO RATIOMETRICALLY COMPUTE MUMBER OF MICROBUBBLES IN OPERATOR SPECIFIED VOLUME OF INJECTED CONTRAST AGENT, $N_{BUBBLES}$ (e.g., 2.85 MILLION MICROBUBBLES)

272 — FIRST DOPPLER ULTRASOUND TRANSDUCER ARRAY(S) POSITIONED AT ONE OR BOTH HEMISPHERES OF THE SKULL OF SUBJECT ADJACENT TO TARGETED CRANIAL ARTERIES RECORDS REFLECTED ULTRASOUND SIGNALS DURING A PREDEFINED TIME INTERVAL, $t_{COUNT}$ BEGINNING WITH DETECTED ARRIVAL OF MICROBUBBLE-FILLED CONTRAST AGENT IN RIGHT ATRIUM AND ENDING AFTER ELAPSED TIME INTERVAL, $t_{COUNT}$ (e.g., 30 SECOND TIME INTERVAL)

276 — SOFTWARE-BASED ALGORITHM IN CONTROLLER ANALYZES REFLECTED DOPPLER ULTRASOUND SIGNALS RECORDED BY FIRST DOPPLER ULTRASOUND ARRAY(S) TO DETERMINE NUMBER OF DETECTED EMBOLIC TRACTS CORRESPONDING TO MOVEMENT OF BLOOD-BORNE MICROBUBBLES IN INTRACRANIAL ARTERIES, $N_{ET}$ (e.g., $N_{ET}$ = 160)

280 — COMPUTE MICROBUBBLE ADJUSTMENT RATIO, $R_{BUBBLES}$ BY DIVIDING [1] A PRE-ESTABLISHED REFERENCE NUMBER OF INJECTED MICROBUBBLES, $N_{REF}$ (e.g., $N_{REF}$ = 1.50 MILLION MICROBUBBLES) THAT WAS USED TO DEVELOP A STANDARD GRADING SCALE FOR CONDUCTANCE OF RIGHT-TO-LEFT SHUNTS BY [2] THE ESTIMATED NUMBER OF MICROBUBBLES IN THE TOTAL VOLUME OF INJECTED CONTRAST AGENT, $N_{BUBBLES}$ (e.g., 2.85 MILLION MICROBUBBLES); IN PRESENT EXAMPLE $$R_{BUBBLES} = N_{REF}/N_{BUBBLES} = 1.50/2.85 = 0.526$$

TO FIG. 18D

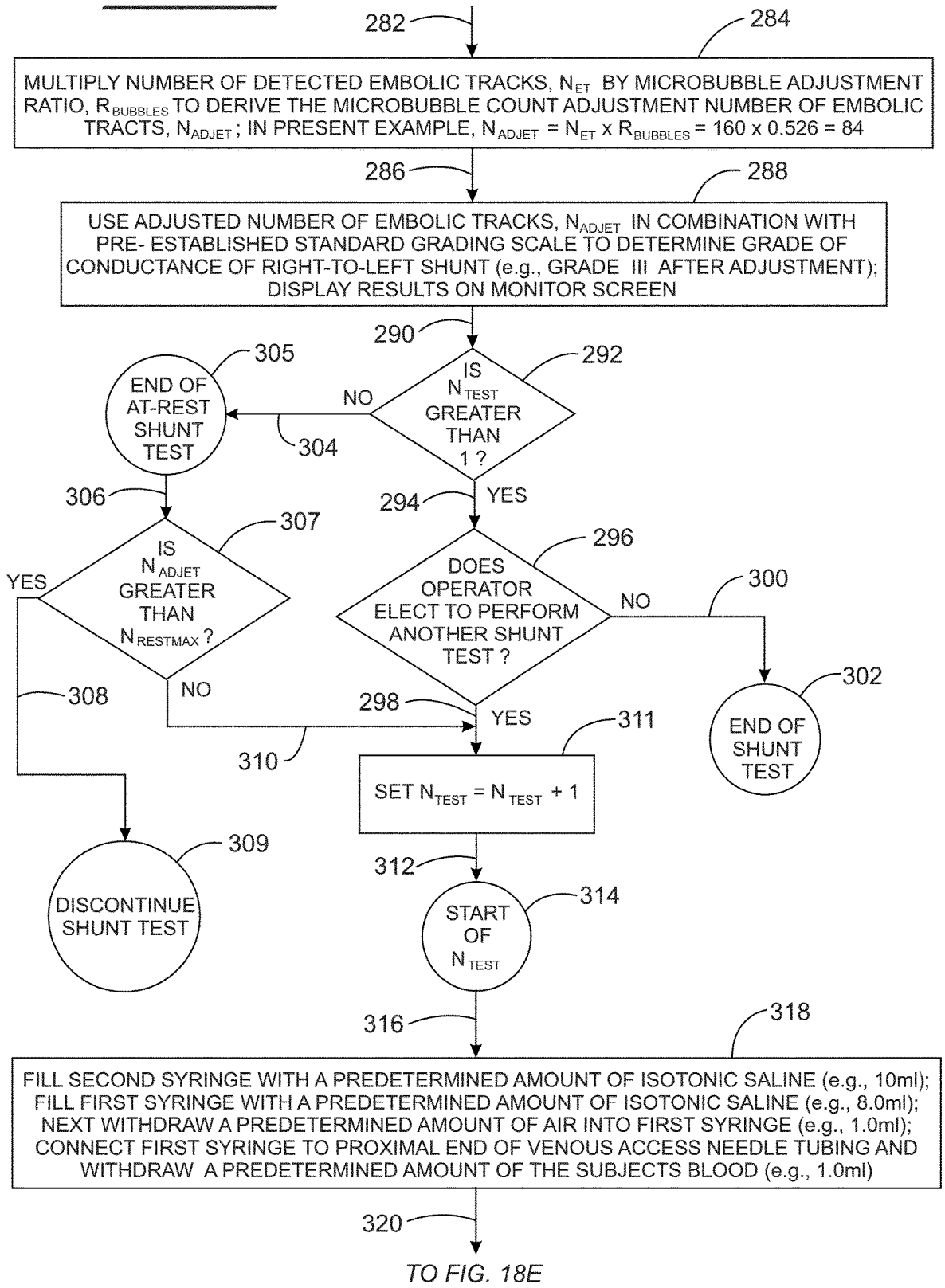

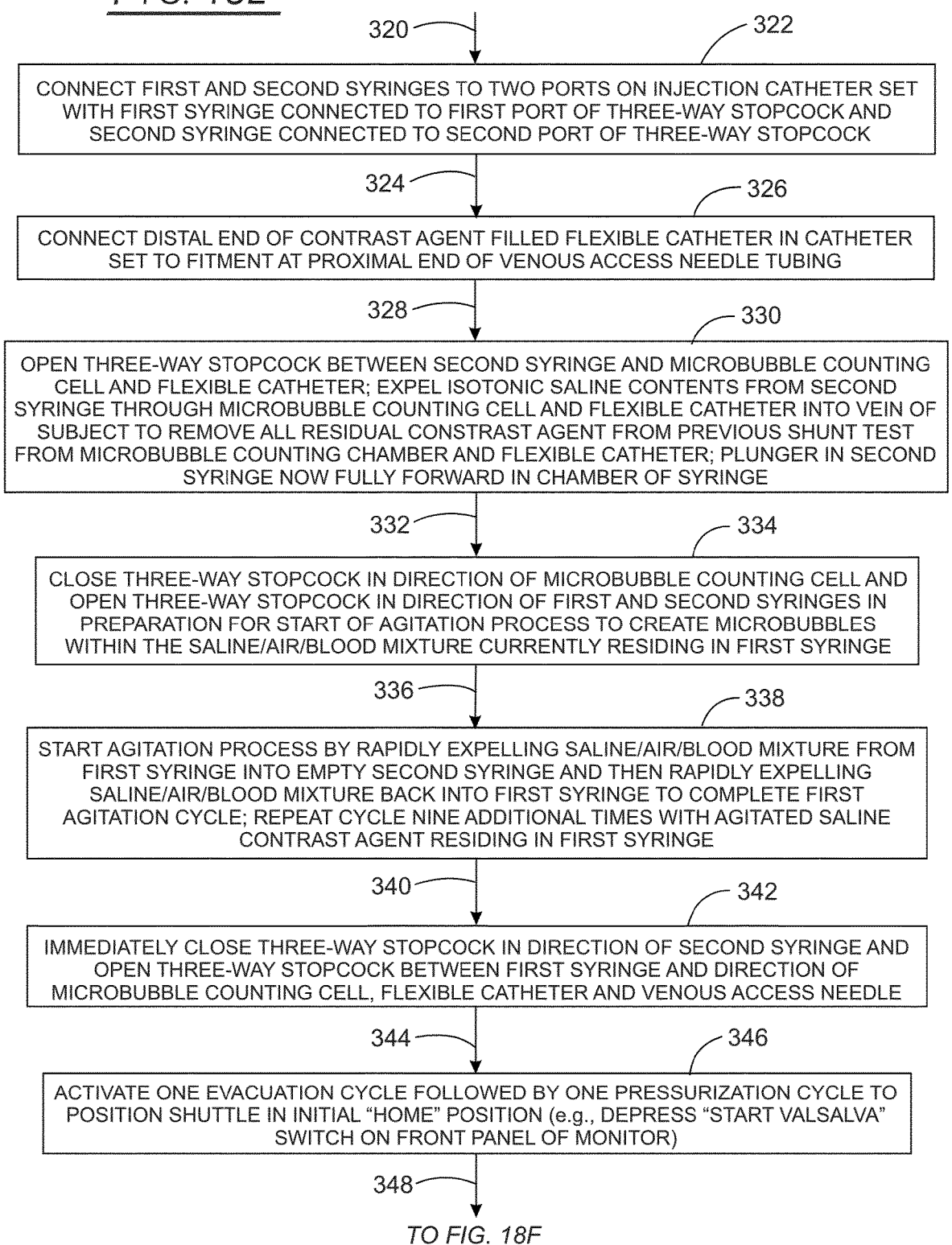

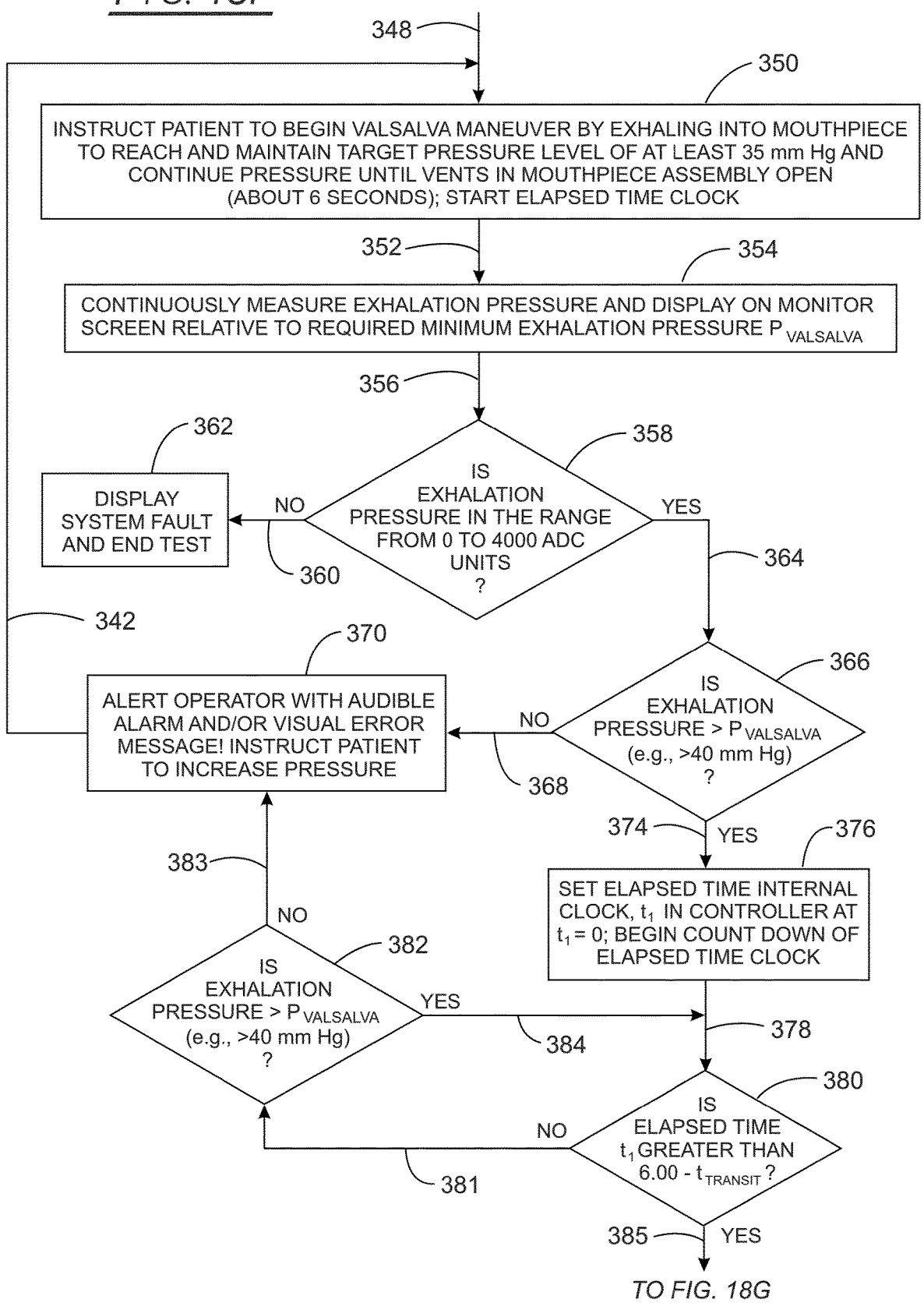

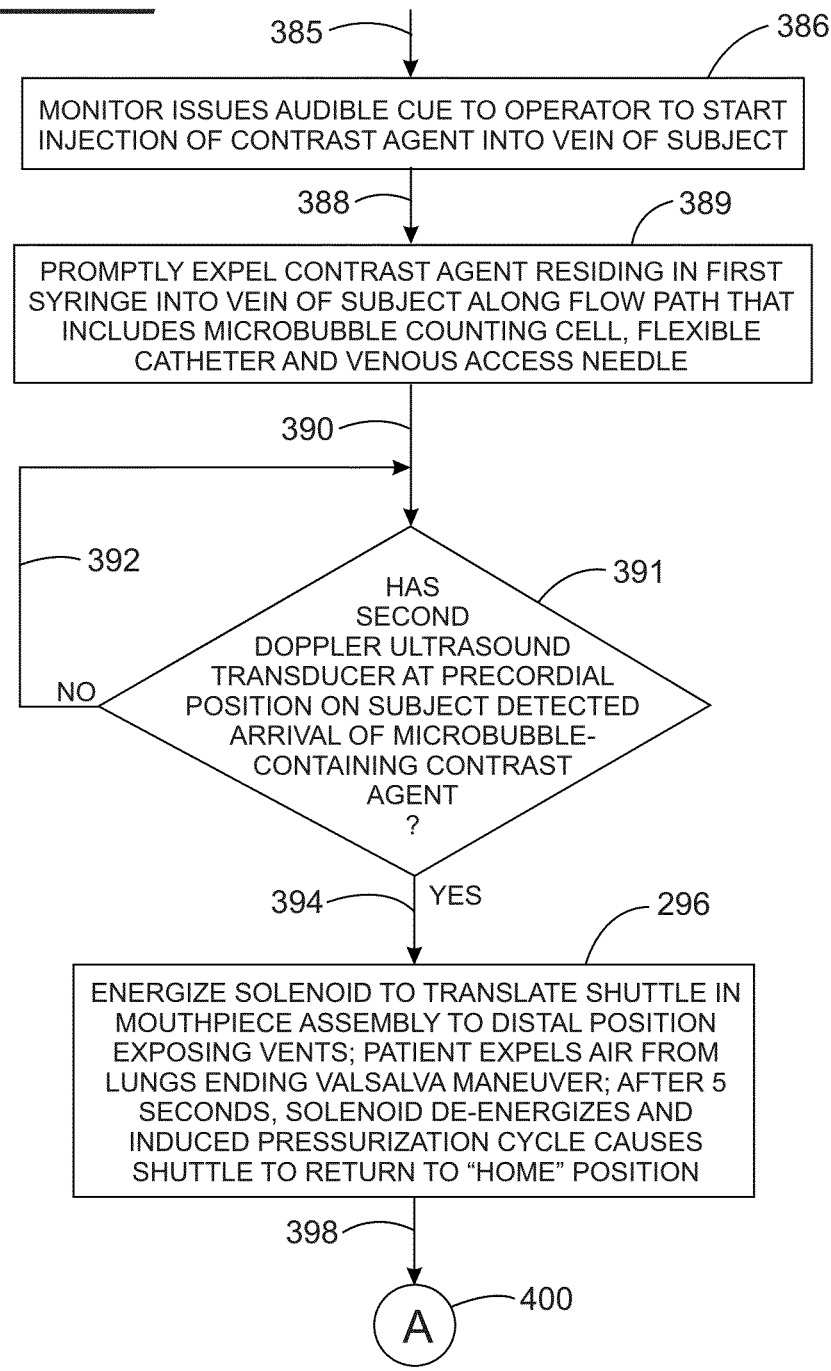

APPARATUS, SYSTEM AND METHOD FOR THE DETECTION AND QUANTIFICATION OF CONDUCTANCE OF RIGHT-TO-LEFT CARDIAC SHUNTS

CROSS-REFERENCE TO RELATED APPLICATIONS

This application claims benefit of provisional application 62/513,460 filed Jun. 1, 2017.

STATEMENT REGARDING FEDERALLY SPONSORED RESEARCH

Not applicable.

BACKGROUND

Cryptogenic strokes and transient ischemic attacks ("TIAs") are those in which no obvious cause is found by patient history, carotid Doppler studies, or cardiac conditions such as atrial fibrillation, myocardial infarction, or valve diseases. Patent foramen ovale ("PFO"), which is a small flap-valve hole in the heart, has been associated with cryptogenic stroke allowing paradoxical embolism from the veins to the brain through a right-to-left shunt ("RLS"). Normally, blood returning to the heart from the veins is re-oxygenated when it is pumped from the right side of the heart and then through the lungs. However, in people with PFO, the venous blood, which may contain clots, may instead travel through the hole (i.e., the PFO) between the upper chambers of the heart and into the arterial blood, bypassing the lungs where the clots would normally be filtered out. When this blood goes to the brain, a clot may cause a stroke or stroke-like symptoms. Hereinafter, the term "right-to-left shunt" refers to an abnormal pathway between the right side and the left side of the heart (e.g., an abnormal pathway or communication between the right atrium and the left atrium of the heart through the wall of the intervening septum). The most common abnormal pathway or communication between the right atrium and the left atrium of the heart is known as a PFO. A PFO is also the most common form of a right-to-left shunt. Normally, blood returning to the heart from the veins is re-oxygenated when it is pumped from the right side of the heart and then through the lungs as it proceeds to the left atrium. However, in subjects with a PFO, the venous blood, which may contain one or more emboli, may instead travel through the hole or pathway (e.g., a PFO) between the upper chambers of the heart and into the arterial blood, bypassing the lungs where the emboli would normally be filtered out. When venous blood bypasses the filtering benefit of the lungs and proceeds to the left side of the heart, that portion of the venous blood that proceeds to the brain may contain one or more emboli, thereby causing a stroke or stroke-like symptoms. In approximately 40 percent of stroke cases, the underlying cause is difficult to determine and the stroke is called "cryptogenic". Evidence now suggests that when a person has a stroke, and its cause is undetermined, the person is about twice as likely as the normal population to have PFO.

The presence of a PFO is found in all ages with diameters as large as 18 mm. Cryptogenic stroke patients, assessed with transcranial Doppler ultrasound ("TCD"), have a much higher likelihood of having a large PFO compared to subjects that have not experienced a stroke. Also, migraine patients, especially those experiencing migraine with aura, have a greater likelihood of having a PFO compared to subjects that do not experience migraine.

The presence of a PFO appears to be the source of silent or subclinical brain infarcts (SBIs) and small cortical infarcts. SBIs are associated with a 2x-increased risk of dementia and stroke. In this regard, see Bang, O., et al., Patent Foramen Ovale and Stroke—Current Status. Journal of Stroke 2015; 17(3): 229-237. In addition, paradoxical embolism has been identified as the main mechanism for SBI in otherwise healthy population. The consequences of SBI include mobility/gait disturbances, dementia, mild cognitive impairment, psychiatric disorders, e.g., bipolar disorder and depression (see Fanning, J., et al., Emerging Spectra of Silent Brain Infarction. Stroke 2014; 45: 3461-3471). In another clinical study of 1,103 patients, 31% of subjects exhibited SBI at MRI; of these 31%, 51% exhibited RLS upon examination by TCD. Prevalence of SBI in subjects with RLS is the same as the prevalence of cryptogenic stroke in subjects with RLS (see Kim, S., et al., Paradoxical Embolism as the Cause of Silent Brain Infarctions in Healthy Subjects: the ICONS Study. European Journal of Neurology 2013; 20 [2]: 353-360). The incidence of SBI (also known as microinfarcts) is 2x greater in subjects who died with dementia than those who died without dementia. Based on multiple studies, smaller and more numerous SBIs may be a stronger contributor to and causative factor for dementia (see Smith, E., et al., Cerebral Microinfarcts: The Invisible Lesions. Lancet Neurology 2012; 11 [3]: 272-282).

The existence of spontaneous cerebral emboli (SCE) were found to predict a more rapid progress of dementia in a study of 99 patients, 58 with Alzheimer's Disease (AD) and 41 with Vascular Dementia (VaD). SCE was detected in 44% of dementia patients and also was associated with the presence of significant PFO upon examination by TCD. The number of detected SCE significantly correlated with cognitive deterioration over 2 years of follow-up of Alzheimer's Disease and Vascular Dementia patients (see Purandare, N., et al., American Journal of Psychiatry. 2012; 169: 300-308). Also, Deep White Matter Hyperintensities (Deep WMH) were significantly associated with PFO in Alzheimer's Disease (AD), but not vascular dementia (VaD). Significant RLS (>15 microbubbles detected using TCD method) was associated with more severe deep WMH in Alzheimer's Disease and appears to be associated with the etiology of AD (Purandare, N., et al., Paradoxical Embolization and Cerebral White Matter Lesions in Dementia. British Journal of Radiology 2008; 81: 30-34).

Of 180 patients having a PFO that was detectable without any provocative maneuver (to increase right atrial pressure) exhibited an increased frequency of multiple ischemic brain lesions on magnetic resonance imaging as well as previous recurrent stroke, previous peripheral arterial embolism and migraine with aura (see Rigatelli, G., et al., Permanent Right-to-Left Shunt Is the Key Factor in Managing Patent Foramen Ovale. Journal of the American College of Cardiology 2011; 58 [21]: 2257-2261).

In view of the complications associated with presence of a PFO, especially a PFO exhibiting a larger shunt fraction (i.e., the fraction of blood flow through a PFO as compared with the magnitude of the overall blood flow through the heart), minimally invasive and non-invasive methods for detecting the presence of a PFO have evolved over the past two decades. Unfortunately, there is currently no available method suitable for widespread screening for the presence of an quantifying the conductance of a PFO when the patient experiences early warning signs signaling an ischemic incident, or the patient exhibits or is exposed to an elevated risk of a stroke. Consequently, the "at risk" fraction of the population with a right-to-left shunt is most often resigned to the possibility of experiencing a stroke before definitive right-to-left shunt testing is performed. Only then are methods such as transesophageal echocardiography (TEE) performed to detect the presence of a previously undiagnosed right-to-left shunt. If detected, the patient may elect to be treated with anti-clotting agents or elect to undergo transcatheter right-to-left shunt closure or the more conventional open-heart procedure for right-to-left shunt closure.

Transesophageal Echocardiography (TEE) in conjunction with the injection of agitated saline contrast agent containing very small, air filled "microbubbles" is considered the clinical "gold standard" for determining the presence of a right-to-left cardiac shunt. In this regard, see Shariat, A., et al., Comparison of Agitated Saline Mixed with Blood to Agitated Saline Alone in Detecting Right-to-Left Shunt during Contrast-Transcranial Doppler Sonography Examination. Acta Neurology Taiwan 2011; 20:182-187. In carrying out this test, microbubble filled contrast agent, produced by the agitation of a saline/air mixture with the optional addition of a small amount of the subject's blood, is injected into a vein (e.g., antecubital vein) leading to the right side of the heart. As this is underway, the somewhat sedated patient is required to bear down with their abdominal muscles (as during defecation) to perform a Valsalva strain, the release of which will momentarily reverse the pressure differential between the right and left atria and cause a PFO, if present, to open, while an ultrasound transducer, positioned in the esophagus at the level of the heart, is used to record the possible passage of microbubbles into the left atrium. Because of gagging problems, the patient is partially anesthetized. Typically, patients experience discomfort, and it is hardly suited for screening. The TEE test requires a physician with specialized training as well as an anesthesiologist or anesthetist. Attempts to perform semi-quantitative TEE tests have been shown to only correlate with PFO size if the microbubble-containing contrast agent was administered via femoral vein whereas poor correlation has been observed with PFO size when the contrast agent was administered via an antecubital vein (see Schuchlenz, H., et al., Transesophageal Echocardiography for Quantifying the Size of Patent Foramen Ovale in Patients with Cryptogenic Cerebrovascular Events. Stroke January, 2002; 33 [1]: 293-296). Hence, not only is TEE unsuitable for screening patients for the presence of a PFO but it is incapable of quantifying the shunt fraction or conductance (also referred to as the "size") of a right-to-left shunt.

A related test is referred to as transthoracic echocardiography (TTE). Again, a microbubble containing contrast agent is injected into a vein (e.g., antecubital vein) leading to the right side of the heart. Since the ultrasound detectors are positioned externally over the chest wall in a TTE, the Valsalva maneuver for this procedure is performed by having the patient blow forcefully into a small tube, sometimes connected to a manometer, while echocardiography recordings are made using ultrasound imaging through the chest wall. This procedure exhibits relatively poor sensitivity due the intervening distance between the transducer and the heart. Some clinical studies report a sensitivity of only 60% corresponding to a false-negative rate of 40%. For a comprehensive description of the exhalation-based Valsalva maneuver, see Pfleger, S., et al., Haemodynamic Quantification of Different Provocation Manoeuvers by Simultaneous Measurement of Right and Left Atrial Pressure: Implications for the Echocardiographic Detection of Persistent Patent Foramen Ovale. European Journal of Echocardiography 2001; 2: 88-93. In regard to the performance of a Valsalva maneuver, also see Spencer, M. S., et al., Power M-Mode Transcranial Doppler for Diagnosis of Patent Foramen Ovale and Assessing Transcatheter Closure. American Society of Neuroimaging 2004; 14: 342-349 and Zhao, E., et al., A Comparison of Transthroracic Echocardiograpy andTranscranial Doppler With Contrast Agent for Detection of Patent Foramen Ovale With or Without the Valsalva Maneuver. Medicine October 2015; 94(43):1-5. In addition to its poor sensitivity, the TTE method is incapable of quantifying the shunt fraction or conductance (also referred to as the "size") of a right-to-left shunt.

A third test, incorporating transcranial Doppler (TCD) technology, also uses microbubbles as a contrast agent along with a Valsalva maneuver. Regarding transcranial Doppler technology and method, see Spencer, M., et al., Power M-Mode Transcranial Doppler for Diagnosis of Patent Foramen Ovale and Assessing Transcatheter Closure. Journal of Neuroimaging 2004; 14:342-349). Ultrasonic transducers are positioned unilaterally or bilaterally on the skull to measure embolic signals produced by any microbubbles transiting the middle cerebral artery. The TCD method exhibits a relatively high sensitivity as compared with the TEE and TTE ultrasound methods. By way of example, U.S. Pat. No. 7,771,358, incorporated herein by reference, describes such systems and methods for grading microemboli flowing in targeted intracranial arteries using a Doppler Ultrasound method. Using intravenous injections of agitated saline, which provide an ultrasonic contrast agent of saline filled with a million or more microbubbles, the suspended bubbles pass through the PFO from the right atrium to the left atrium and are readily detected by the TCD ultrasound generated microembolic spectra emanating from the targeted cerebral arteries. The generated microbubbles within the agitated saline contrast agent do not pass through the lungs and into the left atrium. Therefore a shunt between the venous system and the arterial system that bypasses the lungs is the only way for bubbles to be seen on the arterial side of circulating blood. A provocative maneuver such as a Valsalva strain (forced expiratory effort against a closed glottis) or a breath-hold based Valsalva maneuver facilitates passage of the microbubbles through the PFO by raising the pressure in the right atrium over that of the left atrium.

As a further example of the use of the prior art TCD method described in U.S. Pat. No. 7,771,358 for the detection and quantification of the conductance of a right-to-left cardiac shunt, all embolic tracks (ETs) are counted in the bilaterally insonated intracranial arteries from a depth range of approximately 40 mm to 75 mm. Typically, all ETs are counted visually. Because the beams overlap at the midline at a depth of 75 mm, ETs are not counted at depths beyond 75 mm. Based on the number of ETs counted, a grade may be determined according to a six-level logarithmic grading scale to rate the degree of RLS: grade 0=0 ETs, grade I=1-10 ETs, grade II=11-30 ETs, grade III=31-100 ETs, grade IV=101-300 ETs, and grade V>300 ETs. The example six-level grading scale does not predict the physical size of the opening but does correspond to the conductance or ability of the right-to-left shunt to transmit emboli from the venous circulation to the arterial circulation of the brain.

The number of detected embolic tracks in the targeted cranial arteries following the injection of microbubbles into the venous circulation (e.g., injection at the antecubital vein of the subject) represents a quantifiable metric referred to hereinafter as the "conductance" of a right-to-left shunt. The measured number of embolic tracks detected in cranial arteries is dependent on many factors including [a] the right-to-left shunt flow distribution to the anterior circulation of the brain, the size of the foramen ovale that temporarily opens when the exhalation pressure exerted by the subject abruptly ends (i.e., the end of the Valsalva maneuver), the length of the pathway through the wall of the heart separating the venous and arterial circulation of blood within the heart (e.g., the length of the pathway through the septum located between the right and left atria), the tortuosity of the pathway length, the right-to-left pressure gradient during the brief period when the foramen ovale is open and the total number of microbubbles contained in the volume of injected contrast agent.

In the case of the unilateral TCD detection method, the number of ETs counted are doubled based on the assumption of an equal distribution of blood flowing through the left and right hemispheres of the brain. The resulting number of ETs is then applied to the six-level grading scale described above. Although the use of TCD provides greater accuracy for the detection or ruling out of right-to-left shunts as well as an improved grading scale for determining the functional conductance of PFO, it is not without significant limitations. For example, current TCD devices and methods require the services of a trained neurosonographer to perform the time-consuming process of visually analyzing TCD generated ultrasound spectra and counting of the ETs detected during examination. Additionally, counting the number of ETs for the higher grades, such as grades VI and above in the above example, is difficult as visually distinguishing between individual ETs on the recorded ultrasound spectra. As a result, the grading process, specifically for right-to-left shunts such as PFO is susceptible to operator-dependent counting errors.

Another significant limitation of the use of existing TCD devices and methods to quantify the conductance of a right-to-left shunt is the inconsistency of operator-prepared agitated saline mixtures to produce the microbubble-containing contrast agent as a circulatory tracking indicator. In current practice, microbubbles are created just prior to use by filling a first syringe with, by way of example, 8.0 ml of sterile isotonic saline, 1.0 ml of air and 0.5 to 1.0 ml of blood withdrawn from the patient. This mixture is then rapidly transferred into an initially empty second syringe and, after which, the saline/air/blood mixture within the second syringe is rapidly injected back into the first syringe to complete one mixing cycle. This process causes the air to be dispersed within the saline and blood liquid mixture in the form of small bubbles. Alternatively, microbubbles are created just prior to use by filling a first syringe with, by way of example, 9.0 ml of sterile isotonic saline and 1.0 ml of air. This mixture is then rapidly transferred into an initially empty second syringe and, after which, the saline/air mixture within the second syringe is rapidly injected back into the first syringe to complete one mixing cycle. This process causes the air to be dispersed within the saline liquid in the form of small bubbles. This mixing cycle process is typically repeated six to ten times in rapid succession resulting in a mixture containing millions of microbubbles typically having a mean diameter of about 25 microns (i.e., micrometers). Unfortunately, the microbubbles generated using the above described manual agitation process [a] vary in total number per unit volume of contrast agent and [b] are highly unstable during the time domain of performing a TCD test procedure.

The size of the microbubbles in contrast agents used for the detection of right-to-left shunts using TCD methods is important. The saline agitation method described above generates microbubbles whose diameter is at least 10 microns for more than 99% of the microbubbles generated. The preferred size microbubbles for TCD as well as Transthoracic Echocardiography (TTE) and Transesophageal Echocardiography (TEE) is greater than 10 microns and typically the generated microbubbles have a geometric mean diameter of 25 to 29 microns. The vast majority of the microbubbles produced by the manual agitation of a saline/air mixture as well as saline/air/blood mixture are too large to cross the pulmonary vasculature (see Stewart, M, Contrast Echocardiography. Heart 2003; 89:342-348).

By way of example, a first contrast agent study reports a geometric mean microbubble diameter of 28.9 microns with a range of 10 to 338 microns for saline/air/blood mixtures prepared with 8.0 ml saline, 1.0 ml air and 0.5 ml of patient's blood. In this first study, the microbubble diameter ranged from 12.5 to 78.7 microns for 1% to 99% of the population with the smallest microbubble at least 10 micron in diameter. In the inter-investigator comparison in this first study, the geometric mean microbubble diameter was 26.7 microns and 28.7 microns for Investigator 1 and 2, respectively, for the above-specified saline/air/blood mixture. For further information regarding this first study, see Sastry, S., et al., Is Transcranial Doppler for the Detection of Venous-to-Arterial Circulation Shunts Reproducible? Cerebrovascular Disease 2007; 23: 424-429.

In another example, a second contrast agent study reports on the characteristics of an agitated saline mixture containing 8.0 ml saline, 1.0 ml air and 1.0 ml blood. The agitated saline contrast agent prepared with this particular mixture yielded an average microbubble size of 26.7 microns with a standard deviation of 7.2. For further information regarding this second study, see Jeon, D., et al., The Usefulness of a 10% Air-10% Blood-80% Saline Mixture for Contrast Echocardiography: Doppler Measurement of Pulmonary Artery Systolic Pressure. Journal of American College of Cardiology 2002; 39 [1]: 124-129.

In yet another example, a third contrast agent study reports on the characteristics of an agitated saline mixture containing 9.0 ml saline, 1.0 ml without any addition of blood withdrawn from the subject. The agitated saline contrast agent prepared with this particular mixture yielded an average microbubble size of 31.6 microns with a standard deviation of 8.2 microns For further information regarding this third study, also see Jeon, D., et al., The Usefulness of a 10% Air-10% Blood-80% Saline Mixture for Contrast Echocardiography: Doppler Measurement of Pulmonary Artery Systolic Pressure. Journal of American College of Cardiology 2002; 39 [1]: 124-129.

Although the mean microbubble diameter was similar in the three example studies referenced above, the range of microbubble diameters was somewhat greater in the first study. However and importantly, the number of microbubbles produced was significantly different between the three example studies. By way of example, in a first study using a contrast agent prepared with 8.0 ml saline, 1.0 ml air and 0.5 ml of patient's blood, the geometric mean number of bubbles was 451/mm$^3$ with a range (95% Confidence Interval) from 409/mm$^3$ to 498/mm$^3$ after six mixing cycles. After 18 mixing cycles, the geometric mean number of bubbles was 857/mm$^3$ with a range (95% Confidence Interval) from 757/mm$^3$ to 926/mm$^3$ (see Sastry, S., et al., Is Transcranial Doppler for the Detection of Venous-to-Arterial Circulation Shunts Reproducible? Cerebrovascular Disease 2007; 23: 424-429).

In a second study using a contrast agent prepared with 8.0 ml saline, 1.0 ml air and 1.0 ml of patient's blood, the geometric mean number of bubbles was 2,285/mm$^3$ with a standard deviation of 704/mm$^3$ after 10 mixing cycles. In contrast, in a third study using a contrast agent prepared with 9.0 ml saline and 1.0 ml air, but without the addition of any patient's blood, the geometric mean number of bubbles was 193/mm³ with a standard deviation of 153/mm³ after 10 mixing cycles. In regard to the second and third study, see Jeon, D., et al., The Usefulness of a 10% Air-10% Blood-80% Saline Mixture for Contrast Echocardiography: Doppler Measurement of Pulmonary Artery Systolic Pressure. Journal of American College of Cardiology 2002; 39 [1]: 124-129.

A comparison of the first and second studies describe above reveals that the two-fold larger amount of added blood for the saline/air/blood mixture in the first study resulted in a three-fold larger number of microbubbles. More significantly, for the case of the third study in which the contrast agent was prepared with 9.0 ml saline, 1.0 ml air without the addition of the patient's blood, the geometric mean number of bubbles was only 193/mm³, a factor of about twelve-fold lower than the number of microbubbles generated when the patient's blood is added to the saline/air mixture.

In addition to significant variations in the number of microbubbles generated per unit volume of manually prepared contrast agent, as describe in the three example studies cited above, there is also a significant variation in the number of microbubbles per unit volume of contrast agent depending on the elapsed time between the completion of the last agitation cycle and the injection of the contrast agent into the venous blood stream of the subject. The half-life values for microbubbles prepared by two different methods involving agitation of saline and air with and without the addition of blood have been reported (see Jeon, D., et al., The Usefulness of a 10% Air-10% Blood-80% Saline Mixture for Contrast Echocardiography: Doppler Measurement of Pulmonary Artery Systolic Pressure. Journal of American College of Cardiology 2002; 39 [1]: 124-129). The measured and reported half-life values of the generated microbubbles range from 4.2 seconds (for saline/air mixture) to 4.9 seconds (for saline/air/blood mixture). Hence, if the operator delays the start of injection by about 4 to 5 seconds rather than injecting immediately after the last agitation cycle, then the number of injected microbubbles will decrease by a two-fold factor.

By way of example, if a typically used 10 ml volume of agitated saline/air/blood mixture (80%/10%/10% composition) is injected immediately after the $10^{th}$ mixing cycle, the estimated number of microbubbles injected will be 2,285 bubbles/mm³×1,000 mm³/ml×10 ml or 22.85 million microbubbles. If the operator performing a TCD test delays the start of the injection of this agitated saline mixture by 5.0 seconds, the estimated number of microbubbles injected will be 14.97 million microbubbles in a 10 ml volume of injected agitated saline contrast, a nearly two-fold lower number of microbubbles. In another example, if the operator performing TCD test delays the start of the injection of this agitated saline mixture by 10.0 seconds, the estimated number of microbubbles injected will be only 4.31 million microbubbles in a 10 ml volume of injected agitated saline contrast, a five-fold lower number of microbubbles as compared with the number of microbubbles in the contrast agent when it is injected immediately after the last agitation cycle. In this regard, see Jeon, D., et al., The Usefulness of a 10% Air-10% Blood-80% Saline Mixture for Contrast Echocardiography: Doppler Measurement of Pulmonary Artery Systolic Pressure. Journal of American College of Cardiology 2002; 39 [1]: 124-129.

In yet another example and in contrast to the case of a saline/air/blood agitated saline mixture, if a 10 ml volume of agitated saline/air mixture without the addition of blood (e.g., 9 ml saline+1.0 ml air) is injected immediately after the $10^{th}$ mixing cycle, the estimated number of microbubbles injected will be 193 bubbles/mm³×1,000 mm³/ml×10 ml or 1.93 million microbubbles. If the operator performing TCD test delays the start of the injection of this agitated saline mixture by 5.0 seconds, the estimated number of microbubbles injected will be 890,000 microbubbles in a 10 ml volume of injected agitated saline contrast, a number of microbubbles that is more than two-fold lower than if the contrast agent is injected immediately and about 17× smaller than for the case of the saline/air/blood agitated saline mixture. If the operator performing a TCD test delays the start of the injection of this agitated saline mixture by 10.0 seconds, the estimated number of microbubbles injected will be 350,000 microbubbles in a 10 ml volume of injected agitated saline contrast, a number of microbubbles over 12× smaller than for the case of the saline/air/blood agitated saline mixture. In this regard, also see Jeon, D., et al., The Usefulness of a 10% Air-10% Blood-80% Saline Mixture for Contrast Echocardiography: Doppler Measurement of Pulmonary Artery Systolic Pressure. Journal of American College of Cardiology 2002; 39 [1]: 124-129.

The significance of these differences in the total number of microbubbles contained in the injected contrast agent is that [a] the composition of the contrast agent (e.g., composition with or without the addition of blood), [b] the number and forcefulness of the agitation cycles and [c] delays in the start of injection of the agitated saline/air/blood or agitated saline/air mixtures significantly affect the absolute number of embolic tracks (ETs) counted for right-to-left shunts. The number of detected ETs during a TCD shunt test is essential to distinguishing between large (Grade IV, 101-300 ETs), medium (Grade III, 31-100 ETs), small (Grade II, 11-30 ETs) and very small (Grade I, 1-10 ETs) shunt conductances (see Spencer, et al., Power M-Mode Transcranial Doppler for Diagnosis of Patent Foramen Ovale and Assessing Transcatheter Closure. Journal of Neuroimaging 2004; 14:342-349). By way of example, for an actual Grade III shunt using agitated 80% saline/10% air/10% blood mixture, assume the number of microbubble-induced ETs detected in the middle cerebral artery (MCA) using TCD could be 40 ETs if the operator injected the contrast agent immediately after the last of 10 agitation cycles corresponding to a medium or Grade III shunt conductance. However, if the operator delayed the start of injection of the contrast agent (containing the same initial number of microbubbles) by 10.0 seconds, the predicted number of microbubbles and associated number of ETs would be reduced by a factor of 5.3× due to the disappearance of microbubbles, thereby resulting in the number of microbubble induced ET detected in the middle cerebral artery (MCA) using TCD of only 8 ETs corresponding to a very small or Grade I shunt conductance.

By way of a second example illustrating the effect of the agitated saline mixture used and for the case of an actual Medium or Grade III shunt using agitated 80% saline/10% air/10% blood mixture, assume the number of microbubble-induced ETs detected in the middle cerebral artery (MCA) using TCD for a subject is 70 ETs corresponding to a medium or Grade III shunt for the case in which the operator injected the contrast agent immediately after the last of 10 agitation cycles. However, if the operator alternatively used an agitated 90% saline/10% air mixture and again injected the contrast agent immediately after the last of 10 agitation cycles, the predicted number of microbubbles and associated number of detected ETs would be reduced correspondingly by a nearly twelve-fold factor due to the much smaller number of generated microbubbles in the 10 ml injected saline/air contrast agent. As a consequence, the measured the number of microbubble-induced ETs detected in the middle cerebral artery (MCA) using TCD in combination with an agitated saline/air mixture would be only 6 ETs corresponding to a very small or Grade I shunt conductance.

In summary, prior art Transcranial Doppler methods for attempting to quantify the conductance of a right-to-shunt into categories of Grade I (Very Small), Grade II (Small), Grade III (Medium) and Grade IV (Large) are unavoidably limited by significant variations in the numbers of microbubbles contained in the manually prepared and injected bolus of contrast agent even when the injected bolus size is maintained at a consistent volume of 10 ml. This unavoidable limitation becomes even more important for determining the residual conductance of right-to-left shunts after medical interventions to close or "seal" a right-to-left shunt such as atrial septal defect (ASD) or a patent foramen ovale (PFO).

For example, multiple clinical studies have demonstrated the benefits of percutaneous PFO closure with regard to [a] the reduction in occurrence of primary or secondary stroke and/or [b] the reduction or complete cessation of migraine attacks. However, most of the prior clinical trials fail to reach the expected threshold of improvement with statistical significance. Clinical studies have consistently reported residual or recurring shunt levels ranging from 9% to 40% within one year following assumed PFO closure during a percutaneous procedure. It is essential that PFO closure be achieved to the greatest possible extent, even if it requires some period of time post-closure to affect the complete closure of the PFO. During this post-closure sealing period, depending on the detected level of residual shunt conductance, anticoagulant therapy may be indicated to minimize the possibility of cerebrovascular accidents and/or minimizing the frequency and severity of migraines. However, due to the risks of anticoagulant therapy (e.g., hemorrhagic stroke and other internal bleeding complications), anticoagulant therapy with drugs such as warfarin should only be administered if the shunt conductance is sufficiently high to warrant such medical therapy. Likewise, this strategy necessarily requires ongoing monitoring of the patient following closure to determine when prophylactic anticoagulant therapy can be terminated.

However, as seen in the examples presented above, the number of microbubbles contained in the injected bolus of contrast agent can vary by factors of at least seventeen-fold (based on the measured average number of generated microbubbles per cubic millimeter) depending on the agitated saline composition, agitation technique and delay between the last agitation cycle and the start of the injection of the contrast agent into the venous blood circulation of the subject. If the variation in the number of microbubbles generated relative to the average number of microbubbles generated for 63% of the population, the number of microbubbles contained in the injected bolus of contrast agent can vary by factors of more than fifty-fold. Consequently, there is currently no current method for accurately quantifying the conductance of a right-to-left shunt, either prior to or following the percutaneous closure of a right-to-left shunt based on the unknown and significantly varying number of microbubbles contained in the injected bolus of contrast agent, even when the same operator and same agitated saline composition is used for a TCD measurement of shunt conductance.

In addition to the unknown and significantly varying number of microbubbles contained in the injected bolus of contrast agent, there are other factors that can affect the measured number of ETs using the TCD method. These other factors can cause a significant variation in the numbers of detected ETs for a given subject and shunt conductance, even if the number of microbubbles in the injected contrast agent was accurately known and/or controlled. One of these other factors is the adequacy of the provocative maneuver used to briefly increase the pressure in the right atrium to a level that is higher than the pressure in the left atrium. Normally, the localized blood pressure within the left atrium is higher than the right atrium. By way of example, during normal activities that do not involve any provocations such as exertion, straining or coughing, the presence of a right-to-left shunt will result in blood flow, if any, only from the left atrium of the heart to the right atrium of the heart and, accordingly, pose no risk of embolic ischemia since there is no blood flow directly from the right atrium to the left atrium across the atrial septum. However, during provocative activities such as lifting, straining during defecation, physical sports, coughing and scuba diving, the pressure in the right atrium can briefly become larger than the pressure in the left atrium, thereby allowing a portion of the venous blood flowing through the right atrium to briefly flow directly from the right atrium to the left atrium, thereby circumventing the filtering benefit provided by the lungs. Under the conditions of such provocations, any embolus or emboli (viz., tiny blood thrombus or thrombi) in the right atrium during the period of a positive right-to-left atrial pressure gradient can be transported directly to the left atrium. Once in the left atrium, the embolus or emboli can follow any of the normal arterial circulatory pathways which include pathways leading to the brain or the coronary arteries of the heart. Those pathways allowing any embolus or emboli to reach the brain or heart can lead to stroke or heart attack, respectively.

Several types of provocative maneuvers have been reported that can create the required right-to-left pressure gradient to purposely induce the flow of an injected indicator or contrast agent through a right-to-left shunt, if present. Alternative provocative maneuvers include the Valsalva maneuver, Valsalva strain and coughing. The most widely used type of Valsalva maneuver is a breathing procedure involving the following three-steps: [1] inspiration (i.e., deep breath) to fill the lungs with air, [2] generation of exhalation pressure to a predetermined pressure level of about 40 mm Hg into a closed mouthpiece (usually incorporating a pressure sensing device) for a minimum period of five seconds and [3] abrupt release of exhalation pressure followed by normal breathing. Published clinical studies involving humans have demonstrated that a Valsalva maneuver performed according to the above three steps provides the most consistent method for inducing the right-to-left pressure gradient required to induce a temporary blood flow through any right-to-left shunt (e.g., PFO) that may be present in the heart and thereby reveal the presence of a right-to-left shunt by any of the aforementioned detection methods. These published clinical studies also have confirmed that the right-to-left pressure gradient required to induce blood flow across a shunt (if present) [a] only starts upon the release or end of the Valsalva maneuver and [b] only persists for two or three heart beats or about two to three seconds following the Valsalva release. Consequently, it is important that the release or end of the exerted exhalation pressure occurs when the contrast agent arrives in the right atrium of the heart, since the right-to-left pressure gradient persists for only two to three seconds beyond the release of the Valsalva exhalation pressure. Further background on provocative maneuvers including Valsalva maneuvers and coughing maneuvers is found in the following articles: [a] Pfleger, S. et al. Hemodynamic Quantification of Different Provocation Maneuvers by Simultaneous Measurement of Right and Left Atrial Pressure: Implications for the Echocardiographic Detection of Persistent Foramen Ovale. European Journal of Echocardiography 2001; 2: 88-93, [b] Dubourg O, et al., Contrast echocardiographic visualization of cough-induced right-to-left atrial shunt through a patent foramen ovale. Journal of American College of Cardiology 1984; 4: 587-594 and [c] Droste D W, et al., Contrast Transcranial Doppler ultrasound in the detection of right-to-left shunts: comparison of different procedures and different contrast agents. Stroke 1999; 30:1827-1832.

In addition to the critical timing of the release of the Valsalva exhalation pressure that is coincident with the time when an injected contrast agent arrives in the right atrium, it is also important to account for the differences in transit time between the site of injection (e.g., antecubital vein fossa in the arm) and the right atrium. This transit time is critical since the contrast agent needs to arrive at right atrium during the brief two to three second period that the right-to-left pressure gradient persists (immediately after the release of the Valsalva maneuver) in order to cross directly into the left atrium during that brief period. A further complication confronting methods employing contrast agent based shunt detection methods is the variability in the transit time due to differences in the venous volume in the pathway between the antecubital vein and the right atrium associated with subjects of varying size. Even if the contrast agent and flushing solution is injected at a nominally constant rate, the transit time between the antecubital vein and the right atrium can vary by as much as three seconds or more due to vascular differences as well as levels of cardiac output between subjects being tested.

In order to compensate for known transit time differences, it is advantageous to release the Valsalva maneuver to induce a positive right atrial-to-left atrial pressure gradient at the precise time when the contrast agent substantially arrives and fills the right atrium. If the contrast agent arrives more than several seconds before the release of the Valsalva maneuver and the associated creation of the essential right-to-left pressure gradient, then most or all of the contrast agent will proceed along the normal pathway through the lungs and into the left atrium since the right-to-left shunt will effectively be "closed" when the contrast agent arrives. As a consequence, any right-to-left shunt that may be present may not be detected resulting in a false negative shunt test result. Likewise, if the contrast agent arrives too late relative to the release of the Valsalva exhalation pressure, the essential right-to-left pressure gradient will have ended and consequently essentially all of the contrast agent will proceed along the normal pathway through the lungs and into the left atrium again resulting in a negative shunt test result.

In addition to achieving the correct timing of the release of the Valsalva maneuver coincident with the arrival of the contrast agent in the right atrium, the ability to accurately detect the presence of a right-to-left shunt in the heart also depends on performing a provocative maneuver of both adequate intensity (viz., exhalation pressure of at least 40 mm Hg, preferably at least 40 mm Hg) and adequate duration (viz., exhalation exertion for at least 5 seconds).

By way of example, a system and method for measuring exhalation pressure to determine abdominal pressure surrounding the bladder is disclosed by de Menezes in U.S. Publication Number US 2010/0234758. The system and method includes a pressure monitor with display, tubing extending from the pressure monitor to a mouthpiece and a mouthpiece. The subject exhales into the mouthpiece and the exhalation pressure level is displayed. Other methods currently used in the conduct of Valsalva maneuvers include attaching a length of tubing to a pressure gauge or mercury manometer. The patient exhales into the tube and the exhalation pressure is dynamically displayed.

Both of the above methods allow the exhalation pressure to be dynamically measured. As stated above, it is essential that the provocative maneuver be adequate to create a positive right-to-left atrial pressure gradient sufficient to induce blood flow directly from the right atrium to the left atrium (in the event a right-to-left cardiac shunt is present). In addition, it is also essential that the contrast agent arrives in the right atrium during the brief 2 to 3 second period when the positive right-to-left pressure gradient persists so that indicator may traverse the atrial wall (septum) and reveal the presence of a right-to-left shunt. The timing of the arrival of the contrast agent in the right atrium is critical since the time period during which the requisite right-to-left pressure gradient persists is less than about two seconds. In this regard, also see Karttunen, V., et al. Dye Dilution and Oximetry for Detection of Patent Foramen Ovale. Acta Neurol Scand 1998; 97:231-236.

As stated above, the accurate quantification of the conductance of a right-to-left shunt is important to identifying subjects at risk of an ischemic stroke, both a first stroke as well as recurrent strokes caused by the passage of emboli through a patent right-to-left shunt, emboli that would otherwise have been trapped and filtered from the blood stream as a result of the normal flow of blood through the vasculature of the lungs. In addition to minimizing the risk of strokes, there are other significant adverse consequences of right-to-left shunts, especially larger right-to-left shunts (e.g., PFOs and ASDs) exhibiting higher shunt conductances. By way of example of other adverse consequences, the association between migraineurs with aura and ischemic stoke has been reported to be statistically significant based on a six year follow-up of 459 subjects that were 45 years or older (see Androulakis, X., et al., Ischemic Stroke Subtypes and Migraine with Visual Aura in the ARIC Study. Neurology 2016; EPub Nov. 9, 2016). As another example, a report including 20 observational studies involving 1,194 subjects, 10% to 83% reported complete cessation of migraine and 14% to 83% reported reduction in migraine symptoms (see Tariq, N., et al., Patent Foramen Ovale and Migraine: Closing the Debate—A Review. Headache 2016; 56 [3]: 462-478). In the PREMIUM Trial of 220 subjects with 117 receiving PFO closure, 10.8% of migraineurs with aura experienced complete remission of migraine headaches following PFO closure while only 1.5% experienced complete remission without PFO closure (see Reisman, M., et al., Migraine Reduction after Transcatheter Closure of Interatrial Septal Defects: Another Brick in the Wall? Journal of Structural Heart Disease 2016; 2 [5]: 231-233). In yet another example, the PRIMA Trial showed a significant reduction in migraine symptoms during 12-month follow up after PFO closure compared to medical treatment alone (Tarantini, G., et al., Patent Foramen Ovale Closure and Migraine Time Course: Clues for Positive Interaction. Int. Journal of Cardiology 2015; 195:235-236). In yet another clinical trial, it has been reported at three months after PFO closure that 40% of patients with only aura had complete resolution of symptoms while 25% of migraineurs with aura had complete resolution of symptoms (see Khessali, H., The Effect of Patent Foramen Ovale Closure on Visual Aura without Headache or Typical Aura with Headache. Journal of American College of Cardiology: Cardiovascular Interventions 2012; 5: 682-687). In yet another clinical trial in which complete PFO closure was confirmed, 15 of 16 patients experienced complete remission of migraine symptoms after closure (see Yoon, J., et al., Intermediate and Long-Term Results of Transcatheter Closure of Patent Foramen Ovale Using Amplatzer Patent Foramen Ovale Occluder: One Case of Pulmonary Embolism Irrespective of Patent Foramen Ovale Closure. Korean Circulation Journal 2011; 41: 356-362).

In addition to minimizing the risk of stroke and debilitating affects of severe migraine, clinical studies have also confirmed the adverse neurological impact of the cardiac shunt-related emboli burden on an otherwise asymptomatic population. The results of clinical studies indicate that a significant cause of dementia in the elderly population may be due to the presence of a right-to-left shunt since the cumulative effect of subclinical or silent microinfarcts appears likely to be a principal cause of progressive dementia and possibly even Alzheimer's Disease. The dementia and Alzheimer's Disease syndrome is now considered by many clinicians to be a sufficient reason to prophylactically close known PFOs assuming closure can be safely and effectively accomplished. In this regard, see [a] Bang, O., et al., Patent Foramen Ovale and Stroke—Current Status. Journal of Stroke 2015; 17(3): 229-237, [b] Hassell, M., et al., Silent Cerebral Infarcts Associated with Cardiac Disease and Procedures. Nature Reviews Cardiology 2013; 10: 696-706 and [c] Purandare, N., et al., American Journal of Psychiatry 2012; 169: 300-308.

The detection of the presence of a clinically significant right-to-left shunt in a patient routinely enables the attempted closure of the shunt using one of a number of alternative transcatheter closure devices. However, clinical trials have demonstrated that complete closure of the identified right-to-left shunt often is not achieved, especially in the first three to twelve months after closure, resulting in residual shunting. By way of example of the differing levels of achieved closure with alternative closure devices, the level of residual shunting after ASD closure in 217 patients at 12 months post closure was clinically significant with 40%, 22% and 9% residual shunting observed upon post-closure examination using TEE for CardioSEAL/STARFlex, Helex and Amplatzer closure devices, respectively (see Zdradzinski, M., et al., Contributors TO and Impact of Residual Shunting After Device Closure of Atrial Septal Defects. American Heart Journal 2016; 177: 112-119). In yet another example, a significant number of recurrent and residual right-to-left shunts were observed in a 120 patient cohort using the TCD method at an average of five years after PFO closure with 17% exhibiting residual shunting and 29% exhibiting recurrent shunting, i.e., the residual shunting decreased significantly and then subsequently increased significantly suggesting failure of the closure device (see Cheli, M., et al., Recurrent and Residual Shunts After Patent Foramen Ovale Closure: Results from a Long-Term Transcranial Doppler Study. Journal of Interventional Cardiology 2015; 28: 600-608).

The above examples of the prevalence of residual shunting, as well as recurrent shunting, extending for post-closure periods of a year or more, confirm the need for an accurate method for quantifying the conductance of residual and recurrent shunting after the intended closure. The accuracy of the post-closure method for quantifying the conductance of a residual or recurrent shunt is important for three reasons. First, the level of residual or recurrent shunting following "closure" guides the clinician's selection of anti-coagulant therapy, if needed, and the duration of its use following closure. Once the conductance of the shunt following closure is confirmed to have been sufficiently reduced (e.g., reduced from a large Grade IV shunt to a very small Grade I shunt), then the use of high risk anticoagulants such as warfarin can be terminated and replaced with, at most, aspirin therapy. Second, the level of residual or recurrent shunting following "closure" allows the assessment of the efficacy of the closure device and the suitability of its continued clinical use.

Third, the level of residual or recurrent shunting following "closure" enables the conduct of meaningful clinical trials so that the inability to achieve the expected outcome (e.g., reduction in the occurrence of strokes or migraine symptoms) can be interpreted based on extent to which shunt closure was actually achieved. In spite of the demonstrated sensitivity to detect the presence of a right-to-left shunt, prior art Transcranial Doppler apparatus, systems and methods are incapable of accurately quantifying the conductance of right-to-left shunts. This inherent limitation is the consequence of multiple and uncontrolled operator dependent functions including [a] the interpretation of ultrasound images of embolic tracks (currently performed manually and subject to individual interpretation), [b] the accurate positioning of ultrasound traducers over the Middle Cerebral Artery on one or both sides of the subject's head adjacent to the targeted intracranial arteries, [c] the timing of the arrival of the injected agitated saline ultrasound contrast agent (i.e., microbubble mixture) in the right atrium relative to the timing of the Valsalva Maneuver release and [d] the very large (20× or more) variability in number of microbubbles injected due to the operator's preparation method and variable delays before injection causing microbubbles to collapse since their half-life has been measured to be in the range from about 4 to 5 seconds depending on the contrast agent composition.

In summary and in view of the fact that over 20% of the adult population has a right-to-left shunt, the capability to accurately quantify the conductance of a right-to-left shunt is clinically beneficial for a number of reasons as described above. The clinical benefits of providing an accurate method for quantifying the conductance of a right to left shunt include identifying subjects whose right-to-left shunt is sufficiently large to warrant intervention with transvascular closure or anticoagulant therapy to minimize [a] the risk of initial or recurrent ischemic strokes, [b] the frequency and severity of migraine headaches and [c] the risk and severity of dementia and Alzheimer's Disease. In addition, providing an accurate method for quantifying the conductance of a right-to-left shunt is essential for ongoing clinical follow-up and guiding medical therapy following transcatheter closure of a right-to-left shunt as well as characterizing the efficacy of alternative closure devices and method used.

An object of the present disclosure is therefore to provide a Transcranial Doppler (TCD) ultrasound method, apparatus and system to accurately measure the conductance of a right-to-left shunt with a high level of repeatability. In order to achieve the conductance measurement accuracy and repeatability required, it is an object of the present disclosure to incorporate a method, apparatus and system to detect when the contrast agent substantially arrives in the right atrium of the heart. Another object of the present disclosure is to provide a method, apparatus and system to assure a Valsalva maneuver whose exhalation pressure level and duration are within predetermined limits (e.g., a pressure of at least 40 mm Hg and at least 5.0 seconds in duration).

Another object of the present disclosure is to provide a method, apparatus and system to automatically induce the release (i.e., end) of the Valsalva maneuver when the arrival of the contrast agent in the right atrium is detected. Yet another object of the present disclosure is to incorporate a controlled leak in the exhalation mouthpiece so that the patient creates the required Valsalva maneuver pressure using their diaphragm and not their cheek muscles. The creation of pressure using only the cheek muscles will not create the hemodynamic conditions necessary to effect a right-to left pressure gradient. A further object of the present disclosure is to provide a mouthpiece component that can be manufactured at sufficiently low cost to enable its single use thereby avoiding cross-contamination and pathogen transfer between patients. Yet another object of the present disclosure is to incorporate a method, apparatus and system to automatically count the number of microbubbles contained in a sampled portion of the agitated saline/air/blood mixture so that the number of embolic tracks measured using Transcranial Doppler ultrasound can be adjusted according to the total number of microbubbles injected estimated using a sampled volume of contrast agent. Still yet another object of the present disclosure is to incorporate a method, apparatus and system to automatically determine the number of embolic tracks using a software algorithm based on [a] the number of countable embolic tracks and/or [b] an ultrasound signal intensity as an equivalent metric for the number of microbubbles transported within the targeted intracranial artery, thereby eliminating the time consuming and user dependent manual counting methods currently use to analyze the ultrasound spectra generated by Transcranial Doppler apparatus and systems.

SUMMARY OF THE INVENTION

The present disclosure is addressed to a Transcranial Doppler apparatus, system and method for the detection and the quantification of the conductance of right-to-left cardiac shunts (also referred to hereinafter as a "shunt test"). This instrumentation includes a first set of one of more Doppler ultrasound transducer arrays disposed on the surface of the skull of the subject in close proximity to the middle cerebral arteries located with the transducer arrays positioned at one or both hemispheres of the skull. The one or more first Doppler ultrasound transducer arrays are supported and maintained in a predetermined position by an external apparatus such as a headband externally and temporarily secured around the head of the subject. The positions of the first set of one or more Doppler transducer arrays are adjusted to maximize the level of the reflected Doppler ultrasound signals emanating as a result of the velocity of the blood flowing through one or both of the targeted middle cerebral arteries. The reflected Doppler ultrasound signals are visually and continuously displayed on a monitor during the initial transducer array positioning procedure of one or more Transcranial Doppler transducer arrays.

The instrumentation also includes a second Doppler ultrasound transducer placed on the surface of the precordium (i.e., anterior chest wall) over the heart of the subject to receive reflected ultrasound signals originating in the right atrium of the heart. Positioning of the precordial Doppler ultrasound transducer array includes the step of injecting a bolus of agitated saline/air mixture containing microbubbles into a peripheral vein (e.g., antecubital vein) and observing the reflected Doppler ultrasound signals to confirm that the precordial Doppler ultrasound transducer is properly positioned over the right side of the heart. Once the precordial Doppler ultrasound transducer array is properly positioned in close proximity to the right side of the heart, the transducer array is removably secured to the skin surface of the subject, for example, with adhesive tape. The reflected ultrasound signals emanating from the injected echogenic air-filled microbubbles entrained in the venous blood flowing into the right atrium are detected using the precordial Doppler transducer array. The reflected Doppler ultrasound signals are visually and continuously displayed on the monitor during the initial precordial Doppler transducer array positioning procedure.

The present disclosure includes an apparatus, system and method to guide the performance, monitor the characteristics, and grade the adequacy of a provocative Valsalva maneuver during a Transcranial Doppler test procedure. According to the teachings of this disclosure, the adequacy of the exhalation pressure exerted by the subject is achieved by displaying the exerted exhalation pressure level on the screen of the monitor within the view of the subject, highlighting the minimum threshold pressure required to achieve an acceptable Valsalva maneuver. The monitor records the exerted exhalation pressure as a function of time during the period of the Valsalva maneuver. The recorded exhalation pressure as a function of time is analyzed and graded based on predetermined minimum Valsalva maneuver requirements (e.g., minimum exhalation pressure level during maneuver, duration of exerted exhalation pressure, absence of any interruptions to exerted exhalation pressure during period of maneuver). If the resulting grade indicates that the subject or patient performed an adequate Valsalva maneuver, then the result of the test for the detection and quantification of the conductance a right-to-left cardiac shunt is displayed as a valid test result. If the exhalation pressure level and duration does not meet the predetermined minimum criteria (e.g., minimum exhalation pressure minimum and duration of exerted exhalation pressure), then the operator is advised that the shunt test just completed is invalid and needs to be repeated due to an inadequate Valsalva maneuver.

As discussed above, the ability to detect the presence of most right-to-left cardiac shunts requires that the subject perform a provocative Valsalva maneuver having an adequate exerted exhalation pressure level (viz., an exhalation pressure of at least 37 mm Hg, preferably at least 40 mm Hg) and of adequate duration (viz., adequate exhalation pressure exertion for at least 5 seconds). An adequate Valsalva maneuver is required to achieve the essential right atrium-to-left atrium pressure gradient that occurs immediately after the release of the exhalation pressure (i.e., the release of the Valsalva maneuver) and causes blood to flow directly from the right atrium to the left atrium in the event a right-to-left shunt (e.g., a patent foramen ovale) is present.

The present disclosure is also addressed to an apparatus, system and method to precisely control the release (i.e., end) of the Valsalva maneuver upon the arrival of the agitated saline contrast agent (e.g., agitated saline/air/blood mixture or agitated saline/air mixture) in the right atrium. Alternatively, other sterile isotonic aqueous solutions suitable for IV injection may be used in place of an isotonic saline solution, for example, sterile Ringers isotonic solution. According to the teachings of this disclosure, the instrumentation also includes a mouthpiece assembly that comprises an ergonomic tube for insertion into the mouth, a tubular body that contains a movable shuttle that alternately isolates and exposes vent holes, an extension tube that provides hydraulic communication between the mouthpiece tubular body and quick-disconnect fitment to enable removable attachment of the extension tubing to the mating fitment at the front panel of the monitor. The tubular body of the mouthpiece assembly includes baffle plates to direct the exhaled air away from the face of the patient when the vents are exposed at the end of the Valsalva maneuver and air is rapidly expelled from the patient's lungs. The movable shuttle component includes a pair of O-rings in combination with a biocompatible lubricant on the inner walls of the tubular body to minimize the static and dynamic friction and enable the movement of the shuttle when a negative pressure (i.e., vacuum) or positive pressure is applied by the solenoid-driven vacuum/pressurization assembly described herein.

A solenoid-driven vacuum/pressurization assembly is provided inside the monitor that comprises a tubular vacuum/pressurization body that contains a movable piston, a compression spring (biasing member) to return the piston to its starting position after de-energizing the solenoid, an electronically actuated solenoid, a pull rod connected between the solenoid plunger and the piston and tube support members at either end of the tubular vacuum/pressurization body to enable mounting to an interior frame within the monitor. The internal tubing located between the front panel fitment and the solenoid-driven vacuum/pressurization assembly includes a pressure sensor to continuously measure the exhalation pressure exerted by the patient during the Valsalva maneuver.

The shuttle within the tubular body of the mouthpiece assembly incorporates a small diameter hole that provides [a] a sufficiently large flow factor to enable pressure equalization and dynamic exhalation pressure measurement and [b] a sufficiently small flow factor to enable negative pressures (i.e., vacuum) or positive pressures (i.e., pressurization) rapidly created in solenoid-driven vacuum/pressurization assembly to induce rapid movement of the shuttle within the mouthpiece assembly from the "vents closed" position during the period of the Valsalva maneuver to the "vents open" position at the moment of intended Valsalva release.

A microprocessor within the controller of the monitor receives an input via an analog/digital converter from a precordial Doppler ultrasound transducer signal analysis algorithm that detects the arrival of the microbubble-filled contrast agent in the right atrium of the subject's heart. When the arrival of the microbubble-filled contrast agent in the right atrium of the subject's heart is detected, a command is issued to a digital/analog converter to effect the actuation of a solenoid (e.g., a pull-type solenoid). The actuation of the solenoid, which is securely connected to the piston within the solenoid-driven vacuum/pressurization assembly, causes the piston to rapidly retract thereby rapidly creating a partial vacuum within the volume comprising the internal tubing, the extension tubing and the mouthpiece assembly. The partial vacuum created within the mouthpiece assembly causes the shuttle to rapidly retract from a "vents closed" proximal position to "vents open" distal position within the tubular body of the mouthpiece assembly.

As a consequence, within a very brief period (e.g., 0.05 seconds) from the actuation of the solenoid valve, the opening of the vents forces the release (end) of the Valsalva maneuver at the desired time. Under these preferred conditions, the patient is forced to rapidly exhale since there is no longer any pressure resistance afforded by the mouthpiece assembly. In order to accommodate the repetition of Transcranial Doppler tests for a subject at the completion of the first test involving a provocative maneuver and within a brief period after the shuttle is withdrawn and exposes the vents (e.g., 5 seconds), the solenoid is de-energized and a compression spring within the tubular vacuum/pressurization body (compressed under the force of the pull-type solenoid) forces the piston to rapidly return to its original position. This rapid return to the piston's original position pressurizes the volume comprising the internal tubing, the extension tubing and the mouthpiece assembly. As a consequence, the shuttle within the mouthpiece assembly rapidly returns to its original position, which corresponds to the vents being closed. At this stage, the mouthpiece assembly is ready for one or more subsequent test procedures involving this subject.

The first Transcranial Doppler test procedure is preferably performed while the subject remains at rest (i.e., a test performed without an accompanying Valsalva maneuver). Such a right-to-left shunt test while the subject is at rest serves to reveal the presence of a very large shunt, a shunt so large that the right atrium-to-left atrium pressure gradient induced by the release of a Valsalva maneuver is not necessary to permit the injected microbubble-containing contrast agent to be transported directly from the right atrium to the left atrium, as revealed by microbubbles flowing in the intracranial arteries during the Transcranial Doppler (TCD) test procedure. A first TCD procedure while the subject is at rest also enables the measurement of the transit time from the detected start of contrast injection (i.e., injection start time), as described below in connection with the microbubble counting or alternative ultrasound signal intensity measurement procedure, to the time of arrival of the contrast agent in the right atrium, as detected by the precordial Doppler ultrasound transducer and associated signal analysis. The measured transit time from the detected start of injection of the contrast agent (e.g., agitated saline/air/blood mixture or agitated saline/air mixture) to the arrival of the contrast agent in the right atrium of the heart is recorded and then used to determine when the audible cue is to be issued to the operator by the monitor to prompt the start of the injection of the contrast agent following the detected start of the Valsalva maneuver by the subject.

Embodiments of the present disclosure are further directed to a method of manufacture and assembly of the mouthpiece assembly that may be cost-effectively provided in a sterile condition for a single test session by a patient and then the mouthpiece assembly is discarded. The single use of the mouthpiece assembly is preferred due to the necessary movable shuttle component within the mouthpiece assembly, the benefit to providing a lubricant on the interior of the tubular body of the mouthpiece assembly and the inaccessibility of the interior portions of the mouthpiece assembly to enable essential cleaning and sterilization of the mouthpiece assembly between uses.

The present disclosure is also addressed to an apparatus, system and method to estimate the total number of microbubbles contained within the contrast agent at the moment of injection into the venous blood of the subject. The total number of microbubbles contained within the contrast agent at the moment of injection is estimated by first measuring the actual number of microbubbles contained within an optically transparent microbubble counting cell. The microbubble containing contrast agent, after being prepared by repeated cyclic injection of a saline/air/blood mixture or agitated saline/air mixture between two syringes or other agitation method, is promptly injected into a catheter leading to a venous access needle placed in the subject's vein (e.g., antecubital vein). Alternatively, other sterile isotonic aqueous solutions suitable for IV injection may be used in place of an isotonic saline solution, for example, sterile Ringers isotonic solution. An optically transparent microbubble counting cell is positioned along the length of the catheter between the contrast agent containing syringe and the venous access needle placed in the subject's vein so that the process of injecting the contrast agent fills the interior chamber of the optically transparent microbubble counting cell. A digital image sensor is removably attached to a flat, optically transparent microbubble counting cell over a confined width and length of microbubble counting zone. The microbubble counting cell incorporates a thin interior cavity (e.g., 0.1 mm) to permit direct imaging and high-definition resolution of microbubbles once the contrast agent injection step, lasting about two seconds, is completed. A predetermined volume, referred to hereinafter as a microbubble counting zone (e.g., 1.0 mm×1.0×an interior cell thickness of 0.1 mm) within the optically transparent microbubble counting cell, as seen in the field of view of a digital image sensor (e.g., a miniature complementary metal oxide semiconductor or CMOS digital image sensor similar to digital image sensor contained in smart phones), is recoded recorded and digitally analyzed to determine the number of microbubbles present in this predetermined volume. Regarding the digital analysis of images of the microbubble counting zone containing a multiplicity of microbubbles, see De Costa, L., Digital Image Analysis of Blood Cells. Clinical Laboratory Medicine 2015; 35: 105-122. The image analysis of the recorded image of the microbubbles may be aided by the addition of laser etched grid lines within the boundaries of the microbubble counting zone. This number of microbubbles determined by an analysis of the imaged test cell volume (e.g., 0.1 cubic mm) then is used to ratiometrically derive the corresponding number of microbubbles within the known volume of injected contrast agent (e.g., 10 cubic cm or 10 ml).

A multilevel grading scale (e.g., five levels of detected embolic tracks) for the conductance of a wide range right-to-left shunt conductances is established for a standard number of microbubbles (e.g., 1,500,000 bubbles in the injected contrast agent). Based on the actual number of microbubbles injected, the measured number of detected embolic tracks is adjusted by multiplying the measured number of embolic tracks by the ratio of the actual (derived) number of microbubbles relative to the established standard number of microbubbles.

The optical characteristics of the contrast agent (e.g., level of light transmission) also allows the digital image sensor attached to the microbubble counting cell to detect the start of the injection of the contrast agent as the contrast agent enters and fills the optically transparent microbubble counting cell. The time of occurrence of the start of injection of the microbubble-filled contrast agent is combined with the detected time of arrival of the microbubble-filled contrast agent in the right atrium, during a first at-rest shunt test, to accurately measure the transit time of the contrast agent between the point of injection and the arrival in the right atrium. This measured transit time is then used in subsequent TCD tests in which the subject performs a Valsalva maneuver, as described above, to detect and quantify the conductance of a right-to-left shunt, if present.

The present disclosure also is addressed to apparatus, system and method for [a] measuring the Doppler ultrasound signals reflected from arterial blood flowing in a targeted length intracranial arteries over a predetermined time interval following the arrival of contrast agent in the right atrium, [b] analyzing Doppler derived velocity spectrum of detected microbubbles using spectral analysis methods (e.g., Fast Fourier Transform analysis method) to determine the distribution of peak velocities around an average peak velocity, [c] computing the power or amplitude of the signals for a selected range of peak velocities reflected from microbubbles within the blood flowing in the targeted intracranial arteries in a range spanning a derived average peak velocity and [d] translating the derived power or amplitude of the reflected Doppler signals associated with the microbubbles flowing in intracranial arteries into a corresponding number of detected microbubbles (e.g., detected number of embolic tracks).

Other objects of the disclosure will be obvious and will, in part, appear hereinafter. The disclosure, accordingly, comprises the method, system and apparatus possessing the construction, combination of elements, arrangement of parts and steps, which are exemplified in the following detailed description. For a fuller understanding of the nature and objects of the disclosure, reference should be made to the following detailed description taken in connection with the accompanying drawings.

BRIEF DESCRIPTION OF THE DRAWINGS

In addition to the features mentioned above, other aspects of the disclosure will be readily apparent from the following descriptions of the drawings and example embodiments, wherein like reference numerals across the several views refer to identical or equivalent features, and wherein:

FIG. 5A is a side view of a shuttle component used in a mouthpiece assembly;

FIG. 5B is a cross-sectional view of a shuttle component used in a mouthpiece assembly;

FIG. 5C is a perspective view of a shuttle component used in a mouthpiece assembly, showing a proximal end of the shuttle;

FIG. 5D is a perspective view of a shuttle component used in a mouthpiece assembly, showing a distal end of the shuttle;

FIG. 8A is a cross-sectional view of an example piston used in a vacuum/pressurization subassembly;

FIG. 8B is a perspective view of an example piston used in a vacuum/pressurization subassembly;

FIG. 9 is a perspective view of an example vacuum/pressurization tube used in a vacuum/pressurization subassembly;

FIG. 10A is a cross-sectional view of an example first tube support end plate used in a vacuum/pressurization subassembly;

FIG. 10B is a perspective view of an example first tube support end plate used in vacuum/pressurization subassembly;

FIG. 11A is a cross-sectional view of an example second tube support end plate used in vacuum/pressurization subassembly;

FIG. 11B is a perspective view of an example second tube support end plate used in vacuum/pressurization subassembly;

FIG. 16B is cross-sectional side view of the microbubble counting cell seen in

FIG. 18A-18G combine as labeled thereon to show a flow chart of a procedure associated with an example method of the disclosure for placement of first and second Transcranial Doppler transducer arrays, preparing agitated saline contrast agents, injecting contrast agent into subject, measuring number of microbubbles in a predefined within a microbubble counting cell and performing a Valsalva maneuver as part of a Transcranial Doppler ultrasound based procedure for the detection and quantification of a right-to-left shunt.

The drawings will be described in further detail below.

DETAILED DESCRIPTION OF EXEMPLARY EMBODIMENT

Figure 1:
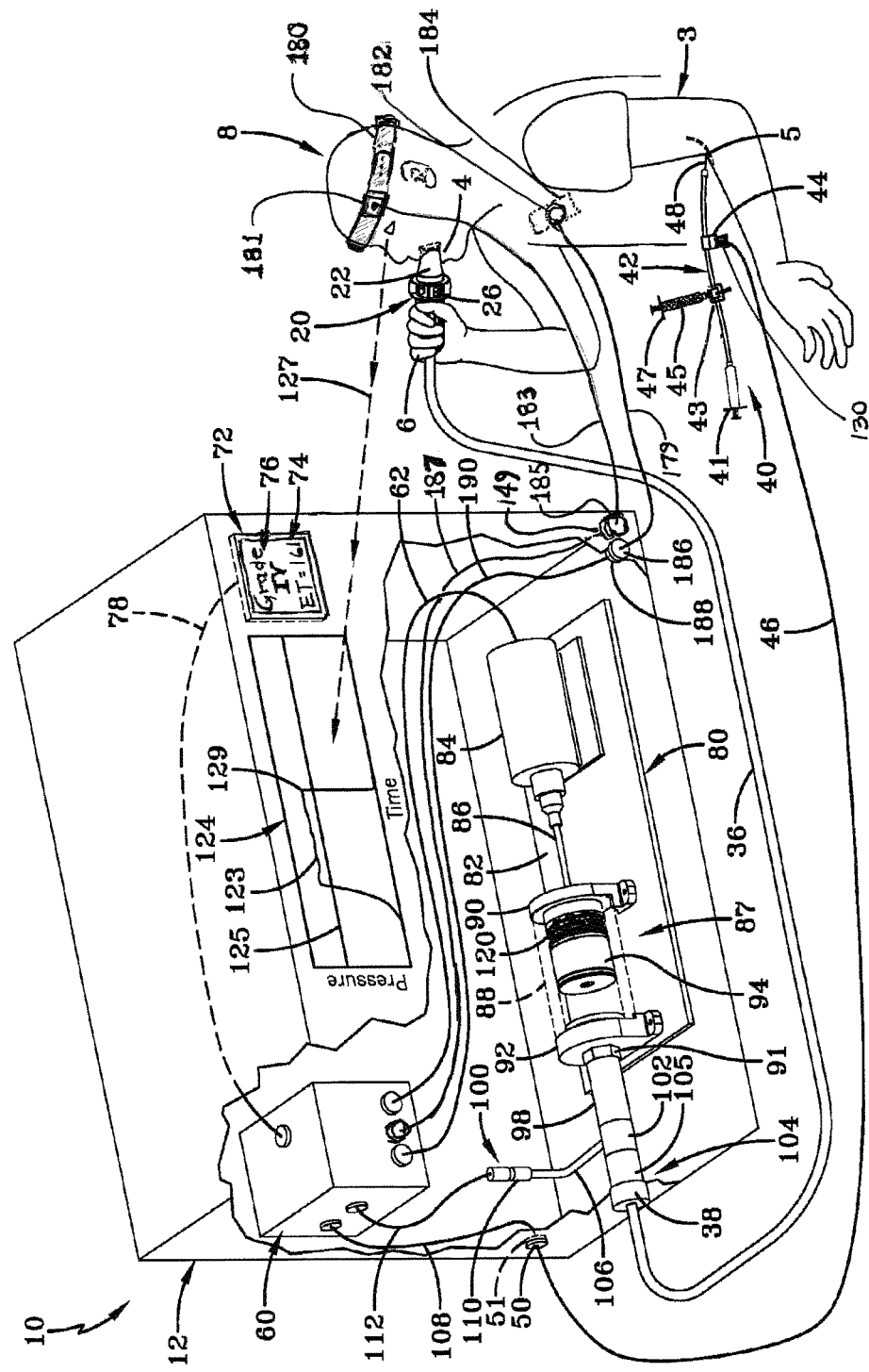
FIG. 1 is a partially sectioned and cut away perspective view, of an example embodiment of a system for the detection and quantification of right-to-left cardiac shunts showing a monitor, first set of Doppler ultrasound transducer arrays positioned at the head of the subject, second Doppler ultrasound transducer positioned on the precordium of the subject, microbubble counting cell and removably attachable digital image sensor, catheter set, mouthpiece assembly for performance of a Valsalva maneuver and apparatus for controlled release of the Valsalva maneuver by a patient being tested for the presence of as well as the conductance of a cardiac shunt using a Transcranial Doppler method.

Referring to FIG. 1, an illustrative embodiment of the present disclosure is described showing the principal components of a system for detecting and quantifying the conductance of a right-to-left shunt using a Transcranial Doppler ultrasound method. The principal components include [a] headband 180 incorporating a first set of Doppler ultrasound transducer arrays 181 for insonation of targeted intracranial arteries (e.g., middle cerebral arteries) in one or both hemispheres of the skull of subject 8, [b] a second Doppler ultrasound transducer 182 positioned on the surface of the precordium of subject 8 to detect the arrival of contrast agent in the right atrium (not shown), [c] catheter set 40 including venous access needle accessing antecubital vein, two syringes 41 and 47 for combining and agitating a mixture of saline, air and the subject's blood as well as a microbubble counting cell 44 and removably attachable digital image sensor (not shown), [d] mouthpiece assembly 20 and solenoid-driven vacuum-pressurization assembly 80 for controlling the performance of Valsalva maneuvers and [e] monitor 10 for displaying exhalation pressure level and providing visual feedback to subject during Valsalva maneuver as well as displaying measured level of right-to-left cardiac shunt conductance at end of test. The measured shunt conductance results as well as the subject's exhalation pressure as a function of time graph for each test are recorded by the monitor and may optionally be printed out on a printer connected directly to the monitor (not shown) or may be printed on a remote printer.

As seen in FIG. 1, with a first set of Doppler ultrasound transducers placed on the head of the subject in the vicinity of the targeted intracranial arteries and a second Doppler ultrasound transducer secured on the chest of the subject adjacent to the right atrium, patient 8 grasps mouthpiece assembly 20 with hand 6 and positions ergonomic tube 22 in his or her mouth 4. By way of example as seen in FIG. 1, patient 8 is performing a Valsalva maneuver as one essential step in the detection of a right-to-left cardiac shunt based on the Transcranial Doppler method.

An example embodiment of a monitor 10 for the detection of a right-to-left cardiac shunt, as seen in FIG. 1, includes a catheter set 40 for injection of a microbubble-containing ultrasound contrast agent 45 into the blood stream of patient 8 at the antecubital vein 5 of the arm 3 of patient 8. Injection of microbubble-containing contrast agent 45 may be achieved by depressing a plunger of a contrast agent syringe 47 containing microbubble-containing contrast agent 45 and attached to flexible catheter 42. By depressing plunger of contrast agent syringe 47, microbubble-containing contrast agent 45 (e.g., liquid volume of 1 to 10 ml) is forced to flow via catheter 42 through a microbubble counting cell 44 to a venous access needle 48 and into the antecubital vein 5 in arm 3 of patient 8.

As the microbubble-containing contrast agent passes through microbubble counting cell 44, it is detected using, by way of example, a measured change in the level of light transmission through the flowing liquid for the case of a microbubble-containing contrast agent 45 that has a lower transmission of light photons than optically clear isotonic saline solution residing in catheter 42 and microbubble counting cell 44 prior to the start of injection of contrast agent 45. Still referring to FIG. 1, prior to the injection of the microbubble-containing contrast agent 45 into the subject's vein, a first syringe 47, is filled with a mixture of saline, air and the subject's blood (e.g., a 10 ml syringe filled 8.0 ml saline, 1.0 ml air and 1.0 ml of the subject's blood withdrawn from the subject's antecubital vein via the indwelling venous access needle). For the case of shunt tests following a first at-rest shunt test, a second syringe 41 is filled with isotonic saline and then its contents are expelled through catheter 42 and through the venous access needle 48 by the operator adjusting the flow path within three-way stopcock 43 to flush all residual contrast agent from within catheter 42 and microbubble counting cell 44 and replace with isotonic saline. The next step, after plunger in second syringe 41 is moved to its most forward position and second syringe is without any void space, the flow path of three-way stopcock 43 is adjusted by the operator so that mixture of saline, air and blood (initially within first syringe 47) can be repeatedly and cyclically exchanged between syringes 47 and 41 to affect the agitation required to create microbubbles. By way of example, the initially filled first syringe 47 containing a saline/air/blood mixture is fully and rapidly expelled into empty second syringe 41 and then the process is immediately reversed and the saline/air/blood mixture is rapidly expelled back into first syringe 47 representing one complete agitation cycle. This process is repeated for at least six complete cycles and preferably ten cycles to produce the microbubble-containing contrast agent 45. Alternatively, the step associated with the withdrawal of blood can be eliminated and the contrast agent 45 may comprise a mixture of only isotonic saline (e.g., 9.0 ml) and air (1.0 ml) that is exchanged between syringes 47 and 41 to create microbubbles. Alternatively, other sterile isotonic aqueous solutions suitable for IV injection may be used in place of an isotonic saline solution, for example, sterile Ringers isotonic solution.

At the completion of the last agitation cycle, the subject is prompted to begin the Valsalva maneuver and three-way stopcock 43 flow path is adjusted by the operator so that the contrast agent 45 contained within syringe 47 can be injected into the subject via catheter 42 and venous access needle 48. Once the exhalation pressure exerted by the subject into mouthpiece assembly 20, as measured by pressure sensor within monitor, exceeds a predetermined minimum threshold pressure (e.g., 40 mm Hg), a timer (not shown) within monitor 10 begins counting down for a predetermined time interval (e.g., 4.0 seconds) based on [a] the requirement for a Valsalva maneuver whose duration is at least 5.0 seconds and [b] the measured transit time for the passage of the injected contrast agent 45 from its injection into the subject's vein until its arrival in the right atrium. Once the predetermined time interval has elapsed, an audible cue is issued to the operator to promptly inject the contrast agent in syringe 47 into the blood stream of the subject via a pathway that includes catheter 42, microbubble counting cell 44 and venous access needle 48.

The detection of microbubble-containing contrast agent 45 in microbubble counting cell 44 by attached digital image sensor is communicated to controller 60 of monitor 10 via a cable 46 that is removably connected to monitor 10 at a connector 50, which is inserted into a receptacle 51 connected to controller 60 via a cable 108.

Still referring to FIG. 1, a cut away view of an enclosure 12 of example monitor 10 reveals controller 60, a solenoid-driven vacuum-pressurization assembly 80 and an internal tubing assembly 100. In one example embodiment of the solenoid-driven vacuum-pressurization assembly 80, a solenoid 84 (e.g., a Pull-Type Tubular Solenoid, Ledex 150, from Johnson Controls, Vandalia, Ohio) is securely attached to a platform 82 and the plunger of solenoid 84 is mechanically coupled to a piston 94 in vacuum/pressurization subassembly 87 with a solenoid pull rod 86.

By way of example, prior to energizing solenoid 84, piston 94 is initially maintained against the inner face of a second tube support end plate 92 at the distal position within a vacuum/pressurization tube 88 due to the force applied by a compression spring 120. When solenoid 84 is energized by a power source (not shown) through controller 60 and an associated cable 62, the plunger within solenoid 84 rapidly retracts, typically within a period of less than 0.1 seconds. Upon the rapid retraction of the plunger (not shown) in solenoid 84, piston 94 rapidly moves to a fully retracted position while contracting compression spring 120 based on the allowable stroke length of the plunger in solenoid 84 and as a result of the pull force applied through solenoid pull rod 86.

The rapid retraction of piston 94 creates a negative pressure within the enclosed air space comprising vacuum/pressurization tube 88, the interior volume of an inner tubing assembly 100, the interior volume of associated extension tubing 36, and the internal volume at distal end of mouthpiece assembly 20. The negative pressure created by rapid withdrawal of piston 94 when solenoid 84 is energized causes a shuttle (not shown) within mouthpiece assembly 20 to be retracted from its starting proximal position to a distal position within a tubular body (not shown), thereby exposing a multiplicity of vent holes 26. The processes involved and the effect of the alternating negative pressure and positive pressure created by operation of the solenoid-driven vacuum/pressurization assembly 80 are described in greater detail in the discussion that follows.

Still referring to FIG. 1, the rapid retraction of the shuttle (not shown) within the mouthpiece assembly 20 results in a low flow resistance pathway between the ergonomic tube 22 in mouth 4 of patient 8 and the surrounding atmosphere external to the mouthpiece assembly 20. The low flow resistance pathway causes patient 8 to rapidly exhaust all of the compressed air in the lungs of patient 8, thereby ending the Valsalva maneuver. Following the retraction of shuttle within the mouthpiece assembly 20, a sufficient time period (e.g., 5 seconds) is provided to ensure both (a) complete expiration by the patient and (b) complete ingress of air into the enclosed air space comprising vacuum/pressurization tube 88, interior volume of inner tubing assembly 100, interior volume of extension tubing 36 via pressure equalization conduit 18. The latter ingress of air provides for the return of the air pressure within this air space to approximately atmospheric pressure. Following this ingress of air over a brief period (e.g., 5 seconds), solenoid 84 within solenoid-driven vacuum/pressurization assembly 80 is de-energized. Upon de-energizing solenoid 84, the magnitude of the pull force previously applied by solenoid 84 on piston 94 though solenoid pull rod 86 becomes zero. The prior retraction of piston 94 also induces contraction of compression spring 120.

When the pull force exerted by solenoid 84 rapidly decreases to zero as solenoid 84 is de-energized, the energy stored in compression spring 120, while in its contracted state, forces piston 94 to rapidly return to its most distal position adjacent to second tube support end plate 92. The rapid return of piston 94 to its distal position, under the force applied by compression spring 120, creates a positive pressure within the enclosed air space comprising vacuum/pressurization tube 88, interior volume of inner tubing assembly 100, interior volume of extension tubing 36 and internal volume at distal end of mouthpiece assembly 20. The positive pressure created by the rapid displacement of piston 94 to its most distal position when solenoid 84 is de-energized causes the shuttle (not shown) within mouthpiece assembly 20 to be displaced from its distal position to a proximal position within tubular body (not shown), thereby once again isolating the multiplicity of vent holes 26 in mouthpiece assembly 20 from the interior of the ergonomic tube 22 in preparation for the performance of a subsequent Valsalva maneuver.

In the above discussion of the cyclic operation of solenoid 84 in conjunction with FIG. 1, a power supply (not shown) within controller 60 applies power to solenoid 84 through power cable 62 until second Doppler ultrasound transducer 182 detects the arrival of microbubble-containing contrast agent 45 within the right atrium. Once the second Doppler ultrasound transducer 182 detects the arrival of the microbubble-containing contrast agent 45 in the right atrium (not shown) of subject 8, the controller 60 energizes solenoid 84 causing the displacement of the shuttle (not shown) in the mouthpiece assembly to be displaced to a distal position within the cavity of the mouthpiece assembly 20, thereby causing the vents to open and, in turn, ending the Valsalva maneuver.

Another example embodiment of the disclosure is the provision of a visual display of the exhalation pressure exerted by patient 8 during the Valsalva maneuver. As discussed in the Background of the present disclosure, prior clinical studies have confirmed that the required level of exhalation pressure exerted by a patient during a Valsalva maneuver is at least about 40 mm Hg in order to induce a right-to-left atrial pressure gradient sufficient to reveal the presence of a right-to-left shunt (e.g., a PFO). In addition, prior clinical studies have confirmed that the exertion of an exhalation pressure of at least about 40 mm Hg by the patient during a Valsalva maneuver needs to be at least 5 seconds in duration. As seen in FIG. 1, the Valsalva pressure level 123 exerted by patient 8 is visually displayed, by way of example, in the form of a real-time graph as seen by patient 8 at Valsalva screen display 124 of monitor 10. In the example Valsalva pressure screen display 124 seen in FIG. 1, a horizontal line representing the minimum required Valsalva pressure level 125 provides visual feedback to patient 8 to guide their exertion level during the Valsalva maneuver.

In actual practice, monitor 10 is preferably positioned such that the Valsalva pressure screen display 124 is in the direct line-of-sight of patient 8. However, to facilitate the illustration of all of the components of monitor 10, mouthpiece assembly 20 and catheter set 40 in FIG. 1, the Valsalva pressure screen display 124 is not in the line-of-sight of patient 8 but the line-of-site is represented by sighting path 127.

In the example graph of exhalation pressure as a function of time seen in Valsalva pressure screen display 124 of FIG. 1, the Valsalva maneuver has been completed and the Valsalva release 129 is seen at the end of the period of exhalation exertion corresponding to the moment when the shuttle (not shown) in mouthpiece assembly 20 is rapidly translated to the distal position by the negative pressure rapidly induced by solenoid-driven vacuum/pressurization unit 80, thereby exposing one or a multiplicity of vents 26 and, thereby, forcing complete expiration of the air within the lungs of patient 8. This complete expiration of the air within the lungs of patient 8 represents the release or end of the Valsalva maneuver.

Figure 2:
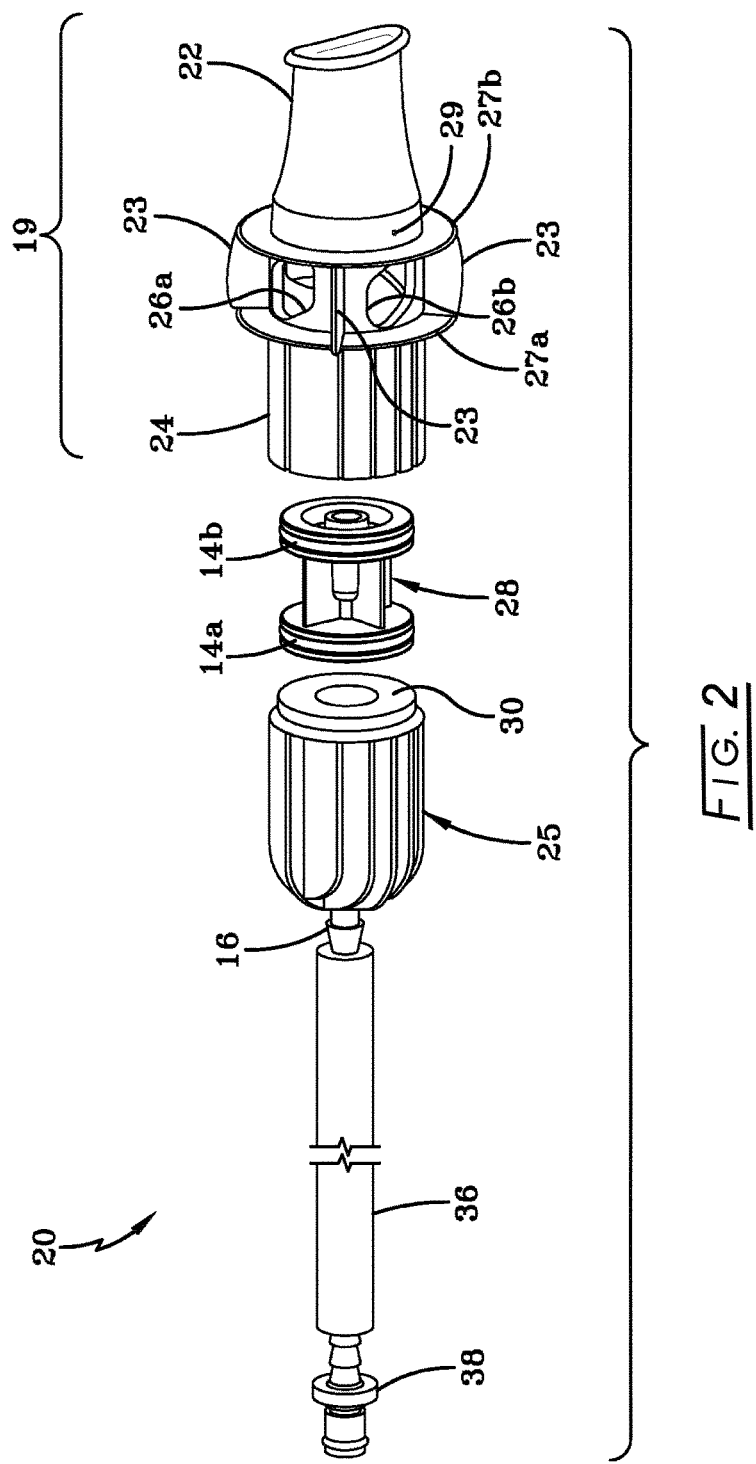
FIG. 2 is an exploded view of mouthpiece assembly of FIG. 1.

Referring now to FIG. 2, an exploded view of one example embodiment of mouthpiece assembly 20 is shown in greater detail, and can be seen to comprise an ergonomic tube 22, tubular body 24, shuttle 28 and end cap 25. A compliant foam rubber sleeve (not shown) may optionally be positioned over tubular body 24 and end cap 25 to facilitate grasping of mouthpiece assembly 20 in either the left or right hand 6 of a patient as illustrated by patient 8 in FIG. 1. Still referring to FIG. 2, an example embodiment of a subassembly 19 may be injection or otherwise molded using a suitable biocompatible plastic offering a relatively low coefficient of friction relative to shuttle O-rings 14a and 14b, and also offering good dimensional control through the injection molding process. By way of example, one usable injection moldable plastic for subassembly 19 is acrylonitrile butadiene styrene (ABS) or blends containing ABS, such as those manufactured by Bayer AG (distributed through Bayer USA, Pittsburgh, Pa.). The subassembly 19 of this embodiment comprises ergonomic tube 22, tubular body 24, one or more vent holes 26, first and second baffle plates 27a and 27b, radial ribs 23a-23d and a leak hole 29. The circular bore of tubular body 24 is accurately dimensioned to receive shuttle 28, including first and second shuttle O-rings 14a and 14b. Embodiments of shuttle 28 may be injection molded using a suitable plastic offering good dimensional control through the injection molding process.

Radial ribs 23 in combination with first and second baffle plates 27a and 27b prevent the hand 6 of a patient from grasping and covering over one or more vent holes 26 and, thereby, causing interference with the air flow exiting the vents when shuttle 28 is translated to its distal position (i.e., the "vents open" position). As seen in FIG. 2, first and second baffle plates 27a and 27b are positioned on subassembly 19 just distal to ergonomic tube 22. During use, as illustrated in FIG. 1, the ergonomic tube 22 is placed in the mouth 4 of patient 8. Upon the forward translation of the shuttle 28 to its most distal position and exposure of one or more vents 26, the baffle plates 27a and 27b serve to direct the rapidly expelled air (issuing from the lungs of patient 8) away from the face and eyes of patient 8.

Still referring to FIG. 2, the interior circular bore of tubular body 24 is dimensioned so that the static friction between shuttle O-rings 14a and 14b and interior wall of tubular body 24 is (a) sufficiently large such that exhalation pressure exerted by patient 8 does not prematurely translate shuttle 28 to a distal position that exposes a portion or all of the one or more vents 26 yet (b) sufficiently small that the negative pressure induced by displacement of the piston in the solenoid-driven vacuum/pressurization assembly creates the force necessary to rapidly translate the shuttle from its starting (proximal) position in which it covers one or more vents 26 to its distal position exposing one or more vents 26.

In one example embodiment and still referring to FIG. 2, and end cap 25 is inserted into and adhesively bonded to tubular body 24 to provide a seal to prevent the egress of air during the Valsalva maneuver. This particular end cap 25 also includes a noise-dampening elastomeric washer 30 to absorb and dissipate the impact energy associated with the rapid translation of shuttle 28 to its most distal position, thereby reducing the noise associated with the translation of shuttle 28 to the distal end of tubular body 24. Also, as seen in the example embodiment shown in FIG. 2, end cap 25 includes a barbed fitment 16 for airtight attachment of the proximal end of flexible extension tube 36 to end cap 25. The distal end of extension tube 36 is secured to a similar barbed fitment at the proximal end of quick disconnect fitment 38. Such a quick disconnect fitment is available from Colder Products Company, Minneapolis, Minn.

By way of example with respect to the embodiments shown in FIGS. 1 and 2, the extension tubing 36 is a biocompatible flexible vinyl tubing having an inside diameter of 0.187 inch and length of 48 inches (Cole-Parmer, Vernon Hills, Ill.). The inside diameter of extension tubing is selected to be (a) large enough to enable sufficient air flow and associated rapid evacuation of air from the distal end of tubular body 24 when piston 94 of solenoid-driven vacuum/pressurization assembly 80 is rapidly withdrawn by energized solenoid 84 and (b) small enough that the interior volume of extension tubing 36, in combination with the interior volume of interior tubing set 100 and the end of tubular body 24 distal to shuttle 28, are sufficiently small to enable an adequate negative pressure within combined total interior volume to force translation of shuttle 28 when the solenoid 84 in solenoid-driven vacuum/pressurization assembly 80 is energized.

Figure 3:
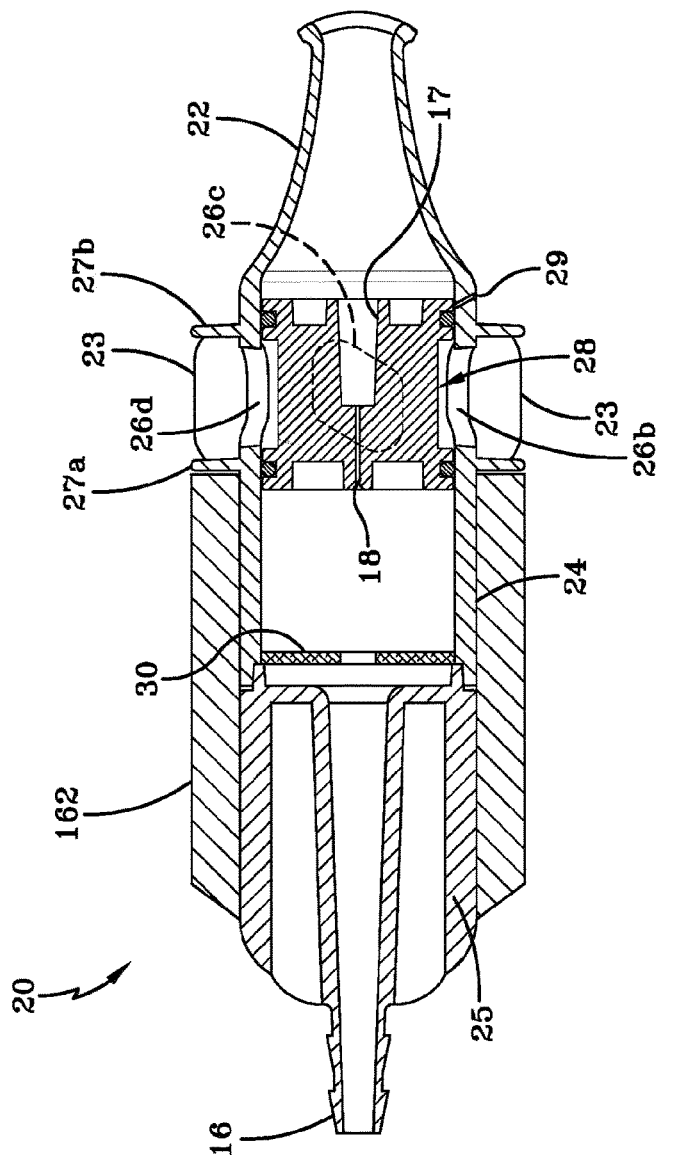
FIG. 3 is a cross-sectional view of the mouthpiece assembly showing a shuttle in initial proximal position in preparation for the start of a Valsalva maneuver.
Figure 4:
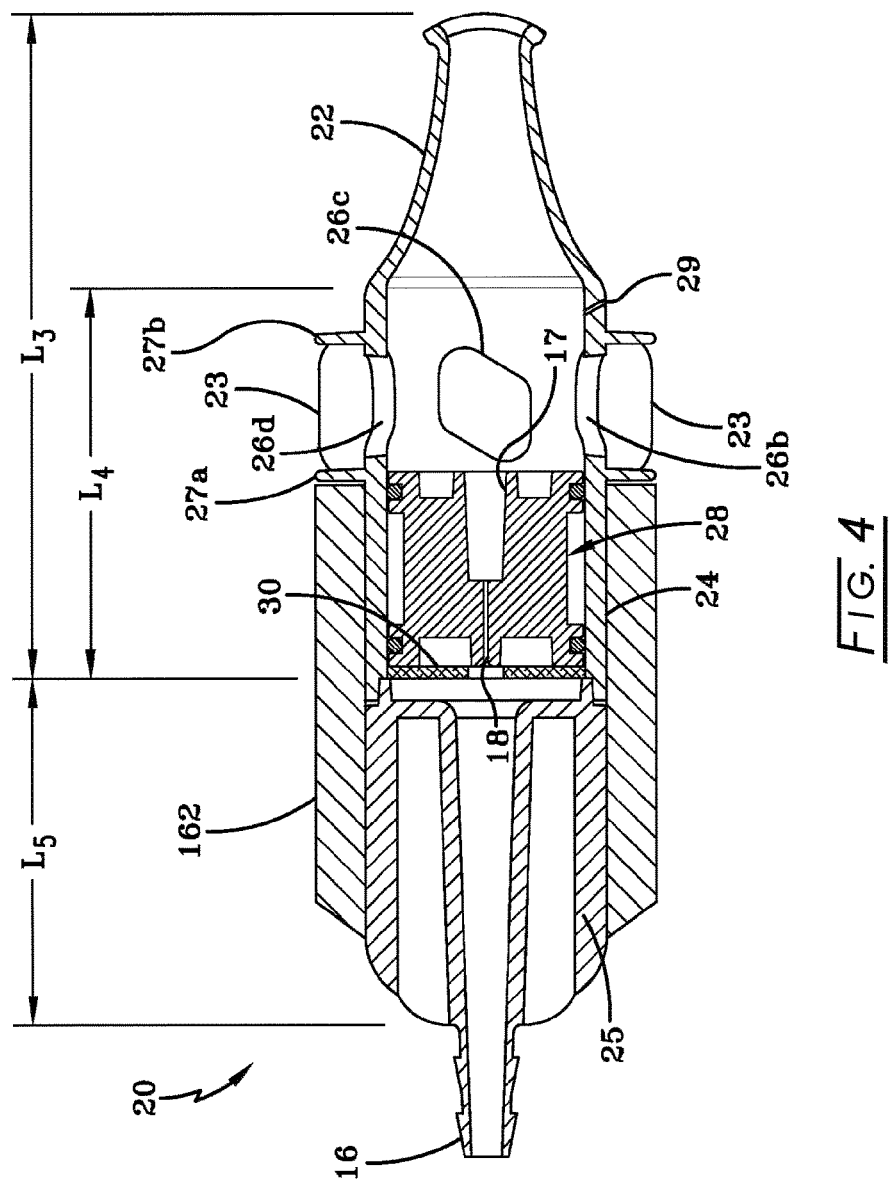
FIG. 4 is a cross-sectional view of the mouthpiece assembly showing the shuttle in a most distal position at the release (end) of a Valsalva maneuver.

Assembly views of an example embodiment of the mouthpiece assembly 20 are depicted in FIG. 3 and FIG. 4 following the placement of shuttle 28 within tubular body 24 and attachment of end cap 25. A compliant sleeve 162 (e.g., biocompatible foam rubber) surrounds and is secured to tubular body 24 and end cap 25 to facilitate grasping of mouthpiece assembly by hand 6 of patient 8 as seen in FIGS. 1, 3 and 4. Also revealed in FIGS. 3 and 4 is noise dampening elastomeric washer 30 mounted on proximal interior surface of end cap 25. An example embodiment of end cap 25 may be injection molded using a suitable biocompatible plastic. By way of example, a suitable injection moldable plastic for end cap 25 is acrylonitrile butadiene styrene (ABS) or blends containing ABS, such as those manufactured by Bayer AG (distributed through Bayer USA, Pittsburgh, Pa.).

Referring now to FIG. 3, shuttle 28 is seen in its initial proximal position in preparation for the start of the Valsalva maneuver. In this proximal position, the shuttle 28 remains stationary during the pressure exertion period of the Valsalva maneuver and blocks air flow access to one or more vents 26 so that patient 8 is able to perform Valsalva maneuver by exerting exhalation pressure of about 40 mm Hg from his or her lungs into ergonomic tube 22 and into the essentially closed volume at the end of the tubular body 24, extension tubing 36 and internal tubing assembly 100. A small leak hole 29 is located proximal to first shuttle O-ring 14a to allow a small flow rate of air to escape from mouthpiece assembly 20 during the Valsalva maneuver.

By way of example and through clinical testing with human subjects, it has been determined that a leak rate of about 20 to 25 cubic centimeters per second under an applied exhalation gauge pressure of 40 mm Hg is (a) large enough to ensure that the exhalation pressure must be exerted by the lungs of patient 8 and not through the use of contraction of distended cheek muscles and (b) small enough to enable an adult to maintain an exhalation pressure of about 40 mm Hg for a period of at least 5 seconds without depleting their natural lung volume capacity. Also, FIG. 3 reveals enlarged entrance hole 17 and pressure equalization channel 18 within shuttle 28, which enables exhalation pressure exerted during the Valsalva maneuver by patient 8 to be dynamically measurable by pressure sensor 110 (see FIG. 1) by virtue of the air column between the mouthpiece assembly 20 and pressure transducer 110.

Referring now to FIG. 4, the shuttle is seen it its most distal position corresponding to the period immediately following the negative pressure induced by the retraction of piston 94 in the solenoid-driven vacuum/pressurization assembly 80 (see also FIG. 1). As seen in FIG. 4, the translation of shuttle 28 to its most distal position exposes one or more vents 26 to the surrounding atmospheric pressure conditions. Immediately following the exposure of the vents and the associated low air flow resistance pathway between ergonomic tube 22 and one or more vents 26, the exhalation exertion by patient 8 ends with the rapid expiration of all pressurized air within the lungs. The rapid expiration of all pressurized air within the lungs thereby ensures the end of the Valsalva maneuver at the precise time when the arrival of the microbubble-containing contrast agent in the right atrium is detected by the precordial Doppler ultrasound transducer positioned on the subject's chest in close proximity to the right atrium.

Referring to FIGS. 2, 3 and 4, the shape of the opening of the one or more vents 26 might be of various shape, such as circular, trapezoidal or square. In an example embodiment, the shape of the opening of six vents 26a-26f may be circular or trapezoidal to minimize the friction between the proximal shuttle O-ring 14a as it traverses the perimeter edges of vents 26a-26f. Also, to ensure acceptably low static and dynamic friction to enable translation of the shuttle from its proximal position as seen in FIG. 3 to its distal position as seen in FIG. 4, a biocompatible lubricant (Dow Corning Silicone 360 Lubricant, Midland, Mich.) is preferably applied (not shown) to the inner smooth walls of tubular body 24 and shuttle O-rings 14a and 14b.

Referring now to FIGS. 5A through 5D, shuttle 28 is seen in a side view, cross-sectional view and perspective views. As can be seen in the side view of FIG. 5A, shuttle 28 includes shuttle O-ring grooves 13a and 13b. The cross-sectional view seen in FIG. 5B reveals elastomeric shuttle O-rings 14a and 14b positioned in shuttle O-ring grooves 13a and 13b. By way of example, shuttle O-rings 14a and 14b may be Size No. 20, Buna-N material, 0.864 inch ID×0.070 inch wide (available Parker Hannifin Corporation, Lexington, Ky.). As also seen in FIG. 5B, both a larger and smaller hole extends across the full length of shuttle 28. The larger entrance hole 17 (e.g., 0.18 inch diameter by 0.56" long) provides a low resistance to air flow between the proximal surface of shuttle 28 and the start of the smaller diameter pressure equalization hole 18 as seen in FIG. 5B. The larger entrance hole 17 also minimizes the possibility that any fluid that might be ejected from the mouth 4 of patient 8 results in the occlusion of the pressure equalization channel 18. An example embodiment of shuttle 28 of the disclosure includes a pressure equalization channel having a diameter of 0.026 inches and a length of 0.44 inches. Perspective views of shuttle 28 are seen in FIGS. 5C and 5D, revealing an opening of larger entrance hole 17 and pressure equalization channel 18, respectively.

Figure 6:
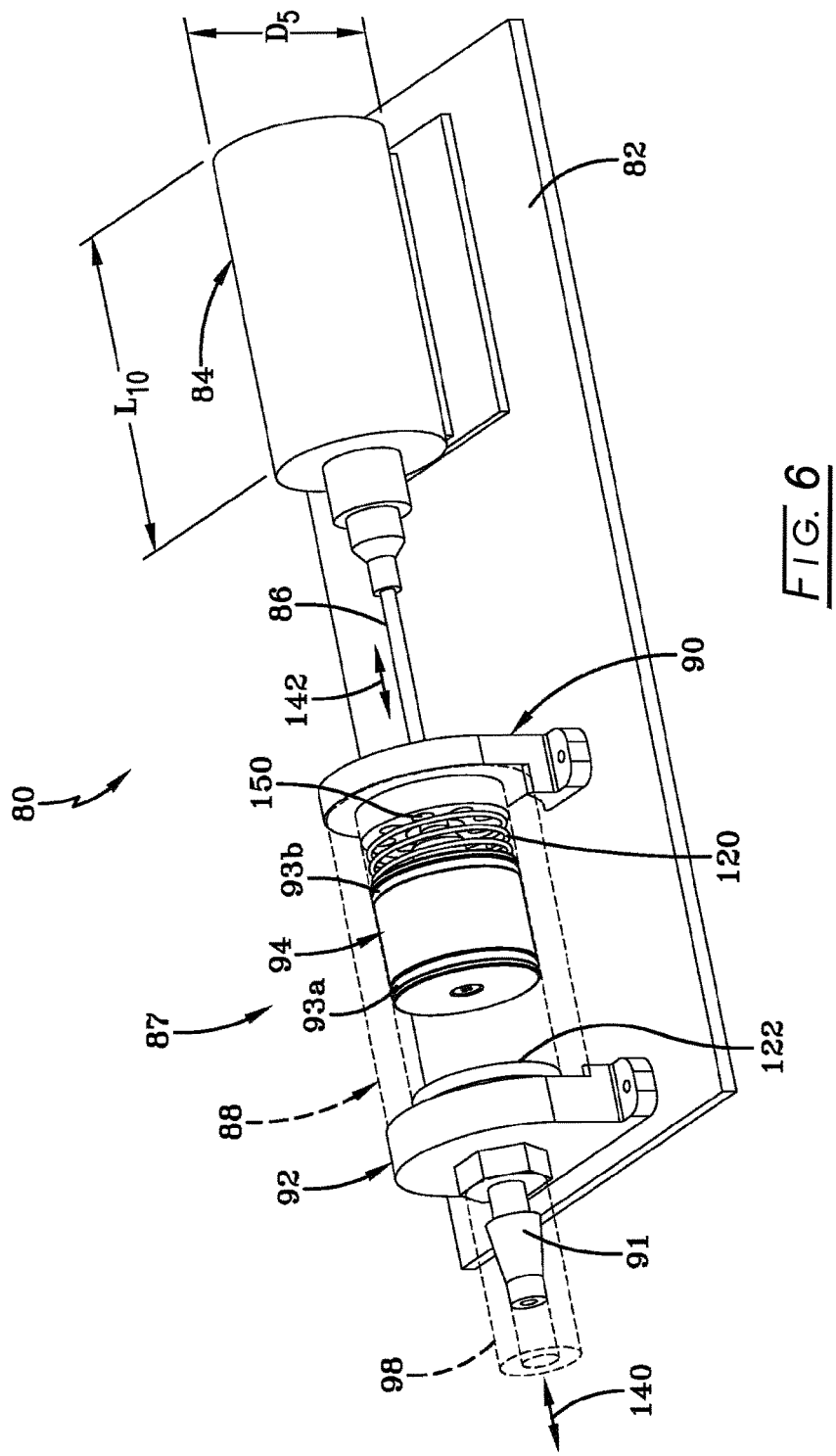
FIG. 6 is a perspective view, partly in section, of an example embodiment of a vacuum/pressurization subassembly.

An assembly view of the example solenoid-driven vacuum/pressurization assembly 80 is illustrated in FIG. 6, which comprises vacuum/pressurization subassembly 87, solenoid 84, solenoid drive rod 86 and platform 82. The vacuum/pressurization subassembly 87 seen in FIG. 6 comprises vacuum/pressurization tube 88, piston 94, compression spring 120 and first and second tube support endplates 90 and 92.

By way of example, an example embodiment of the solenoid-driven vacuum/pressurization assembly 80 employs a Ledex 150 pull-type tubular solenoid (Johnson Controls, Vandalia, Ohio) for solenoid 84, providing a maximum stroke length of 0.7 inches and a pull-force of about 5 to 7 pounds. Still referring to FIG. 6, compression spring 120 of the example vacuum/pressurization subassembly 87 may be, by way example, a stainless steel spring, having a 1.218 inch OD, a 0.063-inch wire diameter, and an overall free length of 1.75 inches (available from, e.g., Lee Spring, Bristol, Conn.). Also by way of example, vacuum/pressurization tube 88 may be machined from a plastic having a low coefficient of friction, such as acetal resin (e.g., Delrin, DuPont, Parkersburg, W. Va.), to enable reliable translation of the piston 94 within vacuum/pressurization tube 88 during alternating evacuation and pressurization cycles.

The inner circular walls of vacuum/pressurization tube 88 are preferably machined and polished to a smooth finish in order to minimize static and dynamic friction between first and second piston O-rings 93a and 93b and the inner wall of vacuum/pressurization tube 88 during the cyclic translation of piston 94. In addition, a lubricant is preferably applied to the inner walls of the vacuum/pressurization tube 88 in order to further minimize static and dynamic friction during the cyclic translation of the piston. By way of example, the lubricant (not shown) may be Super-O-Lube (Parker Hannifin Corporation, Lexington, Ky.).

As seen in FIG. 6, first and second tube support end plates 90 and 92 are attached at either end of vacuum/pressurization tube 88 with an air-tight sealing adhesive used at the interface between the vacuum/pressurization tube 88 and second tube support end plate 92. A barbed fitment 91 is attached to the exterior side of second tube support end plate 92 to provide for secure and airtight connection to first tubing member 98. Tubing member 98 extends to and is secured with an airtight seal to a "T" shaped barbed fitment (not shown) with (a) first remaining branch of the "T" extending to pressure sensor 110 via second tubing member 106 with airtight seals at both ends of tubing member 106 and (b) second remaining branch of the "T" extending to a quick-disconnect front panel receptacle 104 via third tubing member 105 with airtight seals at both ends of tubing member 105 (also refer to FIG. 1). Also seen in FIG. 6 is solenoid pull rod 86 with a movement vector 142 illustrating translation of solenoid pull rod 86 during alternating evacuation and pressurization cycles. The vacuum/pressurization subassembly 87 and solenoid 84 are mounted (e.g., mechanically attached using machine screws and nuts) on platform 82 to maintain and stabilize their relative positions during alternating evacuation and pressurization cycles. Still referring to FIG. 6, a noise dampening elastomeric disk 122 is positioned at the distal end of vacuum/pressurization tube 88 to dissipate the kinetic energy and force associated with the translation of piston 94 by compression spring 120 immediately following de-energizing of solenoid 84, thereby reducing the noise associated with the return of piston 94 to the distal end of vacuum/pressurization tube 88.

Figure 7:
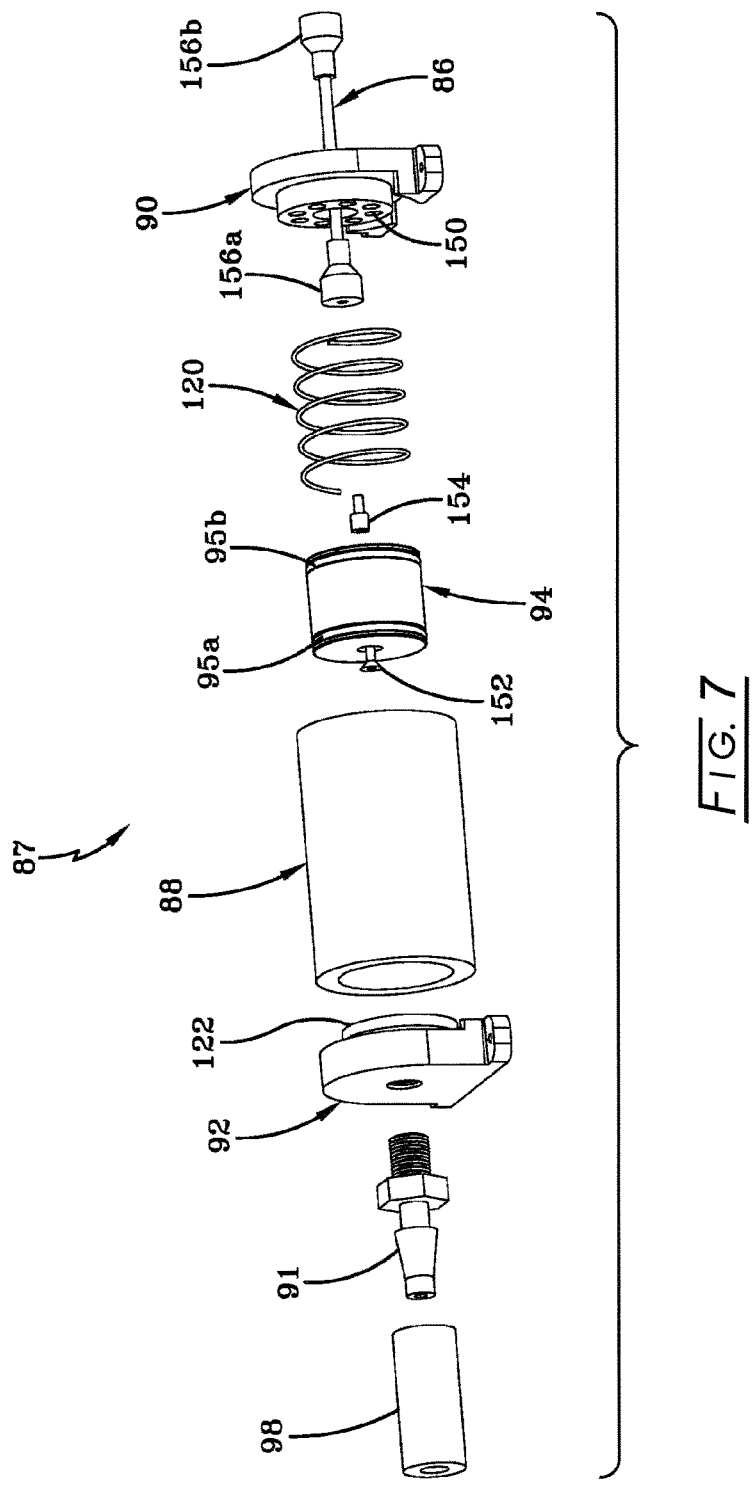
FIG. 7 is an exploded view of vacuum/pressurization subassembly of FIG. 6.

An exploded view of vacuum/pressurization subassembly 87 is seen in FIG. 7 providing addition details of an example embodiment of its construction. Flat-head machine screw 152 extends through piston 94 and is threaded into piston attachment cap 154. Piston attachment cap 154 is mechanically secured to solenoid pull rod 86 at first drive rod coupling 156a. Second drive rod coupling 156b is mechanically secured to plunger (not shown) of solenoid 84.

By way example, solenoid pull rod 86 comprises a flexible cable with drive rod couplings 156a and 156b secured at either end through mechanical swaging of couplings onto flexible cable. The use of a flexible cable in solenoid pull rod 86 compensates for any misalignment that may exist between the central axis of translation of piston 94 and the central axis of translation of the plunger in solenoid 84. See for example commercially available Flexible Drive Shaft (Stock Drive Components/Sterling Instrument, New Hyde Park, N.Y.).

Referring now to FIGS. 8A and 8B, piston 94 is shown in a cross-sectional view and perspective view, respectively. As seen in the cross-sectional view of piston 94 in FIG. 8A, piston O-rings 95a and 95b (e.g., Buna N, Parker Hannifin Corporation, Lexington, Ky.) are positioned in piston O-ring grooves 93a, 93b. Counter bore 158 in piston 94 receives piston attachment cap 154 at the proximal end of piston 94. Drilled and counter bored hole 159 receives piston attachment flat head machine screw 152.

Three of the components of the example embodiment of the vacuum/pressurization subassembly 87 seen in FIG. 6 are shown in greater detail in FIGS. 9, 10A, 10B, 11A and 11B. By way of example and referring first to FIG. 9, vacuum/pressurization tube 88 is shown along with defining dimensional parameters of a circular cross-section tube machined from a low coefficient of friction material (e.g., Delrin). The inner bore 160 is preferably polished to reduce the static and dynamic friction relative to piston O-rings 95a and 95b during the translation of piston 94 during the evacuation and pressurization cycles (see also FIG. 8A).

First tube support end plate 90 is seen in FIG. 10A showing circular channel 151 sufficiently large to accommodate passage of solenoid drive rod 86 and its end fitments 156a and 156b to effect a linkage between a plunger (not shown) in solenoid 84 and piston 94 (see also FIG. 7). By way of example and referring next to cross-sectional and perspective views seen in FIGS. 10A and 10B, additional vent holes 150 are machined through first tube support end plate 90 to provide a low resistance pathway for air flow into or out of vacuum/pressurization tube 88 during the translation of piston 94 associated with the evacuation and pressurization cycles (see also FIGS. 6 and 7).

By way of example and referring next to the cross-sectional and perspective views seen in FIGS. 11A and 11B, second tube end plate support 92 is covered with noise dampening elastomeric disk 122 to dissipate the kinetic energy of and force applied to piston 94 as it is translated to its most distal position by compression spring 120 following the de-energizing of solenoid 84. Threaded hole 163 is machined through the full thickness of second tube end plate support 92 to receive the threaded end of vacuum/pressurization barbed fitment 91 (see also FIGS. 6 and 7).

By way of example, the dimensions of the components of one example embodiment of mouthpiece assembly 20 and solenoid-driven vacuum/pressurization assembly 80 are summarized below, in units of inches, with the identification of these dimensions seen in FIGS. 4, 5B, 6, 8A, 9, 10A and 11A. The dimensions listed below, in units of inches, are provided merely for illustration and not limitation, as a wide range of possible dimensions would enable a functioning device as long as the vacuum and pressurization parameters as well as pressure equalization flow parameter required for reliable translation of shuttle 28 are achieved.

TK=0.05 to 0.20
TK2=0.04 to 0.05
D1=0.98
D2=0.18
D3=0.026
D4=1.235
D5=1.25
D6=1.71
D7=1.229
D8=0.125
D9=0.185
D10=0.50
L1=1.02
L2=0.44
L3=3.00
L4=1.65
L5=1.53
L6=1.00
L7=2.75
L8=0.50
L9=0.50
L10=2.50
L11=0.50
L12=0.040 to 0.080
L13=0.080
L14=1.50
L15=0.20
L16=0.035
W1=0.60
W2=0.80
W3=0.040 to 0.080
W4=0.035

Figure 12:
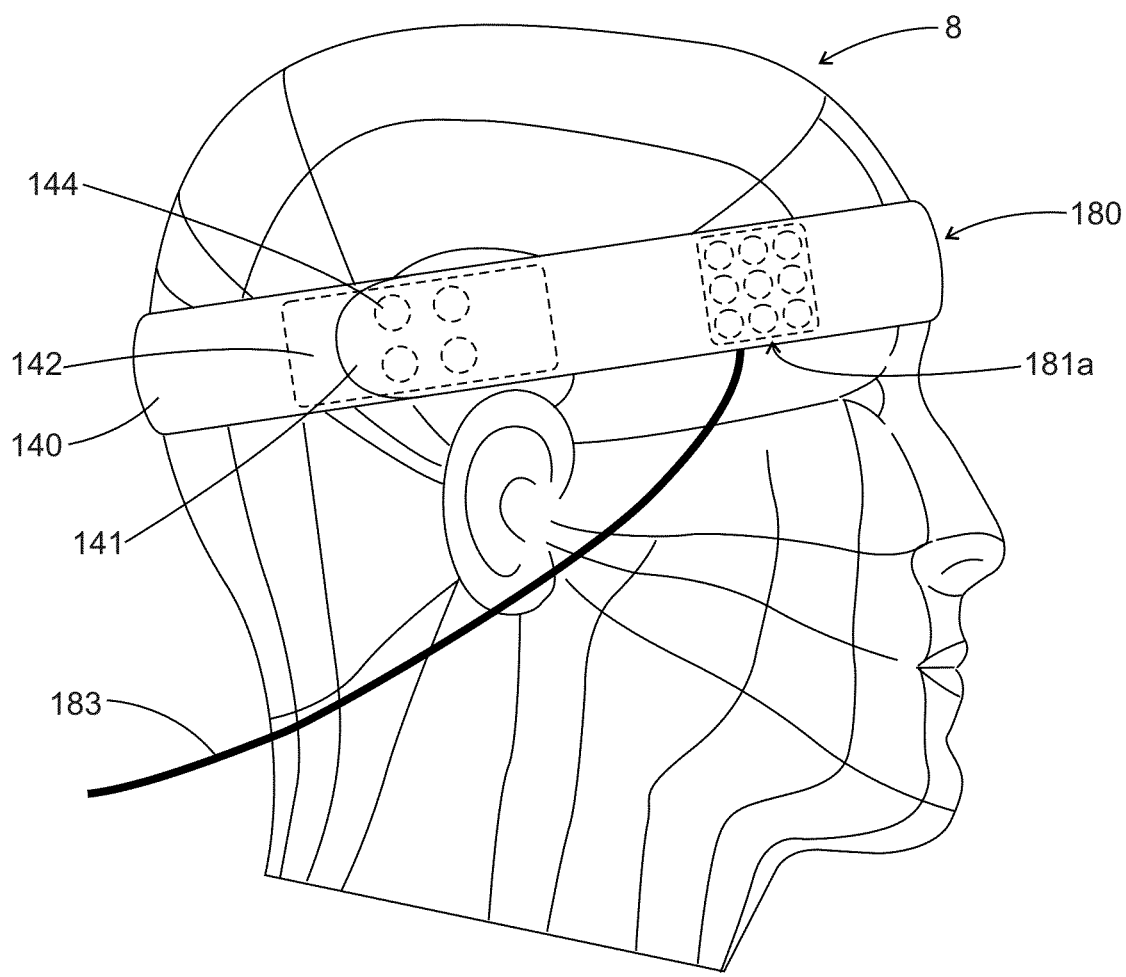
FIG. 12 is a perspective view of an example headband incorporating an example first set of Doppler ultrasound arrays for targeting of intracranial arteries and adjustably positionable on the surface of the subject's head adjacent to one or both hemispheres of the brain.

An example illustration of headband 180 positioned on the head 8 of subject is seen in FIG. 12. The headband 180 comprises adjustable and flexible strap 140, flexible ferromagnetic metal strip 142 in region corresponding to range of positions of strap end 141 and multiple disc-shaped magnets 144. By way of example, small diameter, low-profile disc-shaped magnets 144, primarily composed of neodymium, iron and boron, are manufactured and supplied by K&J Magnetics, Inc., Pipersville, Pa. The ferromagnetic metal strip may be stainless steel Type 430 having a thickness, for example, of 0.015 inch and available from McMaster-Carr, Santa Fe Springs, Calif. By way of example, headband 180 may be fabricated using two flexible vinyl layers adhesively bonded together to contain disc-shaped magnets 144 and ferromagnetic strip 142. As seen in example illustration in FIG. 12, first Doppler ultrasound transducer array 181*a* is affixed to headband 180 on right side of head 8 of subject adjacent to underlying targeted intracranial arteries within skull of head 8. An optional matching first Doppler ultrasound transducer array 181*b* (not shown) may be affixed to headband 180 on right side of head 8 of subject adjacent to underlying targeted intracranial arteries within skull of head 8. Referring to FIG. 1 and FIG. 12, cable 183 provides electrical communication between the first Doppler ultrasound transducer array 181*a* and monitor 10 via removably attachable connector 185. Removably attachable connector 185 communicates with controller 60 via receptacle 149 and cable 187.

Figure 13:
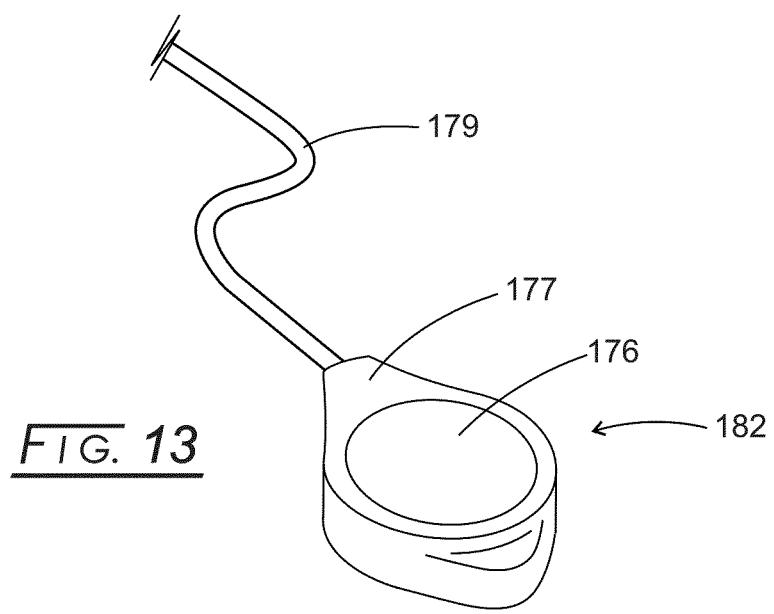
FIG. 13 is a perspective view of an example second Doppler ultrasound array for targeting the right atrium of the heart and positionable on the precordium of the subject.

By way of example and referring now to FIG. 13 as well as FIG. 1, an example of a second Doppler ultrasound transducer 182 is illustrated including a skin-interface surface 176 and transducer housing 177. Cable 179 provides electrical communication between the second Doppler ultrasound transducer 182 and monitor 10 via removably attachable connector 186. Removably attachable connector 186 communicates with controller 60 via receptacle 188 and cable 190. As seen in FIG. 1, second Doppler ultrasound transducer 182 may be secured to pericardium of subject using strip of medical-grade adhesive tape, 184. For example, a commercially available version of second Doppler ultrasound transducer 182 seen in FIG. 13 is available as Medasonics Model P81 Probe from Med-Electronics, Beltsville, Md.

Figure 14:
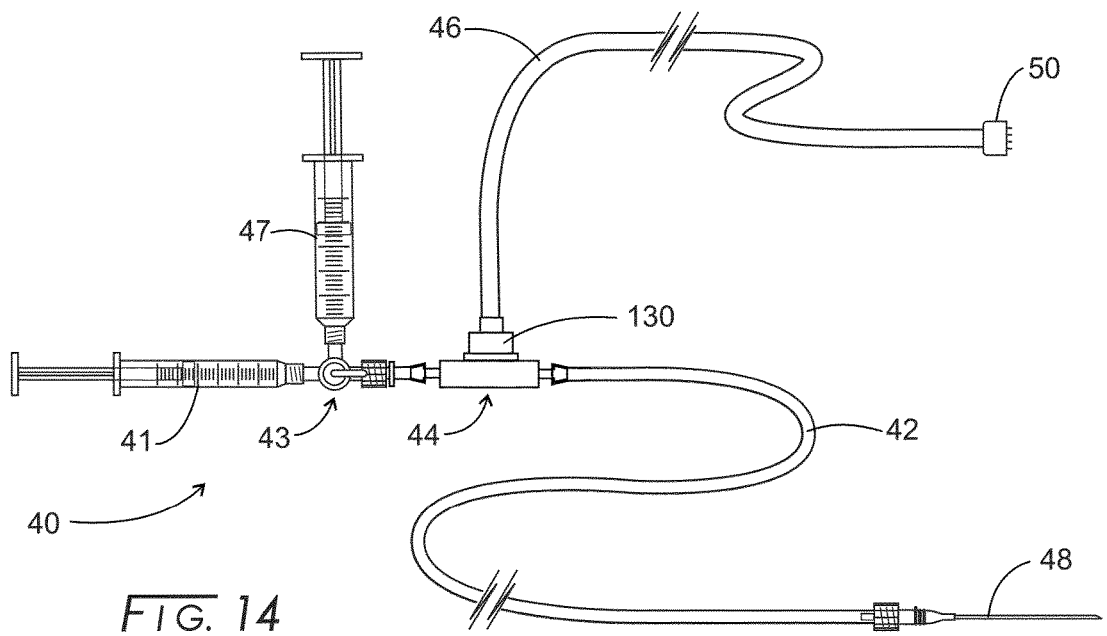
FIG. 14 is a perspective view of an example single-use catheter set comprising contrast agent preparation syringes, three-way stopcock, flexible extension tubing, microbubble counting cell and venous access needle for access to vein of subject.

An example of a single-use catheter set 40 is seen in FIG. 14 and FIG. 1 comprising first syringe 47, second syringe 41, three-way stopcock 43, microbubble counting cell 44, flexible catheter 42 and venous access needle 48. In addition to the components of single-use catheter set 40 seen in FIG. 14, removably attachable digital image sensor 130 is positioned on surface of microbubble counting cell 44. The image sensor 130 communicates with monitor 10 via cable 46 that terminates in removably attachable connector 50. As seen in FIG. 1, removably attachable connector 50 communicates with controller 60 via receptacle 51 and cable 108. By way of example, a mixture of isotonic saline, air and blood withdrawn from subject (e.g., a mixture having a total volume of 10 milliliter and comprising, by volume, 80% isotonic saline, 10% air and 10% blood) is rapidly expelled from first syringe 47 into second syringe 41 via three-way stopcock 43 and then rapidly expelled from second syringe 41 back into first syringe 47 to complete one agitation cycle. Alternatively, a mixture of isotonic saline and air withdrawn from the subject (e.g., a mixture having a total volume of 10 milliliter and comprising, by volume, 90% isotonic saline and 10% air) is rapidly expelled from first syringe 47 into second syringe 41 via three-way stopcock 43 and then rapidly expelled from second syringe 41 back into first syringe 47 to complete one agitation cycle. Alternatively, other sterile isotonic aqueous solutions suitable for IV injection may be used in place of an isotonic saline solution, for example, sterile Ringers isotonic solution. This agitation cycle is typically repeated a total of six to ten cycles to complete the agitation process and the associated creation of microbubbles to produce an ultrasound contrast agent 45. The ultrasound contrast agent 45 is then injected into the venous blood stream of the subject by ejecting the agitated mixture through the microbubble counting cell 44 and along the length of flexible catheter 42 (e.g., one to three feet in length) and into a vein (e.g., antecubital vein) of the subject via a venous access catheter 48. Immediately following the injection of the prepared contrast agent 45, digital image sensor 130, removably attached to the microbubble counting cell 44, captures an image of the substantially stationary layer of injected contrast agent 45 within a predefined microbubble counting zone (not shown) of the microbubble counting cell for subsequent and immediate automated image analysis by the controller to count the number of microbubbles within the defined zone of microbubble counting cell 44. The medical grade, sterile 10 milliliter syringes, three way stopcock, flexible tubing and venous access catheter are components that are commercially available, for example, from Becton, Dickinson and Company, Franklin Lakes, N.J.

Figure 15:
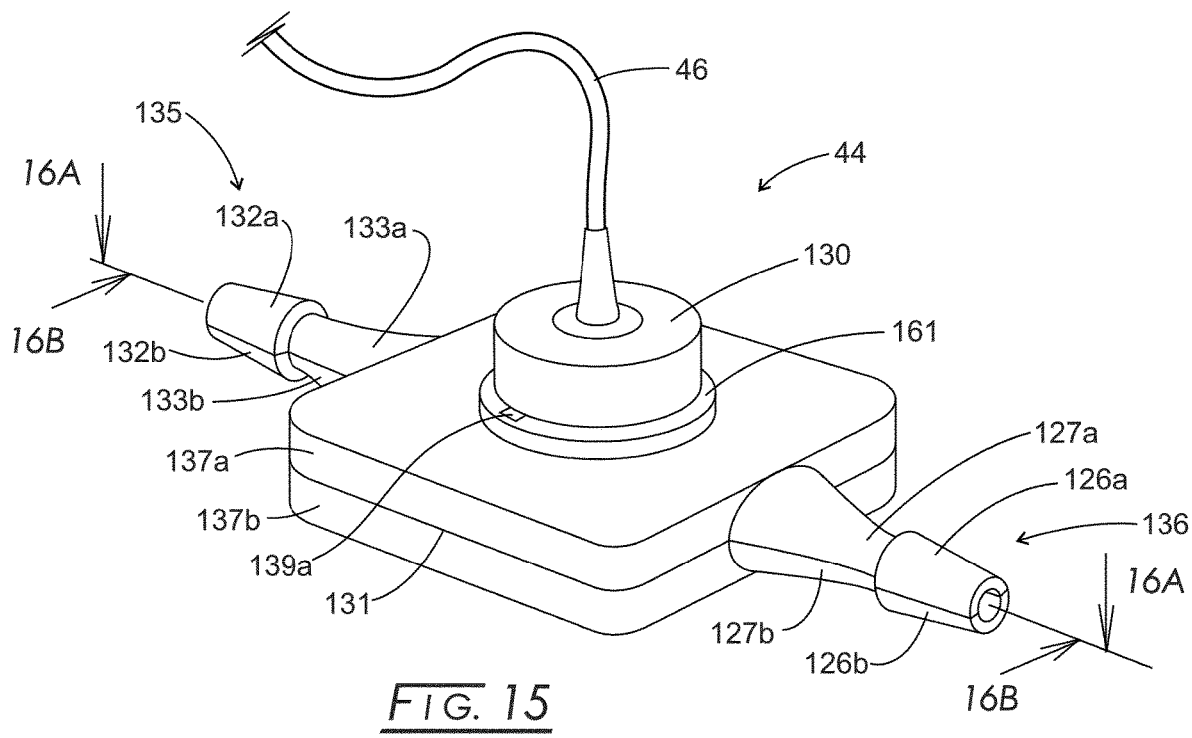
FIG. 15 is a perspective view of an example assembly of a microbubble counting cell and digital image sensor.

By way of example and referring now to FIG. 15, the single-use microbubble counting cell 44 component and removably attachable digital image sensor 130 are seen in a perspective view. In the example seen in FIG. 15, the microbubble counting cell 44 comprises an upper half cell plate 37*a* and lower half cell plate 37*b* injection molded from optically clear plastic (e.g., cyclic olefin copolymer available from Topas Advanced Polymers, Florence, Ky.) that are adhesively bonded along a parting line 131. First end 135 of upper half cell plate 37*a* includes semi-cylindrical upper first tubular extension 133*a* and semi-cylindrical upper first barbed fitment 132*a*. Second end 136 of upper half cell plate 37*a* includes semi-cylindrical upper second tubular extension 127*a* and semi-cylindrical upper second barbed fitment 126*a*. Likewise, first end 135 of lower half cell plate 37*b* includes semi-cylindrical lower first tubular extension 133*b* and semi-cylindrical lower first barbed fitment 132*b*. Second end 136 of lower half cell plate 37*a* includes semi-cylindrical upper second tubular extension 127*b* and semi-cylindrical lower second barbed fitment 126*b*. Entry slot 139*a* is seen in support member 161 to enable locking pin (not shown) on body of digital image sensor 130 to access locking groove 138 seen in FIG. 16B and securing digital image sensor 130 within support member 161 by, for example, a one-quarter turn of locking pin along the length of the locking groove 138. The digital image sensor communicates with monitor 10 and associated controller 60 via cable 46 as described above in connection with FIG. 14.

Still referring to FIG. 15, digital image sensor 130 is essentially the same type of digital image sensor used in portable smart phones such as Apple iPhones or other smart phones incorporating high definition cameras. By way of example, digital image sensor 130 may a 13-megapixel digital image sensor whose individual pixel size is 1.12 microns×1.12 microns (where the unit micron refers to micrometer) in an array of 4224×3136 pixels available as Model No. OV13853 digital image sensor available from OmniVision Technologies, Inc., Santa Clara, Calif. Since the minimum diameter of a microbubble image that needs to be captured within the microbubble counting cell by the digital image sensor 130 is about 10 microns, the 1.12 micron by 1.12 micron pixel size of this example digital image sensor 130 enables a total of about 64 pixels to define the image corresponding to each 10 micron diameter microbubble in the field of view being analyzed. For the case of the average diameter microbubble size of about 25 microns, the 1.12 by 1.12-micron pixel size of this example digital image sensor 130 enables a total of about 390 pixels to define the image corresponding to each 25-micron diameter microbubble. Based on this small pixel size of the example digital image sensor 130, even the smallest 10-micron diameter microbubble generated by the agitation process will be clearly resolvable by digital image sensor 130 and, therefore, countable using digital image analysis software. Regarding software and systems for the digital analysis of images of the microbubble counting zone containing a multiplicity of microbubbles, see De Costa, L., Digital Image Analysis of Blood Cells. Clinical Laboratory Medicine 2015; 35: 105-122, which discloses commercial sources for such software.

Figure 16A:
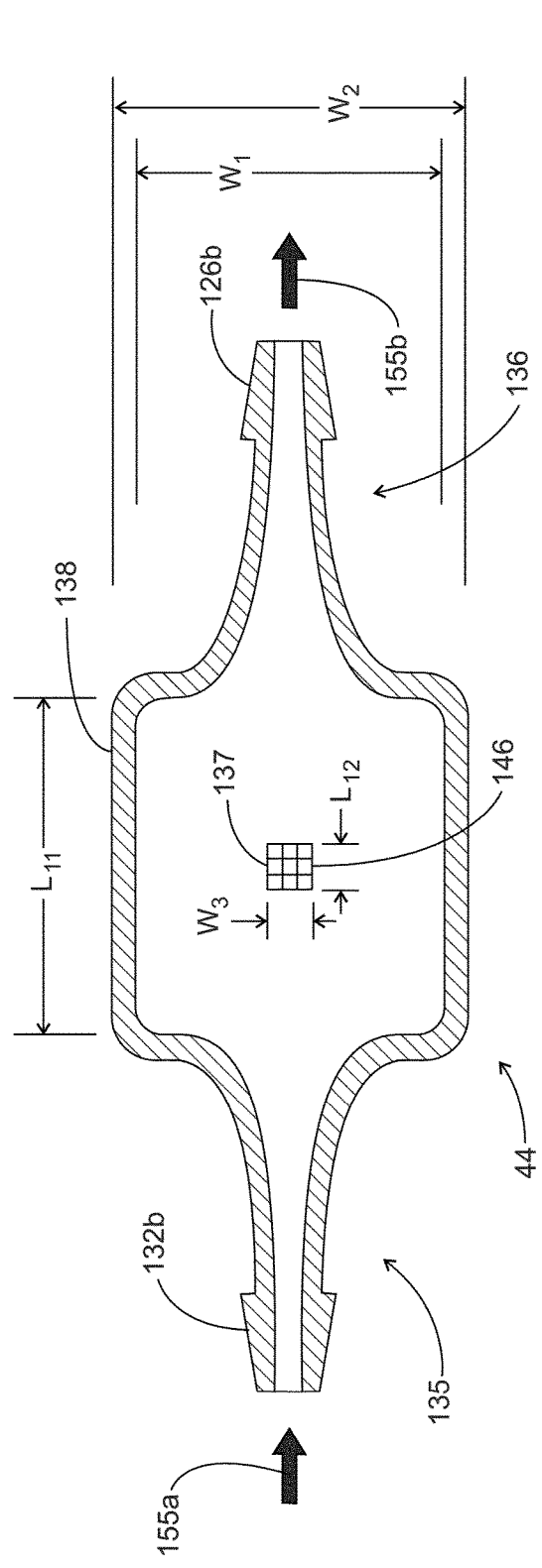
FIG. 16A is a top view of the lower half of the microbubble counting cell seen in FIG. 15.
Figure 16B:
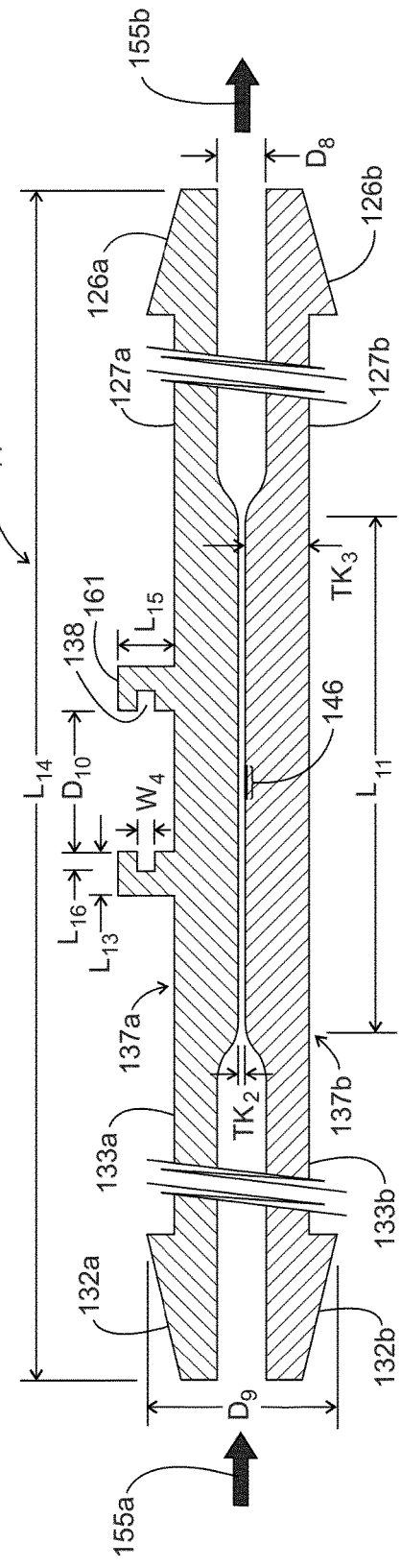

Referring now FIG. 16A as well as FIG. 15, a top view of the lower half cell plate 37b of microbubble counting cell 44 is seen with dimensions as specified thereon. As seen in FIG. 16A, when upper half cell plate 37a (not shown) and lower half cell plate 37b are assembled, then contrast agent 45 enters first end 135 as seen at arrow 155a, spreads uniformly throughout the larger flow area of microbubble counting cell 44 defined by dimensions L11 and W1, and then exits at second end 136 as seen at arrow 155b. Within the larger flow area of microbubble counting cell 44 defined by dimensions L11 and W1 is microbubble counting zone 146 defined by length L12 and width W3. By way of example, to enable accurate counting of microbubbles contained within contrast agent 45, said microbubble counting zone might further be defined by a grid 137 created by laser etching a perpendicular pattern of lines to facilitate counting of microbubbles within each sub-region within grid 137. By way of example, a set of eight equispaced perpendicular lines at 0.5 mm spacing may be laser etched onto the inner surface of lower half cell plate 37b in microbubble counting zone 146 to form a grid pattern containing nine sub-regions measuring 0.5 mm×0.5 mm to facilitate image analysis software based counting of microbubbles within each sub-region to obtain total count of microbubbles within microbubble counting zone 146. The width W3 and length L12 of microbubble counting zone 146 is combined with the liquid layer thickness TK2 of contrast agent 45 (as seen in FIG. 16B) to determine the physical volume of the microbubble counting zone 146. By way of example, if width W3 and length L12 of microbubble counting zone 146 are both 1.5 mm and thickness TK2 of liquid layer in microbubble counting zone 146 is 0.1 mm, then total volume of microbubble counting zone 146 is 0.225 cubic mm. If the total amount of contrast agent injected into a vein of the subject is 10 ml, which is equivalent to 10,000 cubic mm, then the total number of injected microbubbles is derived by multiplying the number of microbubbles counted within microbubble counting zone 146, NCOUNT by the ratio 10,000 cubic mm/0.225 cubic mm or 44,444. By way of further example, if the number of counted microbubbles, NCOUNT within microbubble counting zone 146 is 500, then the total number of microbubbles contained in a 10 ml volume of contrast agent is 500×44,444 or 22,222,000 microbubbles for a given agitated saline preparation of injected contrast agent 45.

Referring now to FIG. 16B, a cross-sectional side view of the microbubble counting cell seen in FIG. 15 is shown in greater detail with dimensions as defined thereon. As seen in FIG. 16B, liquid flow path and associated liquid layer thickness in region of microbubble counting zone 146 has a specified thickness of TK2. Preferably, the liquid layer thickness, TK2 in the microbubble counting zone 146 is in the range from 0.10 to 0.12 mm (0.0039 to 0.0047 inch). The preferred thickness of the liquid layer in the microbubble counting zone 146 is selected to enable more accurate counting of microbubbles by minimizing multiple layers of microbubbles in the defined microbubble counting zone 146. In this regard, refer to Jeon, D., et al., The Usefulness of a 10% Air-10% Blood-80% Saline Mixture for Contrast Echocardiography: Doppler Measurement of Pulmonary Artery Systolic Pressure. Journal of American College of Cardiology 2002; 39 [1]: 124-129, incorporated herein by reference.

Still referring to FIG. 16B as well as FIG. 15, support member 161 is seen extending from upper half cell plate 37a with dimensions as defined thereon. The inner circular surface of support member 161 incorporates a circumferential locking groove 138. The circumferential locking groove 138 retains locking pin extending from sidewall of base of digital image sensor 130 (not shown) to temporarily secure removably attachable digital image sensor 130 onto microbubble counting cell 44.

Figure 17:
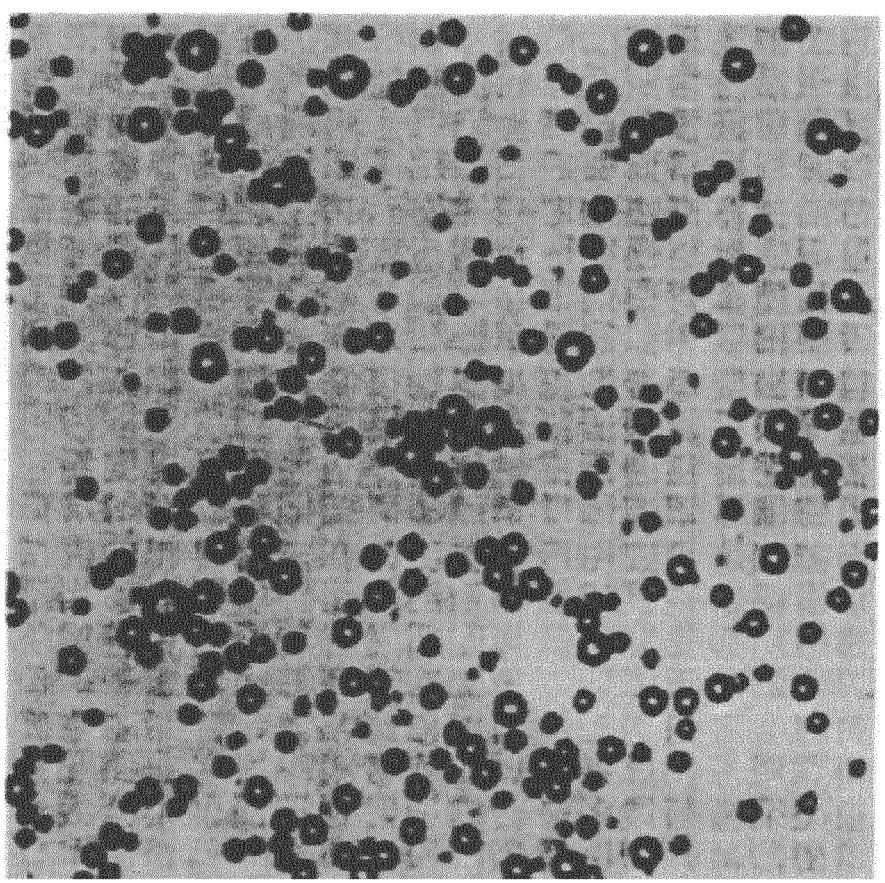
FIG. 17 is an example view of the image acquired by the digital image sensor following the injection of the contrast into the microbubble counting cell.

Turning now to FIG. 17, an example photograph is seen of microbubbles that are contained within a counting zone measuring 1.00 mm×1.00 mm×0.10 mm thick. This example of microbubbles created by agitating 8.0 ml isotonic saline, 1.0 ml of air and 1.0 ml plasma with 10 agitation cycles corresponds to a total number 3.3 million microbubbles in a 10 ml volume of prepared contrast agent 45. This example photograph is representative of the approximate number and distribution of microbubbles seen by digital image sensor 130 in the present disclosure.

A method for the detection of the number of embolic tracks is described in the following example. As discussed in the Background section, established Transcranial Doppler methods for shunt detection involve the injection of an agitated air-saline solution into an antecubital vein followed by the use of ultrasound insonation of targeted middle and anterior cerebral arteries to detect the number of microbubbles that may reach the vasculature of the brain. The system of the present disclosure will incorporate the use of digital ultrasound signals using multiple sample gates placed at short intervals (e.g., 2 mm) and simultaneously processed to provide a color-based signal power M-mode ultrasound image as described below.

The M-mode of Doppler ultrasound detection presents the temporal changes in echoes received from interfaces in which the depth of echo-producing interfaces associated with red blood cells are displayed along a first axis and time is displayed along a second axis thereby recording signals associated with motion of the echo-producing interfaces toward the transducer (e.g., shown in red) and away from the transducer (e.g., shown in blue). For purposes of ultrasound transducer positioning and orientation, the shade of the red or blue color is displayed as a function of the power of the Doppler signal and detected velocity. The greater the backscattered power, the more intense the colors associated with detected interfaces moving towards or away from the ultrasound transducer. A spectrogram displayed as a function of depth so that the displayed power or intensity of the backscattered beam increases as the beam is more optimally aimed at blood flow within the targeted middle and anterior cerebral arteries. In particular, the intensity of the backscattered beam increases as the volume of moving blood in the sampled volume increases. The maximum intensity of the backscattered ultrasound beam corresponds to having centered the ultrasound beam on the targeted middle and anterior cerebral arteries. A more detailed description of this power-based M-mode Doppler ultrasound method for detecting blood flow is described in U.S. Pat. No. 6,196,972 incorporated herein in its entirety.

Following the injection of an agitated saline solution containing millions of air bubbles having a geometric mean diameter of about 28 microns and ranging from about 10 to 80 microns, the power-based M-mode Doppler ultrasound method is used during a pre-determined time interval after the injection of the agitated saline contrast agent to accurately detect individual microbubbles in the form of discernable embolic tracks as the microbubbles pass through the insonated middle and anterior cerebral arteries. Using the power-based Doppler ultrasound method, microbubbles appear as high-power transient signatures that appear in the form light-colored tracks and clearly distinct from backscatter associated with surrounding blood flow.

A software-based algorithm analyzes the recorded Doppler ultrasound images to determine the number of detected embolic tracks or intensity of the bubble shower. An example of such a software-based algorithm is disclosed in U.S. Pat. No. 7,771,358, which is incorporated herein by reference in its entirety. Once normalized with respect to a standard number injected microbubbles, the normalized number of bilateral embolic tracks or bubble shower will graded in accordance with the established scales for quantifying the conductance of right-to-left cardiac shunts.

A general flow chart of the operation of an example embodiment of the system is collectively represented by FIGS. 18A-18G. These figures are combined as labeled thereon to provide a single flow chart describing the example system and method for the detection and quantification of the conductance of a right-to-left shunt using a Transcranial Doppler ultrasound apparatus, system and method including the performance of a Valsalva maneuver. The specified apparatus, system and method for the detection and quantification of the conductance of a right-to-left shunt and performing a Valsalva maneuver can utilize the following protocol without extensive experimentation.

Referring first to FIG. 18A, beginning as represented by symbol 200 and continuing as represented by arrow 202 to block 204, controller 60 within monitor 10 carries out system initialization with the establishment of default parameters. Operator enters the volume of the contrast agent that will be injected into the subject's vein for each test. First test index, NTEST is set to a value of 1. Next, as represented at arrow 206 and block 208, the program continues where first Doppler ultrasound transducer arrays are positioned on head of subject on one hemisphere or both hemispheres of skull adjacent to targeted intracranial arteries. Cable extending from first Doppler ultrasound transducer arrays is connected to monitor using connector at proximal end of cable at designated receptacle on monitor. By way of example, such first Doppler ultrasound transducer arrays and supporting headband are shown as 180 and 181 in FIG. 1.

The program continues as represented at arrow 210 to block 212 of FIG. 18A. Block 212 provides for positioning a second Doppler ultrasound transducer on precordium of subject and temporarily secured with, for example, adhesive tape. Cable extending from second Doppler ultrasound transducer is connected to monitor using connector at proximal end of cable at designated receptacle on monitor. By way of example, position of such second Doppler ultrasound transducer and securing adhesive tape are shown as 182 and 184 in FIG. 1.

As represented at arrow 214 to block 216 of FIG. 18A, digital image sensor is removably attached to microbubble counting cell located between three-way stopcock and flexible catheter. Cable extending from digital image sensor is connected to monitor using connector at proximal end of cable at designated receptacle on monitor. The digital image sensor and microbubble counting cell are shown as 130 and 44 in FIG. 1.

Still referring to FIG. 18A, the program continues as represented at arrow 218 to block 220 to designate the start of the at-rest test to detect, if present, the conductance of a right-to-left shunt and determine the Grade of a detected shunt. The first shunt test is conducted without the subject performing any provocative maneuver. Two purposes are accomplished by conducting a shunt test in the absence of performing a provocative maneuver by the subject. The first purpose is to determine if the subject has a very large right-to-left shunt, e.g., an atrial septal defect that represents an opening between the right and left atria that is always open and does not require the creation of a right-to-left pressure gradient provided by a provocative maneuver to enable the transport of microbubble-containing contrast agent directly across the intervening septal wall separating the right atrium from the left atrium and bypassing the microbubble filtering effect of normal passage through the lungs. If microbubbles are detected in intracranial arteries without the right-to-left pressure gradient created by a provocative maneuver, then it confirms that the subject has a right-to-left shunt with a very large conductance and further shunt tests with the addition of a Valsalva maneuver are contraindicated. The second purpose of performing the first test with the subject at rest (i.e., without performing any provocative maneuver) is to enable the measurement of the transit time between the start of injection of the contrast agent into the venous blood stream of the subject and the arrival of the contrast agent in the right atrium. There are multiple subject-dependent factors that can affect the transit time including, but not limited to, lumen sizes and volumetric capacity of venous pathway between the site of injection into venous blood flow (e.g., antecubital vein) and cardiac output of subject. The measurement of the actual transit time for the subject performing a shunt test enables the timing of the start of injection of contrast agent in subsequent shunts wherein a provocative maneuver, viz., a Valsalva maneuver, is performed. It is therefore essential that the actual transit time be accurately known since the Valsalva maneuver is automatically ended or "released" by the controller upon the detection of the arrival of the microbubble-containing contrast agent in the right atrium. However, it is also essential that the duration of the Valsalva maneuver be at least 5.0 seconds to achieve an adequate provocative maneuver, but not more than 10.0 seconds, since the latter duration may exceed the breath-hold capability of the subject. Hence, the start of the injection of the contrast agent by the operator is prompted by the monitor to ensure that the duration of the Valsalva maneuver is at least 5.0 seconds and not more than 10.0 seconds.

Still referring now to FIG. 18A, the program continues as represented by arrow 222 to block 224. At this step, operator fills second syringe with a predetermined amount of isotonic saline (e.g., 10 ml). In the next step as represented by arrow 226 and block 228, operator fills first syringe with a predetermined amount of isotonic saline (e.g., 8.0 ml). Next, operator withdraws a predetermined amount of air into first syringe (e.g., 1.0 ml). Next, as represented by arrow 230 and block 232, operator places a venous access needle in a peripheral vein of subject (e.g., antecubital vein at right arm). Following placement of venous access needle in subject's vein, operator connects first syringe to proximal end of venous access needle tubing and withdraws a predetermined amount of the subject's blood (e.g., 1.0 ml) into first syringe. Alternatively, the step associated with the withdrawal of blood can be eliminated and the contrast agent 45 may comprise a mixture of only isotonic saline (e.g., 9.0 ml) and air (1.0 ml) that is exchanged between syringes 47 and 41 to create microbubbles. Alternatively, other sterile isotonic aqueous solutions suitable for IV injection may be used in place of an isotonic saline solution, for example, sterile Ringers isotonic solution.

Referring now to FIG. 18B, as represented by arrow 234 to block 236, operator connects first and second syringes to two ports on injection catheter set with first syringe connected to first port of three-way stopcock and second syringe is connected to second port of three-way stopcock.

Still referring now to FIG. 18B, as represented at arrow 238 to block 240, operator opens three-way stopcock between [1] second syringe and [2] microbubble counting cell and flexible catheter to expel isotonic saline in second syringe through microbubble counting cell and flexible catheter to remove all air from these components. At the end of this step, plunger in second syringe is fully forward in the chamber of the syringe. In the next step, as represented at arrow 242 to block 244, operator connects distal end of isotonic saline-filled flexible catheter in catheter set to fitment at proximal end of venous access needle tubing. Arrangement of first syringe, second syringe, three-way stopcock, microbubble counting cell, digital image sensor, flexible catheter and venous access needle are shown as 47, 41, 43, 44, 130, 42 and 48, respectively, in FIG. 1.

Still referring to FIG. 18B, as represented at arrow 246 to block 248, operator closes three-way stopcock in direction of microbubble counting cell and opens three-way stopcock in directions of first and second syringes in preparation for the start of the agitation process to create microbubbles in the isotonic saline/air/blood mixture currently residing in first syringe.

Still referring now to FIG. 18B, as represented at arrow 250 to block 252, operator starts agitation process by rapidly expelling saline/air/blood mixture from first syringe into empty second syringe and then rapidly expelling saline/air/blood mixture from second syringe back into empty first syringe to complete the first agitation cycle. The operator next promptly repeats additional agitation cycles in close succession for a total of preferably nine additional agitation cycles but at least five additional agitation cycles so that the completion of the final agitation cycle results in the agitated saline contrast agent residing in first syringe. At the completion of the last agitation cycle, as represented at arrow 254 to block 256, operator immediately closes three-way stopcock in direction of empty second syringe and opens three-way stopcock between first syringe and direction of microbubble counting cell, flexible catheter and venous access needle.

Still referring now to FIG. 18B, as represented at arrow 258 to block 260, operator promptly expels contrast agent residing in first syringe into vein of subject along path that includes microbubble counting cell, flexible catheter and venous access needle. This step taken by operator also starts transit time clock in controller based on detection of semi-opaque contrast agent entry into the microbubble counting cell using image camera.

Referring now to FIG. 18C, as represented at arrow 262 to block 264, when second Doppler ultrasound transducer positioned at precordial location on subject detects arrival of echogenic microbubbles in right atrium of subject the elapsed transit time clock is stopped. This measured transit time for the flow of injected contrast agent from detected entry into microbubble counting cell to the detected arrival of contrast agent at right atrium is recorded by controller, saved in memory of controller and designated as tTRANSIT. By way of example, the measured value of the Transit Time, tTRANSIT, may be 4.1 seconds.

Still referring to FIG. 18C, as represented at arrow 266 to block 268, the digital image sensor automatically records the image of the contrast agent in the microbubble counting zone within the microbubble counting cell. This recorded image of microbubbles within the microbubble counting zone next is automatically analyzed in the controller using a software-based image analysis algorithm to determine the number of microbubbles within the microbubble counting zone of the microbubble counting cell. The derived count of microbubbles within the microbubble counting zone is next used by controller to ratiometrically compute the number of microbubbles in the operator specified volume (e.g., 10 ml) of injected contrast agent. By way of example, if the volume of the microbubble counting zone is 0.225 cubic millimeters (i.e., 0.000225 cubic centimeter) and the total injected volume of injected microbubble-containing contrast agent is 10.0 ml or 10.0 cubic centimeters, then the multiplying factor for the ratiometric analysis is 10 cubic centimeter/ 0.000225 cubic centimeter or 44,444. In this example, if the number of bubbles counted in microbubble counting zone is 640, then number of microbubbles in 10 ml volume of contrast agent, referred to herein after as NBUBBLES, is about 28.5 million microbubbles.

Still referring next to FIG. 18C, as represented at arrow 270 to block 272, controller records reflected ultrasound signals from Doppler ultrasound transducer arrays positioned at one or both insonated hemispheres of the skull of the subject adjacent to targeted intracranial arteries during a predefined time interval, tCOUNT beginning with the detected arrival of microbubble-filled contrast agent in the right atrium and ending after an elapsed time interval, tCOUNT (e.g., 30.0 second time interval). Next, as represented at arrow 274 to block 276, a software-based algorithm in controller analyzes reflected Doppler ultrasound signals recorded by first Doppler ultrasound array(s) to determine number of detected embolic tracks corresponding to and produced by movement of blood-borne microbubbles in intracranial arteries, NET (for example, assume a NET value of 110).

Still referring to FIG. 18C, as represented at arrow 278 to block 280, controller computes Microbubble Adjustment Ratio, RBUBBLES by dividing [1] a pre-established reference number of injected microbubbles, NREF (e.g., NREF=6.0 million microbubbles) that was used to develop a standard Grading Scale for the conductance of right-to-left shunts by [2] the estimated number of microbubbles in the total volume of the injected contrast agent, NBUBBLES (e.g., 28.5 million microbubbles). In the present example, the Microbubble Adjustment Ratio, RBUBBLES=NREF/ NBUBBLES=6.0/28.5, which equals 0.21.

Referring now to the next computation step in FIG. 18D, as represented at arrow 282 to block 284, controller multiplies the number of detected Embolic Tracks, NET by the derived Microbubble Adjustment Ratio, RBUBBLES to derive the microbubble count adjusted number of Embolic Tracks, NADJET. In the present example, NADJET=NET× RBUBBLES=110×0.21=23. Still referring to FIG. 18D, adjusted number of Embolic Tracks, NADJET is next used in combination with the pre-established standard grading scale to determine the grade of the conductance of a right-to-left shunt and display results on screen of monitor. In this particular example, assume a standard shunt grade scale, such as the Spencer Scale (previously reported in Spencer, M. et al., Power M-Mode Transcranial Doppler for Diagnosis of Patent Foramen Ovale and Assessing Transcatheter Closure. Journal of Neuroimaging 2004; 14:342-349), as follows: Very Large shunt conductance (Grade V, >300 Embolic Tracks or ETs), Large shunt conductance (Grade IV, 101-300 ETs), Medium shunt conductance (Grade III, 31-100 ETs), Small shunt conductance (Grade II, 11-30 ETs) and Very Small shunt conductance (Grade I, 1-10 ETs). The application of this Grade Scale depends on the number of injected microbubble. However, prior art use of this Grade Scale since is publication in 2004 makes no correction for the actual number of microbubbles injected. No adjustment was possible in prior art shunt detection and quantification methods since the number of injected microbubbles was unknown and can differ by more than fifty-fold depending on the agitation method, agitated saline composition and delay time associated with the injection of the agitated saline contrast agent. In the present example and using the existing standard Grading Scale specified above, the grade for the detected shunt in the example case based on an unadjusted Embolic Track count of 110 would have been Grade IV corresponding to a Large shunt conductance. However, in this example, the microbubble-count adjusted number of Embolic Tracks was only 23 corresponding to a Grade II corresponding to a Small shunt conductance. However, due to the various factors that can affect the number of microbubbles contained within the injected contrast agent, as described in the present specification, the unadjusted and adjusted grades could differ by as many as three grades. This much variation in the measured number of Embolic Tracks, without adjustment for the actual number of injected microbubbles in the contrast agent, significantly limits the ability to assess the level of residual or recurrent shunting after completion of a transcatheter shunt closure procedure.

Still referring to FIG. 18D, as represented at arrow 290 to block 292, controller determines whether shunt test index, NTEST is greater than 1. At this stage of the program, NTEST is equal to an integer value 1, the value set in Block 204 in FIG. 18A. Therefore, the program proceeds as represented at arrow 304 to block 305 representing the end of the at-rest shunt test that is also the initial test in the test sequence. The program continues, as represented at arrow 306 and block 307 such that the controller determines whether the adjusted number of Embolic Tracks, NADJET is greater than a predetermined maximum number of Embolic Tracks, NRESTMAX during the at-rest test. If the adjusted number of Embolic Tracks, NADJET measured during the at-rest shunt test is greater than the operator specified maximum number of Embolic Tracks, NREST-MAX, then shunt testing is discontinued as represented at arrow 308 and block 309. Shunt testing is discontinued since a measured adjusted number of Embolic Tracks, NADJET greater than an operator specified maximum number under at-rest conditions could expose the subject to significant transport of microbubbles into the arterial circulation under conditions when the subject performs a Valsalva maneuver.

Still referring to FIG. 18D, as represented at arrow 294 to block 296, if the shunt test index, NTEST is greater than 1 (corresponding to the case in which the at-rest test has already been performed and the value of the shunt test index, NTEST was incremented a value greater than 1 in block 311), then the display of the monitor issues a query to the operator regarding the operator's intention to perform another shunt test. If the operator enters a response on the monitor display (e.g., touch actuated screen) that the operator does not intend to continue with any additional shunt testing, then the monitor displays that shunt testing has been completed, as represented at arrow 300 and block 302. However, as represented at arrow 298 to block 311, if the operator elects to continue shunt testing when the shunt test index, NTEST is already greater than 1, then the shunt test index, NTEST is incremented by the number 1.

Likewise, referring to FIG. 18D as represented at arrow 310 to block 311, if the adjusted number of Embolic Tracks, NADJET, measured during the at-rest shunt test is not greater than the operator specified maximum number of Embolic Tracks, NRESTMAX, then shunt testing continues with the addition of the Valsalva maneuver during subsequent shunt tests and the shunt test index, NTEST is incremented by the integer value 1. The program continues, as represented at arrow 312 to block 314, to the start of the next shunt test performed in combination with a Valsalva maneuver.

In preparation for the next shunt test, as seen in FIG. 18D as represented at arrow 316 and block 318, operator fills second syringe with a predetermined amount of isotonic saline (e.g., 10 ml) and fills first syringe with a predetermined amount of isotonic saline, (e.g., 8.0 ml) and next withdraws a predetermined amount of air into the first syringe (e.g., 1.0 ml).

Turning now to FIG. 18E, as represented at arrow 320 to block 322, operator connects first and second syringes to two ports on injection catheter set with first syringe connected to first port of three-way stopcock and second syringe connected to second port of three-way stopcock. Next, as represented at arrow 324 to block 326, operator connects distal end of contrast agent-filled microbubble counting cell and flexible catheter in catheter set to fitment at proximal end of venous access needle tubing. Following this connection step, as represented at arrow 328 to block 330, operator opens three-way stopcock between second syringe and microbubble counting cell as well as flexible catheter and then expels isotonic saline contents from second catheter through microbubble counting cell and flexible catheter and into vein of subject in order to remove all residual contrast agent from microbubble counting cell and flexible tubing, i.e., residual contrast agent associated with previous shunt test. At the end of this isotonic saline purging step to remove all residual contrast agent from the microbubble counting cell and flexible catheter, the plunger of the second syringe is now in the fully forward position in the chamber of the second syringe and the second syringe is empty.

Still referring to FIG. 18E, as represented at arrow 320 to block 322, operator closes three-way stopcock in direction of microbubble counting cell and opens three-way stopcock in directions of first and second syringes in preparation for the start of the agitation process to create microbubbles within the saline/air/blood mixture currently residing in first syringe.

Still referring now to FIG. 18E, as represented at arrow 336 to block 338, operator starts agitation process by rapidly expelling saline/air/blood mixture from first syringe into empty second syringe and then rapidly expelling saline/air/blood mixture from second syringe back into empty first syringe to complete the first agitation cycle. The operator next promptly repeats additional agitation cycles in close succession for a total of preferably nine additional agitation cycles but at least five additional agitation cycles so that the completion of the final agitation cycle results in the agitated saline contrast agent residing in first syringe. At the completion of the last agitation cycle, as represented at arrow 340 to block 342, operator immediately closes three-way stopcock in direction of empty second syringe and opens three-way stopcock between first syringe and direction of microbubble counting cell, flexible catheter and venous access needle.

Although the creation of a contrast agent containing saline/air/blood mixture represents a preferred embodiment of the present disclosure, the step associated with the withdrawal of blood can be eliminated and the contrast agent 45 may alternatively comprise a mixture of only isotonic saline (e.g., 9.0 ml) and air (1.0 ml) that is exchanged between syringes 47 and 41 to create microbubbles. Alternatively, other sterile isotonic aqueous solutions suitable for IV injection may be used in place of an isotonic saline solution, for example, sterile Ringers isotonic solution.

Still referring to FIG. 18E, as represented at arrow 344 to block 346, operator provides for the initialization of the shuttle location in the mouthpiece assembly 20 by activating one evacuation cycle followed by one pressurization cycle to position shuttle in the initial "home" position within the tubular body of the mouthpiece assembly 20. Next, referring to FIG. 18F, the program starts measurement as represented at arrow 348 extending to block 350, wherein instructions are provided to the subject to begin the Valsalva maneuver by exhaling into the ergonomic tube 22 of the mouthpiece assembly 20, as seen in FIG. 1, to reach and maintain the target pressure level until the monitor terminates the Valsalva maneuver automatically after the second Doppler ultrasound transducer detects the arrival of the microbubble-containing contrast agent in the right atrium of the subject.

Generally, some form of display accompanies the Valsalva maneuver procedure on monitor 10. Turning momentarily to FIG. 1, a line graph 123 is provided along with a minimum exhalation pressure level 125, represented as a solid horizontal line, giving the subject the actual real-time measurement of the pressure being exerted by the subject during the Valsalva maneuver. The graph display 124 shows exhalation pressure versus elapsed time. In FIG. 1, the subject's Valsalva exhalation pressure has just been released automatically by the combined operation of the solenoid-driven vacuum/pressurization assembly and mouthpiece assembly seen at release time point 129 in FIG. 1. As seen at display screen 124 of FIG. 1, the Valsalva maneuver was properly ended with the graph 123 displaying that the subject held the proper pressure (with some acceptable variation) during the duration of the Valsalva maneuver.

Returning to FIG. 18F, as represented at arrow 352 to block 354, the exhalation pressure created by the subject during the Valsalva maneuver is continuously measured and displayed on the monitor, as explained in connection with FIG. 1, and is compared to the ideal Valsalva curve or required minimum exhalation pressure level 125. As represented by arrow 356 to block 358, the exhalation pressure is queried and it is determined whether it falls within a measurable range, for example from 0-4000 analog-to-digital converted (ADC) units. If not, arrow 360 is followed to block 362, wherein a system fault is displayed and the test is ended. If the measured exhalation pressure is within an expected range, arrow 364 is followed to block 366.

Still referring to FIG. 18F, block 366 poses the query as to whether the exhalation pressure level is greater to or equal to the targeted pressure, for example, 40 mm Hg. In the event that it is not, as represented at arrow 368 and block 370, the operator is alerted with an audible alarm and/or visual error message to instruct the patient to increase pressure to meet or exceed the target exhalation pressure level. Where the exhalation pressure is appropriate, the program continues as represented at arrow 374.

Still referring to FIG. 18F, as represented at arrow 374, extending from the query at block 366 and leading to block 376, the Time Interval elapsed time clock $t_1$ is set to $t_1=0$ and begins the countdown (i.e., count up) to a derived Injection Time Interval value, TIINJECT. The Injection Time Interval value, TIINJECT, is computed within controller based on two parameters. A first parameter is a time value, tVALSAVAMIN, that corresponds to the minimum Valsalva duration and that is sufficient to ensure that the controller does not automatically end (i.e., release) the Valsalva maneuver sooner than the minimum required Valsalva maneuver duration of 5.0 seconds. A second parameter is the measured Transit Time, tTRANSIT, corresponding to the elapsed time between the start of injection of the contrast agent into a vein of the subject and the time of arrival of the contrast agent in the right atrium, as detected by the second Doppler ultrasound transducer at the precordial position on the subject. The Injection Time Interval value, TIINJECT is derived by selecting a first parameter time value, tVALSAVAMIN, that is sufficiently larger than the measured Transit Time, tTRANSIT, such that, once the subject begins the Valsalva maneuver (defined by the controller as the time at which the exhalation pressure sustainably exceeds 40 mm Hg), the operator is prompted by the monitor to start the contrast agent injection when time interval, TIINJECT, has expired following the controller-defined beginning of the Valsalva maneuver. By way of example, if first parameter time value, tVALSAVAMIN, is 6.0 seconds and measured Transit Time, tTRANSIT, is 3.0 seconds, then the computed value of Injection Time Interval, TIINJECT value is obtained by subtracting the measured Transit Time, tTRANSIT, from the first parameter time value, tVALSAVAMIN, which equals 6.0 seconds–3.0 seconds or 3.0 seconds. If the operator starts the injection of the contrast agent at the instant that the audible cue is issued by the monitor, then the total duration of the Valsalva maneuver will be 6.0 seconds since there is a 3.0 second delay after the start of the Valsalva maneuver before the start of the injection of the contrast agent plus a 3.0 second additional elapsed time for the injected contrast agent to reach the right atrium (corresponding to the Transit Time, tTRANSIT, measured in the initial at-rest shunt test). In this example, if the response time of the operator to begin the start of the contrast agent after hearing the audible cue issued by the monitor to "start injection" is 1.0 second, then this operator response time delay correspondingly adds to the total Valsalva duration such that the actual Valsalva maneuver duration becomes 7.0 seconds.

Still referring to FIG. 18F, as represented at arrow 378 to block 380, block 380 poses the query as to whether the elapsed time since the subject begins the Valsalva maneuver (defined by the controller as the time at which the exhalation pressure sustainably exceeds 40 mm Hg) is greater than the Injection Time Interval, TIINJECT, where TIINJECT is equated to 6.0–tTRANSIT. In the event that it is not, as represented at arrow 381 and block 382, the program continues to query whether the exhalation pressure level exerted by the operator is greater to or equal to the targeted Valsalva pressure, PVALSALVA (e.g., 40 mm Hg). In the event that it is not, as represented at arrow 383 and block 370, the operator is alerted with an audible alarm and/or visual error message to instruct the patient to increase pressure to meet or exceed the target exhalation pressure level. In the event that the exhalation pressure is above the targeted Valsalva pressure, PVALSALVA, as represented at arrow 384, the program continues and block 382, the program continues to query whether the elapsed time since the subject begins the Valsalva maneuver is greater than the Injection Time Interval, TIINJECT (where TIINJECT is equated to the value 6.0–tTRANSIT).

Referring now to FIG. 18F and FIG. 18G, when the elapsed time since the subject begins the Valsalva maneuver is greater than the Injection Time Interval, TIINJECT, then the program continues, as represented at arrow 385 and block 386 by causing the monitor to issue an audible cue to the operator to start the injection of the contrast agent into the vein of the subject. In response to the audible cue issued by the monitor, as represented at arrow 388 and block 389, operator promptly expels the microbubble-containing contrast agent residing in the first syringe into the vein of the subject along the flow path that includes the microbubble counting cell, flexible catheter and the venous access catheter.

Still referring to FIG. 18G, as represented at arrow 390 to block 391, block 391 poses the query whether the second Doppler ultrasound transducer at the precordial position on subject has detected the arrival of the microbubble-containing contrast agent in the right atrium. If the detection of the arrival of the contrast agent in the right atrium has not yet occurred, then the query continues as represented at arrow 392 and returning to query block 391. When the second Doppler ultrasound transducer at the precordial position on subject does detect the arrival of the microbubble-containing contrast agent in the right atrium, then the program continues, as represented at arrow 394 to block 396 at which time the solenoid 84, as seen in FIG. 1, is energized by power supply (not shown) within controller 60, forcing a rapid retraction of the piston 94 in the vacuum/pressurization subassembly and inducing a vacuum level (i.e., negative pressure level) sufficient to rapidly retract the shuttle in the mouthpiece assembly 20. Upon the retraction of the shuttle, as seen in FIG. 4, one or more vents 26 in the mouthpiece assembly 20 are in low-resistance, air-flow communication with the mouth 4 and lungs of patient 8 as seen in FIGS. 1 and 4, thereby inducing the immediate expiration of air from the lungs of patient 8 and the corresponding end of the Valsalva maneuver. This process controllably ends the Valsalva maneuver ended at the precise time at which the microbubble-containing contrast agent arrives in the right atrium and the end of the Valsalva maneuver does not depend on the response time of patient 8 to any audible and/or visual cues to initiate their own action to end the Valsalva maneuver.

Still referring to block 396 of FIG. 18G as well as FIG. 1, within a predetermined time after solenoid 84 is energized and vents 26 "open" (e.g., a time period of 5.0 seconds), solenoid 84 is de-energized at which time the restraining force holding piston 94 in the retracted position, as seen in FIG. 1, becomes zero. At this moment, the force exerted by compression spring 120 in its contracted state induces a rapid return of piston 94 to its distal starting position. The rapid return of piston 94 to its distal starting position induces a positive pressure in the internal tubing assembly 100 and extension tubing 36, thereby forcing the shuttle in the mouthpiece assembly 20 to return to its proximal starting ("home") position as seen in FIGS. 1 and 3.

Referring now to both FIG. 18C and FIG. 18G, program continues as represented at arrow 398 and block 400 to repeat shunt tests steps beginning, as represented at arrow 402 to block 268 with the determination of the number of microbubbles in the contrast agent just injected into vein of subject, as specified in block 389. As seen in FIG. 18C through FIG. 18G, the previously described shunt tests are repeated until the last shunt test is completed.

All terms not specifically defined herein are considered to be defined according to Dorland's Medical Dictionary, and if not defined therein according to Webster's New Twentieth Century Dictionary Unabridged, Second Edition.

While the apparatus, method, and system have been described with reference to various embodiments, those skilled in the art will understand that various changes may be made and equivalents may be substituted for elements thereof without departing from the scope and essence of the disclosure. In addition, many modifications may be made to adapt a particular situation or material to the teachings of the disclosure without departing from the essential scope thereof. Therefore, it is intended that the disclosure not be limited to the particular embodiments disclosed, but that the disclosure will include all embodiments falling within the scope of the appended claims. All citations referred herein are expressly incorporated herein by reference.

We claim:

1. A method for estimating a total number of microbubbles contained within a known volume of contrast agent being injected into a vein of a patient to quantify a conductance of a right-to-left cardiac shunt after adjusting a number of detected embolic tracks, NET, based on the total number of microbubbles contained within the injected contrast agent the method comprising the steps of:
   a. preparing microbubble containing contrast agent (45) by repeatedly and cyclically exchanging a mixture of saline, air and blood between a first syringe (47) and a second syringe (41) wherein initially the first syringe containing the saline/air/blood mixture is fully and rapidly expelled by an operator into the empty second syringe and then the process is immediately reversed and the saline/air/blood mixture is rapidly expelled back into the first syringe representing one complete agitation cycle, this agitation cycle being repeated for at least six complete cycles to affect the agitation required to create the total number of microbubbles;
   b. positioning an optically transparent microbubble counting cell (44) external to the patient along a pathway between the contrast agent containing first syringe and a venous access needle (48) placed in the vein of the patient;
   c. attaching an image sensor (130) having a field of view to the optically transparent microbubble counting cell, the image sensor communicating with a controller;
   d. injecting the contrast agent into an interior chamber of the optically transparent microbubble counting cell located between the contrast agent containing first syringe and the venous access needle;
   e. imaging the microbubbles within a predefined microbubble counting zone (146) occupying a known volume within the microbubble counting cell (44) as seen in the field of view of the image sensor attached to the microbubble counting cell (44) to capture an image of a layer of injected contrast agent within the microbubble counting zone (146) within the microbubble counting cell (44) as the contrast agent is injected through the venous access needle (48) and into the patient;
   f. counting a number of microbubbles within the microbubble counting zone of the microbubble counting cell, NCOUNT, by an automated image analysis in the controller of a recorded image of microbubbles within microbubble counting zone (146) acquired by the image sensor (130); and
   g. estimating the total number of microbubbles within the known volume of injected contrast agent, NBUBBLES, injected through the venous access needle (48) and into the vein (5) of the patient by multiplying the number of microbubbles counted within the microbubble counting zone in step in [f], NCOUNT, by the ratio of the known volume of the injected contrast agent (45) injected into the vein of the patient divided to the known volume of the microbubble counting zone (146).

2. The method of claim 1, wherein the known volume of the injected contrast agent is 10 cubic centimeters and the volume of the known volume of the predefined microbubble counting zone of the microbubble counting cell is 0.000225 cubic centimeters.

3. The method of claim 1, wherein the ratio of the known volume of injected contrast agent to the known volume of the microbubble counting zone is 44,444.

4. The method of claim 1, wherein the controller computes a microbubble adjustment ratio, RBUBBLES, by dividing a pre-established reference number, NREF, of microbubbles within an injected contrast agent by the total estimated number of microbubbles within the injected contrast agent, NBUBBLES, obtained in step [g].

5. The method of claim 1, wherein additional steps within the controller include:
   a. recording and analyzing reflected ultrasound signals from one or more Doppler ultrasound transducers positioned at one or both insonated hemispheres of a skull of the patient adjacent to targeted intracranial arteries during a time interval, tCOUNT, to determine the number of detected embolic tracks corresponding to and produced by movement of blood-borne microbubbles within intracranial arteries, NET: and
   b. multiplying the number of detected embolic tracks, NET, by the microbubble adjustment ratio, RBUBBLES, to obtain a microbubble count adjusted number of embolic tracks, NADJET.

6. The method if claim 5, wherein the time interval, tCOUNT, is 30 seconds.

* * * * *